United States Patent
Auvin et al.

(10) Patent No.: US 7,473,779 B2
(45) Date of Patent: Jan. 6, 2009

(54) DERIVATIVES OF AMIDINES, THEIR PREPARATION, THEIR USE AS MEDICAMENTS AND THE PHARMACEUTICAL COMPOSITIONS CONTAINING THEM

(75) Inventors: Serge Auvin, Mauchamps (FR); Pierre-Etienne Chabrier de Lassauniere, Paris (FR); Jeremiah Harnett, Gif-sur-Yvette (FR); Dominique Pons, Paris (FR); Gérard Ulibarri, Bures-sur-Yvette (FR)

(73) Assignee: Societe de Conseils de Recherches et d'Applications Scientifiques (S.C.R.A.S.), Paris (FR)

( * ) Notice: Subject to any disclaimer, the term of this patent is extended or adjusted under 35 U.S.C. 154(b) by 855 days.

(21) Appl. No.: 10/662,183

(22) Filed: Sep. 12, 2003

(65) Prior Publication Data

US 2005/0261269 A1     Nov. 24, 2005

Related U.S. Application Data

(62) Division of application No. 09/787,467, filed as application No. PCT/FR99/02250 on Sep. 22, 1999, now Pat. No. 6,653,312.

(30) Foreign Application Priority Data

Sep. 23, 1998   (FR)   ................................. 98 11868

(51) Int. Cl.
| | |
|---|---|
| A01N 43/00 | (2006.01) |
| A01N 43/40 | (2006.01) |
| A01N 43/36 | (2006.01) |
| A01N 37/52 | (2006.01) |
| A61K 31/397 | (2006.01) |
| A61K 31/55 | (2006.01) |
| A61K 31/445 | (2006.01) |
| A61K 31/40 | (2006.01) |
| A61K 31/155 | (2006.01) |
| C07D 223/04 | (2006.01) |
| C07D 211/26 | (2006.01) |
| C07D 211/28 | (2006.01) |
| C07D 207/46 | (2006.01) |
| C07D 295/04 | (2006.01) |
| C07D 205/00 | (2006.01) |
| C07C 257/00 | (2006.01) |

(52) U.S. Cl. ............. 540/611; 514/210.01; 514/212.01; 514/317; 514/408; 514/631; 546/231; 548/577; 548/950; 564/244

(58) Field of Classification Search .................... None
See application file for complete search history.

(56) References Cited

U.S. PATENT DOCUMENTS 6,335,445 B1 * 1/2002 Chabrier de Lassauniere et al. ........................ 544/358

OTHER PUBLICATIONS

Koti et al.; 2003; Digestive Surgery; vol. 20 p. 383-396.*
Chiou et al.; 2001; Journal of Ocular Pharmacology; vol. 17 p. 189-198.*
Lacza et al.; 2001; Stroke—Journal of the American Heart Association; p. 2609-2614.*
Aslam, et al.; Pakistan Journal of Pharmacy; 1995; 8(2); 9-22, 17.*
King et al.; Encyclopedia of Reagents for Organic Synthesis; 2001; Palladium on Carbon; p. 1-12.*
Koti et. al.; 2003; Digestive Surgery; vol. 20 pp. 383-396.*
Chiou et. al.; 2001; Journal of Ocular Pharmacology; vol. 17, pp. 189-198.*
Lacza et. al.; 2001; Stroke - Journal of the American Heart Association; pp. 2609-2614.*
Aslam, et. al.; Pakistan Journal of Pharmacy; 1995; 8(2); 9-22, 17.*
King et. al.; Encyclopedia of Reagents for Organic Synthesis; 2001; Palladium on Carbon; pp. 1-12.*

* cited by examiner

*Primary Examiner*—James O. Wilson
*Assistant Examiner*—Jeffrey H Murray
(74) *Attorney, Agent, or Firm*—Charles A. Muserlian

(57) ABSTRACT

Novel derivatives of amidines of formula

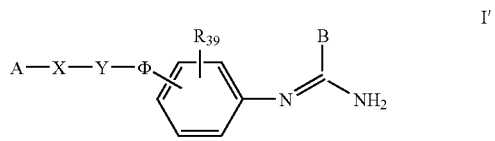

wherein the substituents are defined as in the specification which are useful for inhibiting activity on NO-synthase enzymes producing nitrogen mono oxide and/or trapping the reactive oxygen species (ROS) making them useful for treating various diseases.

2 Claims, No Drawings

DERIVATIVES OF AMIDINES, THEIR PREPARATION, THEIR USE AS MEDICAMENTS AND THE PHARMACEUTICAL COMPOSITIONS CONTAINING THEM

PRIOR APPLICATIONS

This application is a division of U.S. patent application Ser. No. 09/787,467 filed Mar. 16, 2001, now U.S. Pat. No. 6,653, 312, which is a 371 of PCT/FR99/02250 filed Sep. 22, 1999.

A subject of the present invention is new derivatives of amidines which have an inhibitory activity on NO-synthase enzymes producing nitrogen monoxide NO and/or an activity which traps the reactive oxygen species (ROS). The invention relates in particular to the derivatives corresponding to general formula (I) defined below, their preparation methods, the pharmaceutical preparations containing them and their use for therapeutic purposes, in particular their use as NO-synthase inhibitors and selective or non selective traps for reactive oxygen species.

BACKGROUND OF THE INVENTION

Given the potential role of NO and the ROS's in physiopathology, the new derivatives described corresponding to general formula (I) may produce beneficial or favourable effects in the treatment of pathologies where these chemical species are involved. In particular:

- Proliferative and inflammatory diseases such as for example atherosclerosis, pulmonary hypertension, respiratory distress, glomerulonephritis, portal hypertension, psoriasis, arthrosis and rheumatoid arthritis, fibroses, angiogenesis, amyloidoses, inflammations of the gastro-intestinal system (ulcerative or non ulcerative colitis, Crohn's disease), diarrhea.
- Diseases affecting the pulmonary system or airways (asthma, sinusitis, rhinitis).
- Cardio-vascular and cerebro-vascular disorders including for example, migraine, arterial hypertension, septic shock, ischemic or hemorragic cardiac or cerebral infarctions, ischemia and thromboses;
- Disorders of the central or peripheral nervous system such as for example neurodegenerative diseases where there can in particular be mentioned cerebral infarctions, subarachnoid hemorrhaging, aging, senile dementia including Alzheimer's disease, Huntington's chorea, Parkinson's disease, Creutzfeld Jacob disease and prion diseases, amyotrophic lateral sclerosis; ocular neuropathies such as glaucoma but also pain, cerebral and bone marrow traumas, addiction to opiates, alcohol and addictive substances, cognitive disorders, encephalopathies, and encephalopathies of viral or toxic origin;
- Disorders of the skeletal muscle and neuromuscular joints (myopathy, myosis) as well as cutaneous diseases.
- Cataracts.
- Organ transplants.
- Autoimmune and viral diseases such as for example lupus, AIDS, parasitic and viral infections, diabetes, and multiple sclerosis.
- Cancer.
- Neurological diseases associated with intoxication (Cadmium poisoning, inhalation of n-hexane, pesticides, herbicides), associated with treatments (radiotherapy) or disorders of genetic origin (Wilson's disease).
- All the pathologies characterized by an excessive production or dysfunction of NO and/or ROS's.

In all these pathologies, there is experimental evidence demonstrating the involvement of NO or ROS's (*J. Med. Chem.* (1995) 38, 4343-4362; *Free Radic. Biol. Med.* (1996) 20, 675-705; *The Neuroscientist* (1997) 3, 327-333).

Moreover, in earlier patents, the inventors already described NO Synthase inhibitors and their use (U.S. Pat. Nos. 5,081,148; 5,360,925), and more recently the combination of these inhibitors with products possessing antioxidant or antiradicular properties (Patent Application PCT WO 98/09653). In applications not yet published, they also described other derivatives of amidines or, more recently, derivatives of aminopyridines. These derivatives of amidines or aminopyridines have the characteristic of being both inhibitors of NO Synthases and inhibitors of ROS.

A subject of the present invention is new derivatives of amidines, their preparation and their therapeutic use.

The compounds of the invention correspond to general formula (I) characterized in that it comprises the compounds of general formula (I'):

BRIEF SUMMARY OF THE INVENTION

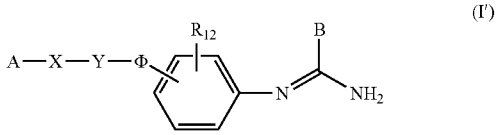

in which

A represents:

either a

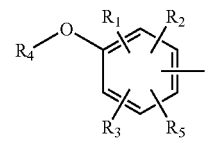

in which $R_1$, $R_2$ and $R_3$ represent, independently, a halogen, an OH or $SR_6$ group or a linear or branched alkyl, alkenyl or alkoxy radical having 1 to 6 carbon atoms, or a $NR_7R_8$ radical, $R_4$ representing a hydrogen atom or a linear or branched alkyl radical having 1 to 6 carbon atoms, $R_5$ represents a hydrogen atom, the OH or $SR_6$ group or a linear or branched alkyl or alkoxy radical having 1 to 6 carbon atoms, $R_6$ representing a hydrogen atom or a linear or branched alkyl radical having 1 to 6 carbon atoms, $R_7$ and $R_8$ independently representing a hydrogen atom, an OH group, a linear or branched alkyl radical having 1 to 6 carbon atoms or a —CO—$R_9$ radical in which $R_9$ represents a linear or branched alkyl radical having 1 to 6 carbon atoms;

or a

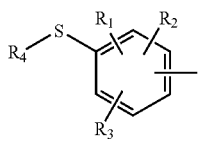

radical in which $R_1$, $R_2$ and $R_3$ represent, independently, a hydrogen atom, the OH or $SR_6$ group, a halogen or a linear or branched alkyl, alkenyl or alkoxy radical having 1 to 6 carbon atoms, or a $NR_7R_8$ radical, $R_4$ represents a hydrogen atom or a linear or branched alkyl radical having 1 to 6 carbon atoms, $R_6$ representing a hydrogen atom or a linear or branched alkyl radical having 1 to 6 carbon atoms, $R_7$ and $R_8$ independently representing a hydrogen atom, an OH group, a linear or branched alkyl radical having 1 to 6 carbon atoms or a —CO—$R_9$ radical in which $R_9$ represents a linear or branched alkyl radical having 1 to 6 carbon atoms;

or a

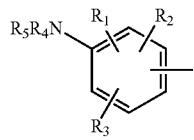

radical in which $R_1$, $R_2$ and $R_3$ represent, independently, a hydrogen atom, a halogen, the OH or $SR_6$ group, a linear or branched alkyl, alkenyl or alkoxy radical having 1 to 6 carbon atoms, or an $NR_7RS$ radical, $R_4$ and $R_5$ independently represent a hydrogen atom or a linear or branched alkyl radical having 1 to 6 carbon atoms, or $R_4$ and $R_5$ form together with the nitrogen atom an optionally substituted heterocycle having 4 to 7 members and 1 to 3 heteroatoms including the already present nitrogen atom, the additional heteroatoms being independently chosen from the group constituted by the O, N and S atoms, or furthermore $R_4$ represents an alkylsulphonyl, alkylsulphoxide or alkylcarbonyl radical and then $R_5$ represents H, $R_6$ representing a hydrogen atom or a linear or branched alkyl radical having 1 to 6 carbon atoms, $R_7$ and $R_8$ independently representing a hydrogen atom, an OH group, a linear or branched alkyl radical having 1 to 6 carbon atoms or a —CO—$R_9$ radical in which $R_9$ represents a linear or branched alkyl radical having 1 to 6 carbon atoms;

or a

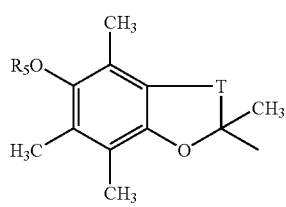

radical in which T represents a —$(CH_2)_k$— radical, k representing 1 or 2, and $R_5$ represents a hydrogen atom or a linear or branched alkyl radical having 1 to 6 carbon atoms or a

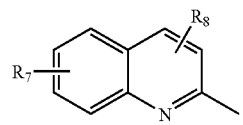

radical in which $R_7$ and $R_8$ represent, independently, a hydrogen atom or an OH group, or a

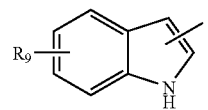

radical in which $R_9$ represents a hydrogen atom, the OH group or a linear or branched alkyl or alkoxy radical having 1 to 6 carbon atoms, or a

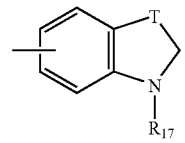

radical in which T represents a —$(CH_2)_k$— radical, k representing 1 or 2, and $R_{17}$ represents a linear or branched alkyl radical having 1 to 6 carbon atoms, or an arylalkyl, diarylalkyl, bis-arylalkyl, aminoalkyl, alkylaminoalkyl or dialkylaminoalkyl radical, or also $R_{17}$ represents a (heterocyclo)alkyl radical in which the heterocycle is saturated or unsaturated, has 3 to 7 members and includes at least a nitrogen atom, said nitrogen atom being optionally substituted by a hydrogen atom or an alkyl radical, or a

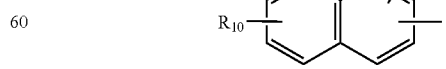

radical in which $R_{10}$ and $R_{11}$ represent, independently, a hydrogen atom or an OH group, or finally one of the

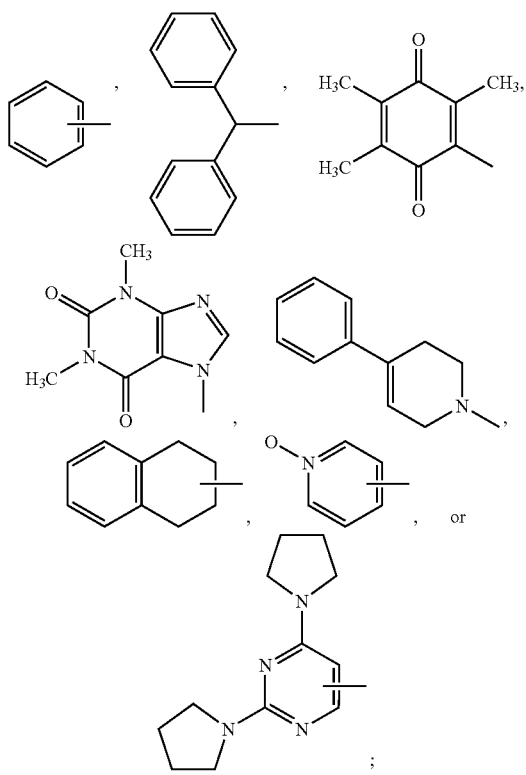

radicals,

B represents a linear or branched alkyl radical having 1 to 6 carbon atoms, carbocyclic or heterocyclic aryl with 5 or 6 members containing from 1 to 4 heteroatoms chosen from O, S, N and in particular the thiophene, furan, pyrrole or thiazole radicals, the aryl radical being optionally substituted by one or more groups chosen from the linear or branched alkyl, alkenyl or alkoxy radicals having 1 to 6 carbon atoms, or also B represents an $NR_{13}R_{14}$ radical, in which $R_{13}$ and $R_{14}$ represent, independently, a hydrogen atom or a linear or branched alkyl radical having 1 to 6 carbon atoms, or $R_{13}$ and $R_{14}$ form together with the nitrogen atom a non aromatic heterocycle with five to six members, the elements of the chain being chosen from a group comprising —$CH_2$—, —NH—, —O— or —S—;

X represents a bond or a —$(CH_2)_m$—, $(CH_2)_m$—CO, —O°$(CH_2)_m$—, S—$(CH_2)_m$—, —$NR_{15}$—$(CH_2)_m$—, —CO—$NR_{15}$—, —O—$(CH_2)_m$—CO—, —S—$(CH_2)_m$))$_m$—CO—, —$NR_{15}$—$(CH_2)_m$—CO—, —$(CH_2)_m$—C(OH)($CH_3$)—CO—, —CH=CH— or —CH=N— radical;

Y represents a bond or a —$(CH_2)_n$—, or —$(CH_2)_r$-Q-$(CH_2)_s$— radical,

Q representing a piperazine, homopiperazine, 2-methylpiperazine, 2,5-dimethylpiperazine, piperidine, 1,2,3,6-tetrahydropyridine, pyrrolidine, azetidine or thiazolidine radical or a saturated carbon ring having 3 to 7 members;

Φ represents a bond or a —$(CH_2)_p$—O—$(CH_2)_q$—, —$(CH_2)_p$—S—$(CH_2)_q$—, —$(CH_2)_p$—$NR_{16}$—$(CH_2)_q$—, —$(CH_2)_p$—CO—$NR_{16}$—$(CH_2)_q$— or —CO—$(CH_2)_p$—$NR_{16}$—$(CH_2)_q$— radical;

$R_{12}$ represents a hydrogen atom or a linear or branched alkyl or alkoxy radical having 1 to 6 carbon atoms;

$R_{15}$ and $R_{16}$ represent, independently, a hydrogen atom or a linear or branched alkyl radical having 1 to 6 carbon atoms or a —CO—$R_{18}$ radical in which $R_{18}$ represents a linear or branched alkyl or alkoxy radical having 1 to 6 carbon atoms;

m, n, p, q, r and s being integers from 0 to 6;

it being understood that:

if A represents the

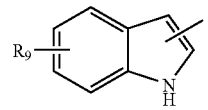

radical then Y represents the piperidine radical;

if A represents the

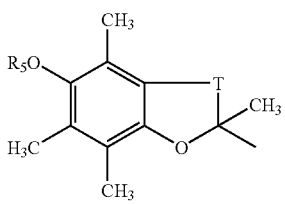

radical then Y represents a —$(CH_2)_r$-Q-$(CH_2)_s$— radical in which Q represents a saturated carbon ring having 3 to 7 members;

and if A represents the

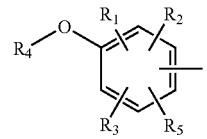

radical with at least two of the $R_1$, $R_2$, $R_3$ and $R_5$ radicals representing H, then X represents a —CH=CH— or —CH=N— radical and the X—Y-Φ- group does not represent a —CH=CH—CO-ω- radical in which ω represents any radical;

said general formula (I) also comprising the following compounds:

2-hydroxy-5-methoxy-N-{2-[4-[(2-thienyl(imino)methyl)amino]phenyl]ethyl}-benzamide;

2,5-dihydroxy-N-{2-[4[(2-thienyl(imino)methyl)amino]phenyl]ethyl-benzamide;

2-hydroxy-3-isopropyl-N-{2-[4-[(2-thienyl(imino)methyl)amino]phenyl]ethyl}-benzamide;

2,6-dihydroxy-N-{2-[4-[(2-thienyl(imino)methyl)amino]phenyl]ethyl}-benzamide;

2-hydroxy-4,6-dimethoxy-N-{2-[4-[(2-thienyl(imino)methyl)amino]phenyl]ethyl}benzamide;

2-hydroxy-3,5-di-tert-butyl-N-{2-[4-[(2-thienyl(imino)methyl)amino]phenyl]ethyl-benzamide;

2-hydroxy-0,3,5-di isopropyl-N-({2-[4-[(2-thienyl(imino)methyl)amino]phenyl]ethyl}-benzamide;

2-hydroxy-4-methoxy-N-{2-[4-[(2-thienyl(imino)methyl)amino]phenyl]ethyl}-benzamide;

2-hydroxy-3-isopropyl-5-methoxy-N-{2-[4-[(2-thienyl (imino)methyl)amino]phenyl]ethyl}-benzamide;
N-(2-hydroxy-3-tert-butyl-5-methoxy)-4-{[2-thienyl(imino) methyl]amino}benzene-butanamide;
3,4-dihydro-6-hydroxy-2,5,7,8-tetramethyl-N-{2-[4-[(2-thienyl(imino)methyl)amino]phenyl]ethyl}-2H-1-benzopyran-2-carboxamide;
3,4-dihydro-6-hydroxy-2,5,7,8-tetramethyl-N-{1-[4-[(2-thienyl(imino)methyl)amino]phenyl]methyl}-2H-1-benzopyran-2-carboxamide;
N-(4-hydroxyphenyl)-2-thiophenecarboximidamide;
N-(2-hydroxyphenyl)-2-thiophenecarboximidamide;
N-(3-hydroxyphenyl)-2-thiophenecarboximidamide;
N-(3-hydroxy-4-methoxyphenyl)-2-thiophenecarboximidamide;
N-(3-hydroxy-4-methylphenyl)-2-thiophenecarboximidamide;
N-(4-methoxyphenyl)-2-thiophenecarboximidamide;
N-(3,5-dimethyl-4-hydroxyphenyl)-2-thiophenecarboximidamide;
N-(3,5-dichloro-4-hydroxyphenyl)-2-thiophenecarboximidamide;
N-(2,6-bis-(1,1-dimethylethyl)-4-hydroxyphenyl)-2-thiophenecarboximidamide;
N-{4-[4-[(3,4-dihydro-6-hydroxy-2,5,7,8-tetramethyl-2H-1-benzopyran-2-yl)methyl]-1-piperazinyl]phenyl}-2-thiophenecarboximidamide;
1-(2-hydroxy-4,6-dimethoxybenzoyl)-3-{4-[(imino(2-thienyl)methyl)amino]phenoxy}azetidine;
N-(2-hydroxy-5-methoxy)-4-{[2-thienyl(imino)methyl] amino}benzene-butanamide;
N-(2-hydroxy-5-methoxy)-4-{[2-thienyl(imino)methyl] amino}benzene-propanamide;
N-(4-{[amino(2-thienyl)methylidene]amino}phenethyl)-2-hydroxy-5-methoxy-3-methylbenzamide;
(E)-N-(4-{[amino(2-thienyl)methylidene] amino}phenethyl)-3-(2-hydroxyphenyl)-2-propenamide;
(E)-N-(4-{[amino(2-thienyl)methylidene] amino}phenethyl)-3-(4-hydroxyphenyl)-2-propenamide;
(E)-N-(4-{[amino(2-thienyl)methylidene] amino}phenethyl)-3-(3,4-dihydroxyphenyl)-2-propenamide;
(E)-N-(4-{[amino(2-thienyl)methylidene] amino}phenethyl)-3-(4-hydroxy-3,5-dimethoxyphenyl)-2-propenamide;
3-[(3-{[amino(2-thienyl)methylidene]amino)-benzyl) amino]-N-[3,5-di(tert-butyl)-4-hydroxyphenyl]propanamide;
N'-(4-{2-[(2-hydroxy-4,6-dimethoxybenzyl)amino] ethyl}phenyl)-2-thiophenecarboximidamide;
N'-[4-(2-{[(6-hydroxy-2,5,7,8-tetramethyl-3,4-dihydro-2H-chromen-2-yl)methyl]amino}ethyl)phenyl]-2-thiophenecarboximidamide;
or also the salts of the products of general formula (I).

By alkyl, when no more precision is given, is understood a linear or branched alkyl; radical having 1 to 6 carbon atoms. By cycloalkyl, when no more precision is given, is understood a carbonated monocyclic system having 3 to 7 carbon atoms. By alkenyl, when no more precision is given, is understood a linear or branched alkyl radical having 1 to 6 carbon atoms and presenting at least one unsaturation (double bond). By alkynyl, when no more precision is given, is understood a linear or branched alkyl radical having 1 to 6 carbon atoms and presenting at least one double unsaturation (triple bond). By carbocyclic or heterocyclic aryl is understood a carbocyclic or heterocyclic system comprising at least an aromatic ring, a system being said heterocyclic when at least one of the cycles that constitute it comprises a heteroatom (O, N or S). By heterocycle is understood a mono- or polycyclic system, said system comprising at least a heteroatom chosen from O, N and S and being saturated, partially or totally unsaturated or aromatic. By haloalkyl is understood an alkyl radical of which at least one of the hydrogen atoms (and optionally all of them) is replaced by a halogen atom.

By alkylthio, alkoxy, haloalkyle, haloalkoxy, aminoalkyl, alkenyl, alkynyl and aralkyl radicals is understood respectively the alkylthio, alkoxy, haloalkyl, haloalkoxy, aminoalkyl, alkenyl, alkynyl, aralkyl and (heterocyclo)alkyl of which the alkyl radical has the meaning indicated previously.

By heterocycle is notably understood the thiophene, piperidine, piperazine, quinoline, indoline and indole radicals. By linear or branched alkyl having 1 to 6 carbon atoms, is understood in particular the methyl, ethyl, propyl, isopropyl, butyl, isobutyl, sec-butyl and tert-butyl, pentyl, neopentyl, isopentyl, hexyl, isohexyl radicals. Finally, by halogen, is understood fluorine, chlorine, bromine or iodine atoms.

Preferably, the compounds of general formula (I') are such that:

A represents:

either a

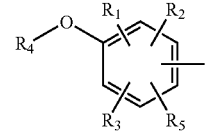

radical in which $R_1$, $R_2$ and $R_3$ represent, independently, the OH or $SR_6$ group or a linear or branched alkyl or alkoxy radical having 1 to 6 carbon atoms, $R_4$ representing a hydrogen atom or a linear or branched alkyl radical having 1 to 6 carbon atoms, $R_5$ represents a hydrogen atom, the OH or $SR_6$ group or a linear or branched alkyl or alkoxy radical having 1 to 6 carbon atoms, $R_6$ representing a hydrogen atom or a linear or branched alkyl radical having 1 to 6 carbon atoms, or a

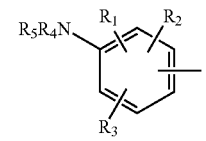

radical in which $R_1$, $R_2$ and $R_3$ represent, independently, a hydrogen atom, the OH group, a linear or branched alkyl or alkoxy radical having 1 to 6 carbon atoms, $R_4$ and $R_5$ represent independently a hydrogen atom or a linear or branched alkyl radical having 1 to 6 carbon atoms, or $R_4$ and $R_5$ form together with the nitrogen atom an optionally substituted heterocycle having 4 to 7 members and 1 to 3 heteroatoms including the already present nitrogen atom, the additional heteroatoms being independently chosen from the group constituted by the O, N and S atoms, or also $R_4$ represents an alkylsulphonyl or alkylcarbonyl radical and then $R_5$ represents H, or a

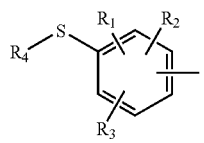

radical in which $R_1$, $R_2$ and $R_3$ represent, independently, a hydrogen atom, the OH or $SR_6$ group, a halogen or linear or branched alkyl, alkenyl or alkoxy radical having 1 to 6 carbon atoms, $R_4$ represents a hydrogen atom or a linear or branched alkyl radical having 1 to 6 carbon atoms, $R_6$ representing a hydrogen atom or a linear or branched alkyl radical having 1 to 6 carbon atoms, or a

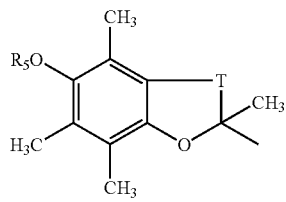

radical in which T represents a —$(CH_2)_k$— radical, k representing 1 or 2, and $R_5$ represents a hydrogen atom or a linear or branched alkyl radical having 1 to 6 carbon atoms or a

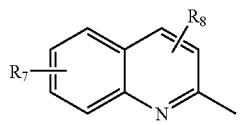

radical in which $R_7$ and $R_8$ represent, independently, a hydrogen atom or an OH group, or a

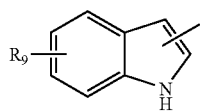

radical in which $R_9$ represents a hydrogen atom, the OH group or a linear or branched alkyl or alkoxy radical having 1 to 6 carbon atoms, or a

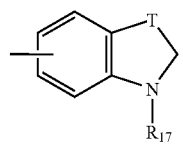

radical in which T represents a —$(CH_2)_k$— radical, k representing 1 or 2, and $R_{17}$ represents a linear or branched alkyl radical having 1 to 6 carbon atoms, or an arylalkyl, diarylalkyl, bis-arylalkyl, aminoalkyl, alkylaminoalkyl or dialkylaminoalkyl radical, or $R_{17}$ further represents a (heterocyclo)alkyl radical in which the heterocycle is saturated or unsaturated, has 3 to 7 members and includes at least a nitrogen atom, said nitrogen atom being optionally substituted by a hydrogen atom or an alkyl radical, or a

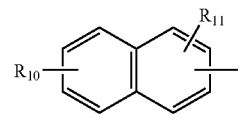

radical in which $R_{10}$ and $R_{11}$ represent, independently, a hydrogen atom or an OH group, or finally one of the

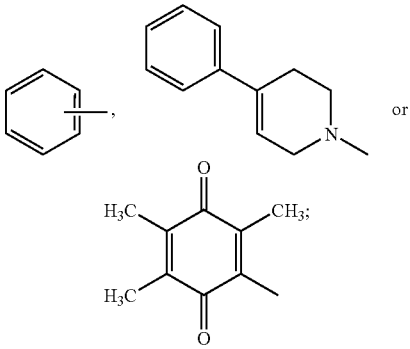

radicals

B represents a linear or branched alkyl radical having 1 to 6 carbon atoms, carbocyclic or heterocyclic aryl with 5 or 6 members containing from 1 to 4 heteroatoms chosen from O, S, N and in particular the thiophene, furan, pyrrole or thiazole radicals, the aryl radical being optionally substituted by one or more groups chosen from the linear or branched alky, alkenyl or alkoxy radicals having 1 to 6 carbon atoms, X represents a bond or a —$(CH_2)_m$—, —$(CH_2)_m$—CO, —O—$(CH_2)_m$—, S—$(CH_2)_m$—, —$NR_{15}$—$(CH_2)_m$, —CO—$NR_{15}$—, —O—$(CH_2)_m$—CO—, —S—$(CH_2)_m$—CO—, —$NR_{15}$—$(CH_2)_m$—CO— or —$(CH_2)_m$—C(OH)($CH_3$)—CO— radical;

Y represents a bond or a —$(CH_2)_n$— or —$(CH_2)_r$-Q-(CH—)$_s$— radical,

Q representing a piperazine, piperidine, 1,2,3,6-tetrahydropyridine, azetidine or thiazolidine radical or a saturated carbon ring having 3 to 7 members;

Φ represents a bond or a —$(CH_2)_p$—O—$(CH_2)_q$— radical;

$R_{12}$ represents a hydrogen atom or a linear or branched alkyl or alkoxy radical having 1 to 6 carbon atoms;

$R_{15}$ and $R_{16}$ represent, independently, a hydrogen atom or a linear or branched alkyl radical having 1 to 6 carbon atoms or a —CO—$R_{18}$ radical in which $R_{18}$ represents a linear or branched alkyl or alkoxy radical having 1 to 6 carbon atoms;

m, n, p, q, r and s being integers from 0 to 6.

Among the A radicals which can be used for the invention, the radicals of the type

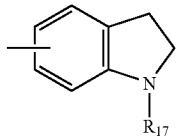

in which $R_{17}$ represents a linear or branched alkyl radical having 1 to 6 carbon atoms, an aminoalkyl, alkylaminoalkyl, dialkylaminoalkyl, arylalkyl, diarylalkyl or bis-arylalkyl radical, and notably those in which $R_{17}$ represents the methyl, benzyl or naphthylmethyl radical will be preferably preferred.

Preferably, the compounds according to the invention are one of the following compounds:

2-hydroxy-5-methoxy-N-2-[4-[(2-thienyl(imino)methyl) amino]phenyl]ethyl}-benzamide;
2-hydroxy-5-methylthio-N-{2-[4-[(2-thienyl (imino)methyl)amino]phenyl]ethyl}-benzamide;
2,5-dihydroxy-N-{2-[4[(2-thienyl(imino)methyl)amino] phenyl]ethyl-benzamide;
2-hydroxy-3-isopropyl-N-{2-[4-[(2-thienyl(imino)methyl) amino]phenyl]ethyl}-benzamide;
2,6-dihydroxy-N-{2-[4-[(2-thienyl(imino)methyl)amino] phenyl]ethyl}-benzamide;
2-hydroxy-4,6-dimethoxy-N-{2-[4-[(2-thienyl(imino)methyl)amino]phenyl]ethyl}-benzamide;
2-hydroxy-4,5,6-trimethoxy-N-{2-[4-[(2-thienyl(imino)methyl)amino]phenyl]ethyl}-benzamide;
2-hydroxy-3,5-di-tert-butyl-N-{2-[4-[(2-thienyl(imino)methyl)amino]phenyl]ethyl-benzamide;
2-hydroxy-3,5-diisopropyl-N-{2-[4-[(2-thienyl(imino)methyl)amino]phenyl]ethyl}-benzamide;
2,4-dihydroxy-3,6-dimethyl-N-{2-[4-[(2-thienyl(imino)methyl)amino]phenyl]ethyl-benzamide;
2,7-dihydroxy-N-{2-[4-[(2-thienyl(imino)methyl)amino] phenyl]ethyl}-2-naphthalenecarboxamide;
2-hydroxy-4-methoxy-N-{2-[4-[(2-thienyl(imino)methyl) amino]phenyl]ethyl}-benzamide;
2-hydroxy-3-isopropyl-5-methoxy-N-{2-[4-[(2-thienyl (imino)methyl)amino]phenyl]ethyl}-benzamide;
N-(2-hydroxy-3-tert-butyl-5-methoxy)-4-{[2-thienyl(imino) methyl]amino}benzene-butanamide;
3,4-dihydro-6-hydroxy-2,5,7,8-tetramethyl-N-{2-[4-[(2-thienyl(imino)methyl)amino]phenyl]ethyl}-2H-1-benzopyran-2-carboxamide;
3,4-dihydro-6-hydroxy-2,5,7,8-tetramethyl-N-{1-[4-[(2-thienyl(imino)methyl)amino]phenyl]methyl}-2H-1-benzopyran-2-carboxamide;
N-(4-hydroxyphenyl)-2-thiophenecarboximidamide;
N-(2-hydroxyphenyl)-2-thiophenecarboximidamide;
N-(3-hydroxyphenyl)-2-thiophenecarboximidamide;
N-(3-hydroxy-4-methoxyphenyl)-2-thiophenecarboximidamide;
N-(3-hydroxy-4-methylphenyl)-2-thiophenecarboximidamide;
N-(4-methoxyphenyl)-2-thiophenecarboximidamide;
N-(3,5-dimethyl-4-hydroxyphenyl)-2-thiophenecarboximidamide;
N-(3,5-dichloro-4-hydroxyphenyl)-2-thiophenecarboximidamide;
N-(3,5-bis-(1,1-dimethylethyl)-4-hydroxyphenyl)-2-thiophenecarboximidamide;
N-{4-[4-[(3,4-dihydro-6-hydroxy-2,5,7,8-tetramethyl-2H-1-benzopyran-2-yl)methyl]1-piperazinyl]phenyl}-2-thiophenecarboximidamide;
1-(2-hydroxy-4,6-dimethoxybenzoyl)-3-{4-[(imino(2-thienyl)methyl)amino]phenoxy}azetidine;
N-(2-hydroxy-5-methoxy)-4-{[2-thienyl(imino)methyl] amino}benzene-butanamide;
N-(2-hydroxy-5-methoxy)-4-{[2-thienyl(imino)methyl] amino}benzene-propanamide;
tert-butyl 2-{[(4-{[amino(2-thienyl)methylidene] amino}phenethyl)amino]-carbonyl}-4-methoxyphenyl-carbamate
2-amino-N-(4-{[amino(2-thienyl)methylidene] amino}phenethyl)-5-methoxybenzamide;
5-amino-N-(4-{[amino(2-thienyl)methylidene] amino}phenethyl)-2-hydroxybenzamide;
N-(4-{[amino(2-thienyl)methylidene]amino}phenethyl)-2-hydroxy-5-methoxy-3-methylbenzamide;
N-[2-(4-{[amino(2-thienyl)methylidene]amino}anilino)-2-oxoethyl]-3,5-di(tert-butyl)-4-hydroxybenzamide;
N'-{4-[4-(1,2,3,4-tetrahydro-2-naphthalenylcarbonyl)-1-piperazinyl]phenyl}-2-thiophenecarboximidamide;
4-(4-{[amino(2-thienyl)methylidene]amino}phenyl)-N-{4-[(methylsulphonyl)amino]phenyl}butanamide;
4-(4-{[amino(2-thienyl)methylidene]amino}phenyl)-N-[4-(dimethylamino)phenyl]butanamide;
5-(4-{[amino(2-thienyl)methylidene]amino}phenyl)-N-[4-dimethylamino)phenyl]pentanamide;
(E)-N-(4-{[amino(2-thienyl)methylidene] amino}phenethyl)-3-(2-hydroxyphenyl)-2-propenamide;
(E)-N-(4-{[amino(2-thienyl)methylidene] amino}phenethyl)-3-(4-hydroxyphenyl)-2-propenamide;
(E)-N-(4-{[amino(2-thienyl)methylidene] amino}phenethyl)-3-(3,4-dihydroxyphenyl)-2-propenamide;
(E)-N-(4-{[amino(2-thienyl)methylidene] amino}phenethyl)-3-(4-hydroxy-3,5-dimethoxyphenyl)-2-propenamide;
(4R)-2-(3-{[amino(2-thienyl)methylidene]amino)-phenyl)-N-[4-(dimethylamino)phenyl]-1,3-thiazolidine-4-carboxamide;
N'-[4-(4-42-[3,5-di(tert-butyl)-4-hydroxy-phenoxy]acetyl}-1-piperazinyl)phenyl]-2-thiophenecarboximidamide;
N-{4-[4-(2-{[3,5-di(tert-butyl)-4-hydroxyphenyl] thio}acetyl)-1-piperazinyl]phenyl}-2-thiophenecarboximidamide;
N'-(4-{4-[2-(4-hydroxy-2,3,5,6-tetramethylphenoxy)-acetyl]-1-piperazinyl}phenyl)-2-thiophenecarboximidamide;
N-(4-{[amino(2-thienyl)methylidene]amino}-phenethyl)-2-[3,5-di(tert-butyl)-4-hydroxyphenoxy]acetamide;
N-{4-[2-({2-[3,5-di(tert-butyl)-4-hydroxyphenoxy]-ethyl}amino)ethyl]phenyl}-2-thiophenecarboximidamide;
tert-butyl 3-{[amino(2-thienyl)methylidene]amino)benzyl {3-[4-(dimethylamino)anilino]-3-oxopropyl}carbamate;
3-[(3-{[amino(2-thienyl)methylidene]amino}-benzyl) amino]-N-[4-(dimethylamino)phenyl]propanamide;
3-[(3-{[amino(2-thienyl)methylidene]amino}-benzyl) amino]-N-[3,5-di(tert-butyl)-4-hydroxyphenyl]propanamide;
3-[(3-{[amino(2-thienyl)methylidene]amino}-benzyl) amino]-N-[4-(4-methyl-1-piperazinyl)phenyl]propanamide;

3-[(3-{[amino(2-thienyl)methylidene]amino)-benzyl)
    amino]-N-[4-(4-morpholinyl)phenyl]propanamide;
3-[(3-{[amino(2-thienyl)methylidene]amino}-benzyl)
    amino]-N-(1-methyl-2,3-dihydro-1H-indol-5-yl)propana-
    mide;
3-[(3-{[amino(2-thienyl)methylidene]amino}-benzyl)
    amino]-N-(1-benzyl-2,3-dihydro-1H-indol-5-yl)propana-
    mide;
3-[(3-{[amino(2-thienyl)methylidene]amino}benzyl)
    amino]-N-[1-(1-naphthylmethyl)-2,3-dihydro-1H-indol-
    5-yl]propanamide;
N'-[4-(2-{[5-(dimethylamino)-2-hydroxybenzyl]
    amino}ethyl)phenyl]-2-thiophenecarboximidamide;
N-(4-{[(4-{[amino(2-thienyl)methylidene]
    amino}phenethyl)-amino]methyl}phenyl)acetamide;
N'-[4-(2-[(8-hydroxy-2-quinolinyl)methyl]amino}ethyl)
    phenyl]-2-thiophenecarboximidamide;
N'-[4-(2-{[3-phenyl-2-propenyl]amino}ethyl)phenyl]-2-
    thiophenecarboximidamide;
N'-[4-(2-{[3-(4-hydroxy-3-methoxyphenyl)-2-propenyl]
    amino}ethyl)phenyl]-2-thiophenecarboximidamide;
N'-[4-(2-([3-(4-hydroxy-3,5-dimethoxyphenyl)-2-propenyl]
    amino}ethyl)phenyl]-2-thiophenecarboximidamide;
N'-[4-(2-{[5-(dimethylamino)-2-hydroxy-3-methoxyben-
    zyl]amino}-ethyl)phenyl]-2-thiophenecarboximidamide;
N'-(4-{2-[(2-hydroxy-4,6-dimethoxybenzyl)amino]
    ethyl}phenyl)-2-thiophenecarboximidamide;
N'-[4-(2-{[(6-hydroxy-2,5,7,8-tetramethyl-3,4-dihydro-2H-
    chromen-2-yl)methyl]amino}ethyl)phenyl]-2-thiophen-
    ecarboximidamide;
N'-(4-{2-[[(E)-3-(4-hydroxy-3,5-dimethoxyphenyl)-2-pro-
    penyl](methyl)amino]ethyl}phenyl)-2-thiophenecarbox-
    imidamide
4-{[(4-{[amino(2-thienyl)methylidene]amino}phenethyl)-
    amino]methyl}-1-pyridiniumolate;
N'-[4-(2-{[(2-hydroxy-4,6-dimethoxyphenyl)methylidene]-
    amino}ethyl)phenyl]-2-thiophenecarboximidamide;
tert-butyl 4-{[amino(2-thienyl)methylidene]
    amino}phenethyl(2-hydroxy-4,6-dimethoxybenzyl)car-
    bamate;
N'-{4-[4-phenyl-3,6-dihydro-1 (2H)-pyridinyl]phenyl}-2-
    thiophenecarboximidamide;
N'-(4-{2-[4-phenyl-3,6-dihydro-1(2H)-pyridinyl]
    ethyl}phenyl)-2-thiophenecarboximidamide;
N'-{4-[(1-benzhydryl-3-azetidinyl)oxy]phenyl}-2-
    thiophene-carboximidamide;
N'-[4-(2-quinolinylmethoxy)phenyl]-2-thiophene-carbox-
    imidamide;
N'-(4-{4-[2-hydroxy-2-methyl-4-(2,4,5-trimethyl-3,6-di-
    oxo-1,4-cyclohexadien-1-yl)butanoyl]-1-
    piperazinyl}phenyl)-2-thiophene-carboximidamide;
N-{4-[2-(1,3-dimethyl-2,6-dioxo-1,2,3,6-tetrahydro-7H-pu-
    rin-7-yl)ethyl]phenyl}-2-thiophenecarboximidamide;
N'-(4-{4-[2,6-di(1-pyrrolidinyl)-4-pyrimidinyl]-1-
    piperazinyl}phenyl)-2-thiophenecarboximidamide;
N'-{4-[2-({[4-(dimethylamino)anilino]carbonyl}amino)-
    ethyl]phenyl}-2-thiophenecarboximidamide;
N-{[1-(4-{[amino(2-thienyl)methylidene]-amino}phenyl)-
    cyclobutyl]methyl}-6-hydroxy-2,5,7,8-tetramethyl-2-
    chromanecarboxamide;
N'-{4-[4-(5-methoxy-1H-indol-3-yl)-1-piperidinyl]-phe-
    nyl}-2-thiophenecarboximidamide
N'-(4-{2-[[5-(dimethylamino)-2-hydroxy-3-methoxyben-
    zyl]-(methyl)amino]ethyl}phenyl)-2-thiophenecarbox-
    imidamide 4-(4-{[amino(2-thienyl)methylidene]amino}phenyl)-N-{1-
    [3-(dimethylamino)propyl]-2,3-dihydro-1H-indol-5-
    yl}butanamide;
3-[(5-{[amino(2-thienyl)methylidene]amino}-2-methoxy-
    benzyl)amino]-N-[1-(1-naphthylmethyl)-2,3-dihydro-
    1H-indol-5-yl]propanamide;

or a salt of the latter.

More preferentially, the compounds according to the invention are one of the following compounds:

2-hydroxy-5-methoxy-N-{2-[4-[(2-thienyl(imino)methyl)
    amino]phenyl]ethyl}-benzamide;
2,5-dihydroxy-N-{2-[4[(2-thienyl(imino)methyl)amino]
    phenyl]ethyl-benzamide;
2-hydroxy-4,6-dimethoxy-N-{2-[4-[(2-thienyl(imino)me-
    thyl)amino]phenyl]ethyl}-benzamide;
N-(2-hydroxy-3-tert-butyl-5-methoxy)-4-{[2-thienyl(imino)
    methyl]amino}benzene-butanamide;
3,4-dihydro-6-hydroxy-2,5,7,8-tetramethyl-N-{2-[4-[(2-
    thienyl(imino)methyl)amino]phenyl]ethyl}-2H-1-ben-
    zopyran-2-carboxamide;
3,4-dihydro-6-hydroxy-2,5,7,8-tetramethyl-N-{1-[4-[(2-
    thienyl(imino)methyl)amino]phenyl]methyl}-2H-1-ben-
    zopyran-2-carboxamide;
N-(2-hydroxy-5-methoxy)-4-{[2-thienyl(imino)methyl]
    amino}benzene-propanamide;
5-amino-N-(4-{[amino(2-thienyl)methylidene]
    amino}phenethyl)-2-hydroxybenzamide;
5-(4-{[amino(2-thienyl)methylidene]amino}phenyl)-N-[4-
    (dimethylamino)phenyl]pentanamide;
(E)-N-(4-{[amino(2-thienyl)methylidene]
    amino}phenethyl)-3-(2-hydroxyphenyl)-2-propenamide;
(E)-N-(4-{[amino(2-thienyl)methylidene]
    amino}phenethyl)-3-(4-hydroxyphenyl)-2-propenamide;
(E)-N-(4-{[amino(2-thienyl)methylidene]
    amino}phenethyl)-3-(3,4-dihydroxyphenyl)-2-propena-
    mide;
(E)-N-(4-{[amino(2-thienyl)methylidene]
    amino}phenethyl)-3-(4-hydroxy-3,5-dimethoxyphenyl)-
    2-propenamide;
N-{4-[2-({2-[3,5-di(tert-butyl)-4-hydroxyphenoxy]-
    ethyl}amino)ethyl]phenyl}-2-thiophenecarboximida-
    mide;
3-[(3-{[amino(2-thienyl)methylidene]amino}-benzyl)
    amino]-N-[4-(dimethylamino)phenyl]propanamide;
3-[(3-{[amino(2-thienyl)methylidene]amino}-benzyl)
    amino]-N-[3,5-di(tert-butyl)-4-hydroxyphenyl]propana-
    mide;
3-[(3-{[amino(2-thienyl)methylidene]amino}-benzyl)
    amino]-N-[4-(4-methyl-1piperazinyl)phenyl]propana-
    mide;
3-[(3-{[amino(2-thienyl)methylidene]amino}-benzyl)
    amino]-N-[4-(4-morpholinyl)phenyl]propanamide;
3-[(3-{[amino(2-thienyl)methylidene]amino}-benzyl)
    amino]-N-(1-methyl-2,3-dihydro-1H-indol-5-yl)propana-
    mide;
3-[(3-{[amino(2-thienyl)methylidene]amino}-benzyl)
    amino]-N-(1-benzyl-2,3-dihydro-1H-indol-5-yl)propana-
    mide;
3-[(3-{[amino(2-thienyl)methylidene]amino}benzyl)
    amino]-N-[1-(1-naphthylmethyl)-2,3-dihydro-1H-indol-
    5-yl]propanamide;
N'-[4-(2-{[5-(dimethylamino)-2-hydroxybenzyl]
    amino}ethyl)phenyl]-2-thiophenecarboximidamide;
N-(4-{[(4-{[amino(2-thienyl)methylidene]
    amino}phenethyl)-amino]methyl}phenyl)acetamide;

N'-[4-(2-{[(8-hydroxy-2-quinolinyl)methyl]amino}ethyl)
  phenyl]-2-thiophenecarboximidamide;
N'-[4-(2-{[3-phenyl-2-propenyl]amino}ethyl)phenyl]-2-
  thiophenecarboximidamide;
N'-[4-(2-{[3-(4-hydroxy-3-methoxyphenyl)-2-propenyl]
  amino}ethyl)phenyl]-2-thiophenecarboximidamide;
N'-[4-(2-{[3-(4-hydroxy-3,5-dimethoxyphenyl)-2-propenyl]
  amino}ethyl)phenyl]-2-thiophenecarboximidamide;
N'-[4-(2-{[(6-hydroxy-2,5,7,8-tetramethyl-3,4-dihydro-2H-
  chromen-2-yl)methyl]amino}ethyl)phenyl]-2-thiophen-
  ecarboximidamide;
N'-(4-{2-[[(E)-3-(4-hydroxy-3,5-dimethoxyphenyl)-2-pro-
  penyl](methyl)amino]ethyl}phenyl)-2-thiophenecarbox-
  imidamide;
N'-(4-{2-[4-phenyl-3,6-dihydro-1(2H)-pyridinyl]
  ethyl}phenyl)-2-thiophenecarboximidamide;
N'-{4-[2-({[4-(dimethylamino)anilino]carbonyl}amino)-
  ethyl]phenyl}-2-thiophenecarboximidamide;
N-{[1-(4-{[amino(2-thienyl)methylidene]-amino}phenyl)-
  cyclobutyl]methyl}-6-hydroxy-2,5,7,8-tetramethyl-2-
  chromanecarboxamide;

or the salts of the latter.

Also more preferentially, the compounds according to the invention are one of the following compounds:
2-hydroxy-5-methoxy-N-{2-[4-[(2-thienyl(imino)methyl)
  amino]phenyl]ethyl}-benzamide;
2,5-dihydroxy-N-2-[4[(2-thienyl(imino)methyl)amino]phe-
  nyl]ethyl-benzamide;
N-(2-hydroxy-5-methoxy)-4-{[2-thienyl(imino)methyl]
  amino}benzene-propanamide;
5-amino-N-(4-{[amino(2-thienyl)methylidene]
  amino}phenethyl)-2-hydroxybenzamide;
5-(4-{[amino(2-thienyl)methylidene]amino}phenyl)-N-[4-
  (dimethylamino)phenyl]pentanamide;
(E)-N-(4-{[amino(2-thienyl)methylidene]
  amino}phenethyl)-3-(2-hydroxyphenyl)-2-propenamide;
(E)-N-(4-{[amino(2-thienyl)methylidene]
  amino}phenethyl)-3-(3,4-dihydroxyphenyl)-2-propena-
  mide;
(E)-N-(4-{[amino(2-thienyl)methylidene]
  amino}phenethyl)-3-(4-hydroxy-3,5-dimethoxyphenyl)-
  2-propenamide;
N-{4-[2-({2-[3,5-di(tert-butyl)-4-hydroxyphenoxy]-
  ethyl}amino)ethyl]phenyl}-2-thiophenecarboximida-
  mide;
3-[(3-{[amino(2-thienyl)methylidene]amino}-benzyl)
  amino]-N-[4-(dimethylamino)phenyl]propanamide;
3-[(3-{[amino(2-thienyl)methylidene]amino}-benzyl)
  amino]-N-[3,5-di(tert-butyl)-4-hydroxyphenyl]propana-
  mide;
3-[(3-{([amino(2-thienyl)methylidene]amino}-benzyl)
  amino]-N-(1-methyl-2,3-dihydro-1H-indol-5-yl)propana-
  mide;
3-[(3-{[amino(2-thienyl)methylidene]amino}-benzyl)
  amino]-N-(1-benzyl-2,3-dihydro-1H-indol-5-yl)propana-
  mide;
3-[(3-{[amino(2-thienyl)methylidene]amino}benzyl)
  amino]-N-[1-(1-naphthylmethyl)-2,3-dihydro-1H-indol-
  5-yl]propanamide;
N'-[4-(2-{[5-(dimethylamino)-2-hydroxybenzyl]
  amino}ethyl)phenyl]-2-thiophenecarboximidamide;
N'-[4-(2-{[(8-hydroxy-2-quinolinyl)methyl]amino}ethyl)
  phenyl]-2-thiophenecarboximidamide;
N'-[4-(2-{[3-(4-hydroxy-3-methoxyphenyl)-2-propenyl]
  amino}ethyl)phenyl]-2-thiophenecarboximidamide;
N'-[4-(2-{[3-(4-hydroxy-3,5-dimethoxyphenyl)-2-propenyl]
  amino}ethyl)phenyl]-2-thiophenecarboximidamide;
N'-[4-(2-{[(6-hydroxy-2,5,7,8-tetramethyl-3,4-dihydro-2H-
  chromen-2-yl)methyl]amino}ethyl)phenyl]-2-thiophen-
  ecarboximidamide;
N'-(4-{2-[[(E)-3-(4-hydroxy-3,5-dimethoxyphenyl)-2-pro-
  penyl](methyl)amino]ethyl}phenyl)-2-thiophenecarbox-
  imidamide;
N'-(4-{2-[4-phenyl-3,6-dihydro-1(2H)-pyridinyl]
  ethyl}phenyl)-2-thiophenecarboximidamide;

or the salts of the latter.

Finally, the following compounds will be also more particularly preferred:
N-(2-hydroxy-5-methoxy)-4-{[2-thienyl(imino)methyl]
  amino}benzene-propanamide;
N-{4-[2-({2-[3,5-di(tert-butyl)-4-hydroxyphenoxy]-
  ethyl}amino)ethyl]phenyl}-2-thiophenecarboximida-
  mide;
3-[(3-{[amino(2-thienyl)methylidene]amino}-benzyl)
  amino]-N-[4-(dimethylamino)phenyl]propanamide;
3-[(3-{[amino(2-thienyl)methylidene]amino}-benzyl)
  amino]-N-[3,5-di(tert-butyl)-4-hydroxyphenyl]propana-
  mide;
3-[(3-{[amino(2-thienyl)methylidene]amino}-benzyl)
  amino]-N-(1-methyl-2,3-dihydro-1H-indol-5-yl)propana-
  mide;
3-[(3-{[amino(2-thienyl)methylidene]amino}-benzyl)
  amino]-N-(1-benzyl-2,3-dihydro-1H-indol-5-yl)propana-
  mide;
3-[(3-{[amino(2-thienyl)methylidene]amino}benzyl)
  amino]-N-[1-(1-naphthylmethyl)-2,3-dihydro-1H-indol-
  5-yl]propanamide;
N'-[4-(2-{[5-(dimethylamino)-2-hydroxybenzyl]
  amino}ethyl)phenyl]-2-thiophenecarboximidamide;
N'-[4-(2-{[3-(4-hydroxy-3-methoxyphenyl)-2-propenyl]
  amino}ethyl)phenyl]-2-thiophenecarboximidamide;
N'-[4-(2-{[3-(4-hydroxy-3,5-dimethoxyphenyl)-2-propenyl]
  amino}ethyl)phenyl]-2-thiophenecarboximidamide;
N'-[4-(2-{[(6-hydroxy-2,5,7,8-tetramethyl-3,4-dihydro-2H-
  chromen-2-yl)methyl]amino}ethyl)phenyl]-2-thiophen-
  ecarboximidamide;
N'-(4-{2-[[(E)-3-(4-hydroxy-3,5-dimethoxyphenyl)-2-pro-
  penyl](methyl)amino]ethyl}phenyl)-2-thiophenecarbox-
  imidamide;

or the salts of the latter.

In certain cases, the compounds according to the present invention can comprise asymmetrical carbon atoms. As a result, the compounds according to the present invention have two possible enantiomeric forms, i.e. the "R" and "S" configurations. The present invention includes the two enantiomeric forms and all combinations of these forms, including the "RS" racemic mixtures. In an effort to simplify matters, when no specific configuration is indicated in the structural formulae, it should be understood that the two enantiomeric forms and their mixtures are represented.

The invention furthermore offers, as new industrial products, the compounds of general formula (IS), which are useful synthesis intermediates in the preparation of products of general formula (I),

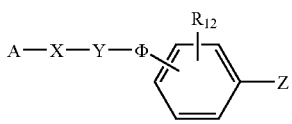

general formula (IS) in which
A represents:
either a

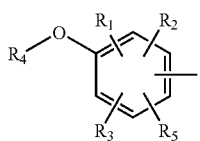

radical in which $R_1$, $R_2$ and $R_3$ represent, independently, a halogen, the OH or $SR_6$ group or a linear or branched alkyl, alkenyl or alkoxy radical having 1 to 6 carbon atoms, or a $NR_7RS$ radical, $R_4$ representing a hydrogen atom or a linear or branched alkyl radical having 1 to 6 carbon atoms, $R_5$ represents a hydrogen atom, the OH or SR group or a linear or branched alkyl or alkoxy radical having 1 to 6 carbon atoms, $R_6$ representing a hydrogen atom or a linear or branched alkyl radical having 1 to 6 carbon atoms, $R_7$ and $R_8$ independently representing a hydrogen atom, an OH group, a linear or branched alkyl radical having 1 to 6 carbon atoms or a —CO—$R_9$ radical in which $R_9$ represents a linear or branched alkyl radical having 1 to 6 carbon atoms;

or a

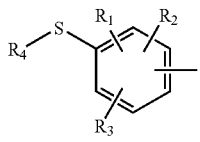

radical in which $R_1$, $R_2$ and $R_3$ represent, independently, a hydrogen atom, the OH or $SR_6$ group, a halogen or a linear or branched alkyl, alkenyl or alkoxy radical having 1 to 6 carbon atoms, or a $NR_7R_8$ radical, $R_4$ represents a hydrogen atom or a linear or branched alkyl radical having 1 to 6 carbon atoms, $R_6$ representing a hydrogen atom or a linear or branched alkyl radical having 1 to 6 carbon atoms, $R_7$ and $R_8$ independently representing a hydrogen atom, an OH group, a linear or branched alkyl radical having 1 to 6 carbon atoms or a —CO—$R_9$ radical in which $R_9$ represents a linear or branched alkyl radical having 1 to 6 carbon atoms;

or a

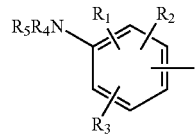

radical in which $R_1$, $R_2$ and $R_3$ represent, independently, a hydrogen atom, a halogen, the OH or $SR_6$ group, a linear or branched alkyl, alkenyl or alkoxy radical having 1 to 6 carbon atoms, or an $NR_7RS$ radical, $R_4$ and $R_5$ independently represent a hydrogen atom or a linear or branched alkyl radical having 1 to 6 carbon atoms, or $R_4$ and $R_5$ form together with the nitrogen atom an optionally substituted heterocycle having 4 to 7 members and 1 to 3 heteroatoms including the nitrogen atom already present, the additional heteroatoms being chosen independently from the group constituted by the O, N and S atoms, or also $R_4$ represents an alkylsulphonyl, alkylsulphoxide or alkylcarbonyl radical and $R_5$ represents H, $R_6$ representing a hydrogen atom or a linear or branched alkyl radical having 1 to 6 carbon atoms, $R_7$ and $R_8$ independently representing a hydrogen atom, an OH group, a linear or branched alkyl radical having 1 to 6 carbon atoms or a —CO—$R_9$ radical in which $R_9$ represents a linear or branched alkyl radical having 1 to 6 carbon atoms;

or a

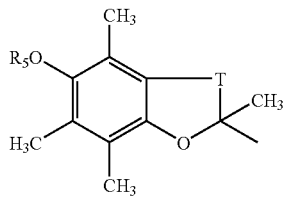

radical in which T represents a —$(CH_2)_k$— radical, k representing 1 or 2, and $R_5$ represents a hydrogen atom or a linear or branched alkyl radical having 1 to 6 carbon atoms or a

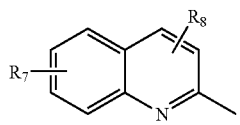

radical in which $R_7$ and $R_5$ represent, independently, a hydrogen atom or an OH group, or a

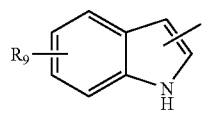

radical in which $R_9$ represents a hydrogen atom, the OH group or a linear or branched alkyl or alkoxy radical having 1 to 6 carbon atoms, or a

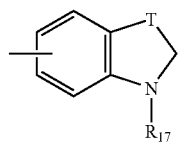

radical in which T represents a —(CH$_2$)$_k$— radical, k representing 1 or 2, and R$_{17}$ represents a linear or branched alkyl radical having 1 to 6 carbon atoms, or an arylalkyl, diarylalkyl, bis-arylalkyl, aminoalkyl, alkylaminoalkyl or dialkylaminoalkyl radical, or R$_{17}$ also represents an (heterocyclo)alkyl radical in which the heterocycle is saturated or unsaturated, has 3 to 7 members and includes at least one nitrogen atom, said nitrogen atom being optionally substituted by a hydrogen atom or an alkyl radical,
or a

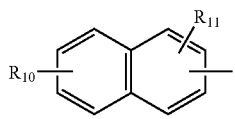

radical in which R$_{10}$ and R$_{11}$ represent, independently, a hydrogen atom or an OH group,
or finally one of the

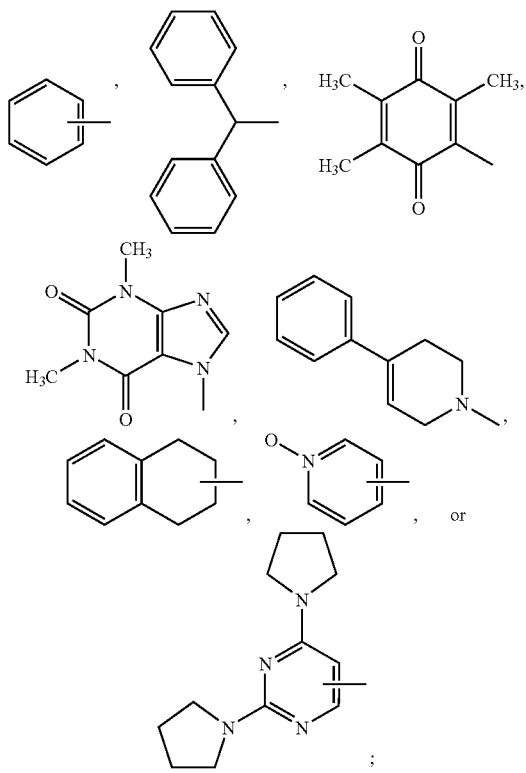

radicals,
B represents a linear or branched alkyl radical having 1 to 6 carbon atoms, carbocyclic or heterocyclic aryl with 5 or 6 members containing from 1 to 4 heteroatoms chosen from O, S, N and in particular the thiophene, furan, pyrrole or thiazole radicals, the aryl radical being optionally substituted by one or more groups chosen from the linear or branched alkyl alkenyl or alkoxy radicals having 1 to 6 carbon atoms, or also B represents an NR$_{13}$R$_{14}$ radical, in which R$_{13}$ and R$_{14}$ represent, independently, a hydrogen atom or a linear or branched alkyl radical having 1 to 6 carbon atoms, or R$_{13}$ and R$_{14}$ form together with the nitrogen atom a non aromatic heterocycle with five to six members, the elements of the chain being chosen from a group comprising —CH$_2$—, —NH—, —O— or —S—;

X represents a bond or a —(CH$_2$)$_m$—, —O—(CH$_2$)$_m$—, S—(CH$_2$)$_m$—, —NR$_{15}$—(CH$_2$)$_m$—, —CO—NR$_{15}$—, —O—(CH$_2$)$_m$—CO—, —S—(CH$_2$)$_m$—CO—, —NR$_{15}$—(CH$_2$)$_m$—CO—, —(CH$_2$)$_m$—C(OH)(CH$_3$)—CO—, —CH=CH— or —CH=N— radical;

Y represents a bond or a —(CH$_2$)$_n$— or —(CH$_2$)$_r$-Q-(CH$_2$)$_s$— radical, Q representing a piperazine, homopiperazine, 2-methylpiperazine, 2,5-dimethylpiperazine, piperidine, 1,2,3,6-tetrahydropyridine, pyrrolidine, azetidine or thiazolidine radical or a saturated carbon ring having 3 to 7 members;

Φ represents a bond or a —(CH$_2$)$_p$—O—(CH$_2$)$_q$—, —(CH$_2$)$_p$—S—(CH$_2$)$_q$—, —(CH$_2$)$_p$—NR$_{16}$—(CH$_2$)$_q$—, —(CH$_2$)$_p$—CO—NR$_{16}$—(CH$_2$)$_q$ or —CO—(CH$_2$)$_p$—NR$_{16}$—(CH$_2$)$_q$— radical;

Z represents NO$_2$ or N—H$_2$;

R$_{12}$ represents a hydrogen atom or a linear or branched alkyl or alkoxy radical having 1 to 6 carbon atoms;

R$_{15}$ and R$_{16}$ represent, independently, a hydrogen atom or a linear or branched alkyl radical having 1 to 6 carbon atoms or a —CO—R$_{18}$ radical in which R$_{18}$ represents a linear or branched alkyl or alkoxy radical having 1 to 6 carbon atoms;

m, n, p, q, r and s being integers from 0 to 6;
it being understood that:
if A represents the

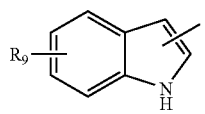

radical then Y represents the piperidine radical;
if A represents the

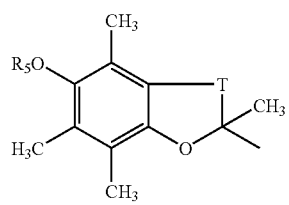

radical then Y represents a —(CH$_2$)$_r$-Q-(CH$_2$)$_s$— radical in which Q represents a saturated carbon ring having 3 to 7 members;

and if A represents the

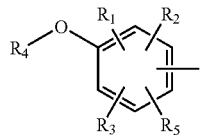

radical with at least two of the $R_1$, $R_2$, $R_3$ and $R_5$ radicals representing H, then X represents a —CH=CH— or —CH=N— radical and the X—Y-Φ- group does not represent a —CH=CH—CO-ω- radical in which ω represents any radical.

The invention further relates to the compounds of general formula (IS'), which are synthesis intermediates in the preparation of products of general formula (I) in which A is an substituted indoline radical as defined previously, X represents the —$NR_5$—CO— radical, Y represents a bond and Φ represents a —$(CH_2)_p$—$NR_{16}$—$(CH_2)_q$— radical,

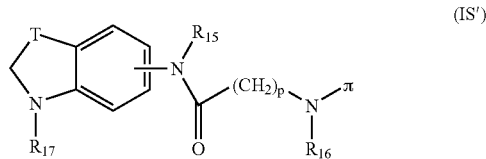

general formula (IS') in which
π represents a hydrogen atom or a protective group of carbamate type;
$R_{15}$ and $R_{16}$ represent, independently, a hydrogen atom, a linear or branched alkyl radical having 1 to 6 carbon atoms or a —CO—$R_{18}$ radical in which $R_{18}$ represents ua linear or branched alkyl or alkoxy radical having 1 to 6 carbon atoms
T represents a —$(CH_2)_k$— radical, k representing 1 or 2;
$R_{17}$ represents a linear or branched alkyl radical having 1 to 6 carbon atoms, arylalkyl, diarylalkyl, bis-arylalkyl, aminoalkyl, alkylaminoalkyl or dialkylaminoalkyl, or $R_{17}$ also represents a (heterocyclo)alkyl radical in which the heterocycle is saturated or unsaturated, has 3 to 7 members and includes at least one nitrogen atom, said nitrogen atom being optionally substituted by a hydrogen atom or an alkyl radical;
and p is an integer from 0 to 6.

A subject of the invention is also, as medicaments, the compounds of general formula (I) described previously or their pharmaceutically acceptable salts. It also relates to pharmaceutical compositions containing these compounds or their pharmaceutically acceptable salts, and the use of these compounds or of their pharmaceutically acceptable salts for producing medicaments intended to inhibit neuronal NO synthase or the inductible NO synthase, to inhibit lipidic peroxidation or to provide the double function of NO synthase inhibition and lipidic peroxidation inhibition function.

By pharmaceutically acceptable salt, is understood in particular addition salts of inorganic acids such as hydrochloride, hydrobromide, hydroiodide, sulphate, phosphate, diphosphate and nitrate or of organic acids such as acetate, maleate, fumarate, tartrate, succinate, citrate, lactate, methanesulphonate, p-toluenesulphonate, pamoate, oxalate and stearate. The salts formed from bases such as sodium or potassium hydroxide also fall within the scope of the present invention, when they can be used. For other examples of pharmaceutically acceptable salts, reference can be made to "Pharmaceutical salts", J. Pharm. Sci. 66:1 (1977).

The pharmaceutical composition can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or glycols, as well as their mixtures, in varying proportions, in water.

The administration of a medicament according to the invention can be carried out by topical, oral, parenteral route, by intramuscular injection, etc.

The envisaged administration dose for a medicament according to the invention is comprised between 0.1 mg and 10 g according to the type of active compound used.

In accordance with the invention, the compounds of general formula (I) can be prepared by the process described below.

Preparation of the Compounds of the Invention

The compounds of the invention corresponding to general formula (I) but not to the general formula (I') can be prepared according to the procedures described in the examples. The products of general formula (I') are prepared as described hereafter.

Preparation of Compounds of General Formula (I'):

The compounds of general formula (I') can be prepared from intermediates of general formula (II) according to Diagram 1 where A, B, X, Y, Φ and $R_{12}$ are as defined above and Gp is a protective group of carbamate type, for example the t-butoxycarbonyl group.

Diagram 1

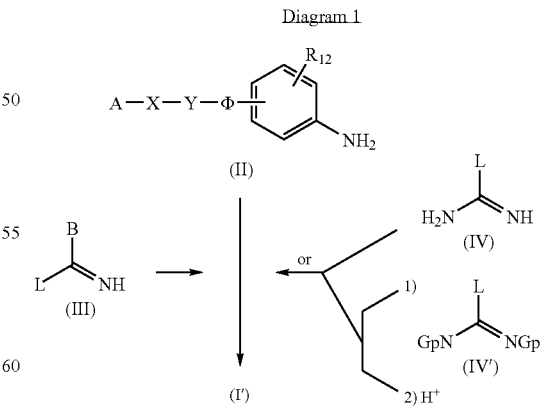

The aniline derivatives of general formula (II) can be condensed with compounds of general formula (III), in which L represents a parting group (for example an alkoxy, alkylthio, aralkylthio, sulphonic acid, halide, aryl alcohol or tosyl radical), in order to produce the final compounds of general formula (I') of substituted amidine type (cf. Diagram 1). For example, for B=thiophene, the derivatives of general formula (II) can be condensed with of S-methylthiophene thiocarboxamide hydroiodide, prepared according to a method in the literature (*Ann. Chim.* (1962), 7, 303-337). Condensation can be carried out by heating in an alcohol (for example in methanol or isopropanol), optionally in the presence of DMF at a temperature preferably comprised between 50 and 100° C. for a duration generally comprised between a few hours and overnight.

In the particular case where A represents a pyridine-oxide, the pyridine oxidation is only carried out during the last synthesis stage because of the fragility of these compounds in reducing medium. Metachloroperbenzoic acid, used as oxidizing agent, allows pyridine-oxide derivatives of general formula (I') to be obtained.

Salification of the compounds of general formula (I'), when carried out in the presence of a strong acid such as, for example, hydrochloric acid, allows the amines which have been protected in the form of tert-butylcarbamate during the synthesis to be released simultaneously.

In the case where B is an amine, the final compounds of general formula (I') are guanidines. These can be prepared, for example, by condensation of the amines of general formula (II) with the derivatives of general formula (IV) or (IV'). The reagents of general formula (IV) in which L represents, for example, a pyrazole ring are condensed with the amines of general formula (II) according to the conditions described in the literature (*J. Org. Chem.* (1992) 57, 2497-2502), similarly for the reagents of general formula (IV') in which L represents, for example, a pyrazole ring and Gp represents the tBuOCO group (*Tetrahedron Lett.* (1993) 34 (21), 3389-3392) or when L represents the —N—SO₂—CF₃ group and Gp represents the tBuOCO group (*J. Org. Chem.* (1998) 63, 3804-3805). During the final stage of the synthesis, deprotection of the guanidine function is carried out in the presence of a strong acid such as for example trifluoroacetic acid.

Therefore, a subject of the invention is also a process for the preparation of compounds of general formula (I') as defined above, said process being characterized in that a compound of general formula (II)

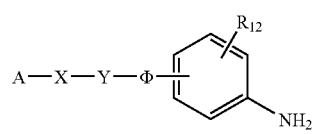

in which A, B, X, Y, Φ and $R_{12}$ are as defined above, is reacted with the intermediate of general formula (III)

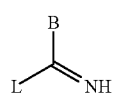

in which B is as defined above and L represents a parting group, for example an alkoxy, alkylthio, aralkylthio, sulphonic acid, halide, aryl alcohol or tosyl radical.

Therefore, a subject of the invention is also a process for the preparation of compounds of general formula (I') as defined above and in which B represents an amine, said process being characterized in that a compound of general formula (II)

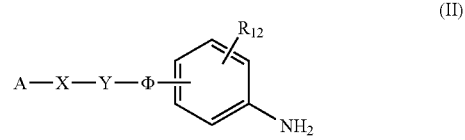

in which A, B, X, Y, Φ and $R_{12}$ are as defined above, is reacted a) either with the intermediate of general formula (IV)

in which L represents a parting group, for example an alkoxy, alkylthio, aralkylthio, sulphonic acid, halide, aryl alcohol or tosyl radical, b) or with the intermediate of general formula (IV')

in which L represents a parting group, for example an alkoxy, alkylthio, aralkylthio, sulphonic acid, halide, aryl alcohol or tosyl radical, and Gp is a protective group of carbamate type, for example the t-butoxycarbonyl group, this reaction being followed, in the case where the reaction with the compound of general formula (IV') is chosen, by hydrolysis in the presence of a strong acid, for example trifluoroacetic acid.

Specific Case Where A Represents a 2,3,5-trimethyl-benzoquinone:

The compounds of general formula (I') in which A represents a 2,3,5-trimethyl-benzoquinone and X=—(CH₂)ₘ—C(OH)(CH₃)—CO— with B, Y, Φ and $R_{12}$ as defined above can be obtained from the compounds comprising a Trolox group, Diagram 1'. The reactivity of the Trolox with respect to the free radicals allows a chemical modification of this group to be envisaged, in fact, the action of FeCl₃ in an aqueous medium (*Helv. Chim. Acta* (1963) 46, 333) causes a radicular opening of the benzopyranic system and leads to the compounds of general formula (I').

Diagram 1'

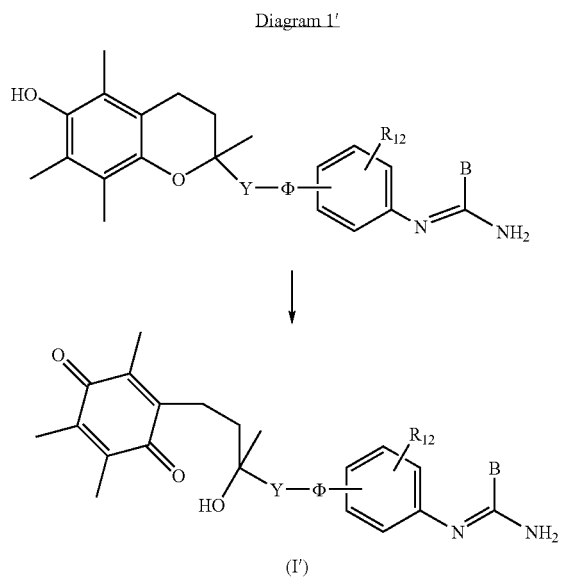

(I')

Preparation of Compounds of General Formula (II):

The non-commercial intermediates of general formula (II), are obtained either by detachment of a protective group, or by reduction of a precursor of nitro type, as illustrated in the synthesis diagrams below.

Reduction of the Precursors of Nitro Type:

The reduction of the nitro function of the intermediates of general formula (V), Diagram 2, in which A, X, Y, Φ and $R_{12}$ are as defined above, is generally carried out by catalytic hydrogenation, in ethanol, in the presence of Pd/C, except in the case of molecules sensitive to these conditions where the nitro group is selectively reduced, for example, by heating the product in an appropriate solvent such as ethyl acetate with a little ethanol in the presence of $SnCl_2$ (*J. Heterocyclic Chem.* (1987), 24, 927-930; *Tetrahedron Letters* (1984), 25 (8), 839-842) or using $NaBH_4$—$BiCl_3$ (*Synth. Con.* (1995) 25 (23), 3799-3803) in a solvent such as ethanol, or then by using Raney Ni with hydrazine hydrate added (*Monatshefte für Chemie*, (1995), 126, 725-732), or also using $SnCl_2$ in the presence of Zn (*Synthesis* (1996), (9), 1076-1078).

Diagram 2

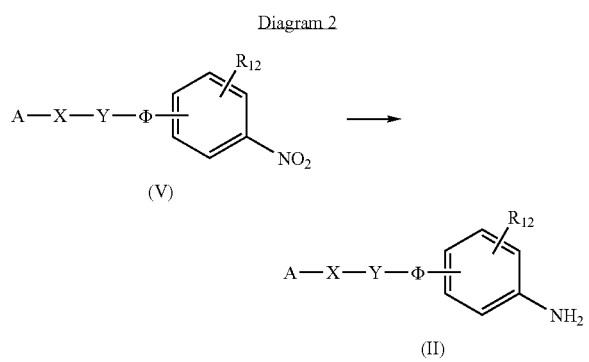

In the particular case of the indolic derivatives of general formula (V) (Diagram 6), the gentle reduction conditions of the nitro function (Zn in acetic acid) are inevitably accompanied by the loss of the unsaturation at the level of 1,2,3,6-tetrahydropyridine in order to produce the piperidine.

Deprotection of the Amino Group:

The intermediates of general formula (II), in which A, X, Y, Φ and $R_{12}$ are as defined above, can also be prepared from the intermediates of general formula (VI), Diagram 3, which are compounds comprising an amine protected in the form, for example, of 2,5-dimethylpyrrole (N=Gp') or of tert-butyl carbamate (NH-Gp). The pyrroles, for example, are deprotected by heating in the presence of hydroxylamine hydrochloride for at least 24 hours in order to finally produce the primary amines of general formula (II). The amines protected in the form of tert-butyl carbamates are released in a standard fashion in acidic medium by treatment with trifluoroacetic or hydrochloric acid.

Diagram 3

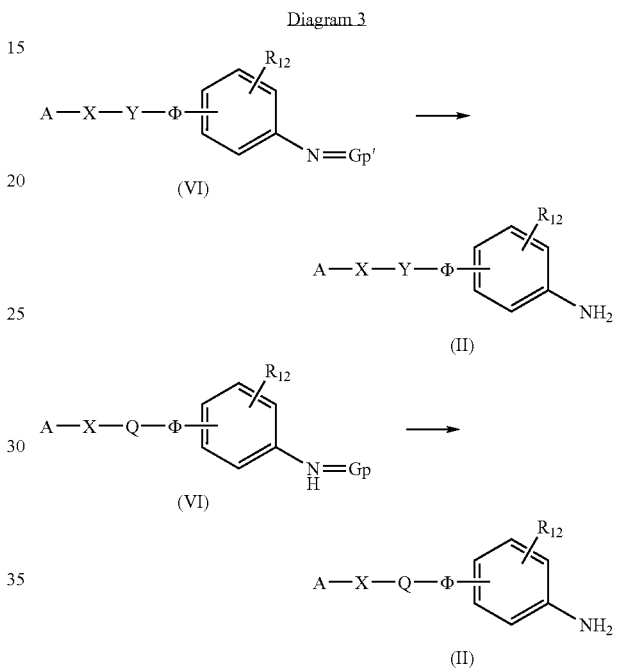

Preparation of Compounds of General Formula (V):

Synthesis of the Carboxamides:

The carboxamides of general formula (V), Diagram 4, in which X represents —CO—$NR_{15}$— and A, Y, Q, Φ, $R_{12}$ and $R_{15}$ are as defined above, are prepared by condensation of the acids of general formula (VII) with the commercial amines of general formula (VIII) under standard conditions for peptide synthesis (M. Bodanszky and A. Bodanszky, The Practice of Peptide Synthesis, 145 (Springer-Verlag, 1984)) in THF, dichloromethane or DMF in the presence of a coupling reagent such as dicyclohexylcarbodiimide (DCC), 1,1'-carbonyldiimidazole (CDI) (*J. Med. Chem.* (1992), 35 (23), 4464-4472) or 1-(3-dimethylaminopropyl)-3-ethylcarbodiimide hydrochloride (EDC or WSCI) (John Jones, The chemical synthesis of peptides, 54 (Clarendon Press, Oxford, 1991)).

The syntheses of the non-commercial acids of general formula (VII) are described in the "Preparation of the Intermediates" chapter.

Diagram 4

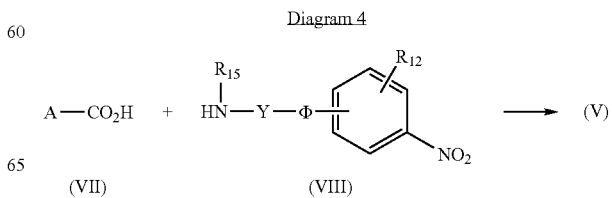

(A-X-GO-N series)

The carboxamides of general formula (V), Diagram 5, in which X represents —O—$(CH_2)_m$—, —S—$(CH_2)_m$— or —$NR_{15}$—$(CH_2)_m$— with A, Y, Φ, $R_{12}$ and $R_{16}$ as defined above (Q being a heterocycle), are prepared by condensation of the acids of general formula (IX) with the amines of general formula (X) or (XXII) under standard conditions for peptide synthesis as described previously. The syntheses of the acids of general formula (IX) and of the amines of general formula (X), non-commercial, are described in the "Preparation of the Intermediates" chapter.

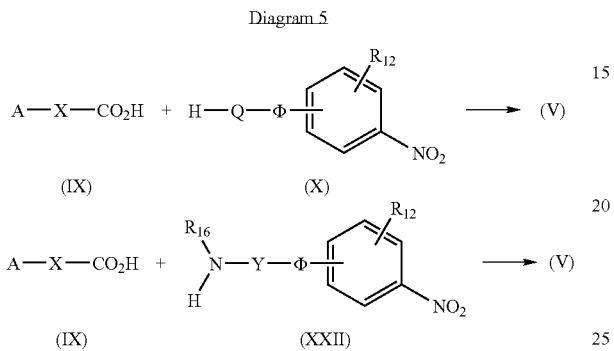

Diagram 5

Synthesis of the Derivatives of 1,2,3,6-tetrahydropyridine:

The indolic derivatives of general formula (V'), in which Q represents 1,2,3,6-tetrahydropyridine, Φ, $R_9$ and $R_{12}$ being as defined above, are prepared from the substituted commercial indoles of general formula (XI), Diagram 6. The experimental protocol of the condensation reaction with the piperidone is described in *Eur. J. Med. Chem.* (1987) 22, 33-43. The intermediate of general formula (XII) is then condensed in a standard fashion with the halogenated derivatives of general formula (XIII) in the presence of a base such as, for example, $Na_2CO_3$, in an appropriate polar solvent such as for example DMF, in order to produce the intermediates of general formula (V') (specific case of the intermediates of general formula (V)).

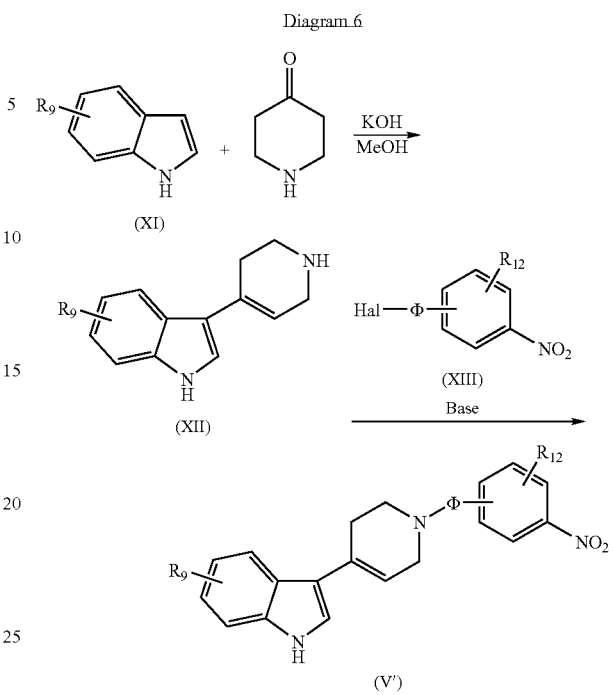

Diagram 6

The derivatives of general formula (Va) (specific case of the intermediates of general formula (V)), Diagram 7, in which Q represents 1,2,3,6-tetrahydropyridine, Φ, Y and $K_{12}$ being as defined above, Hal being a halogen atom, are also prepared by condensation of 4-phenyl-1,2,3,6-tetrahydropyrine with the halogenated derivatives of general formula (XIII) in the presence of a base such as, for example, $K_2CO_3$, in an appropriate polar solvent such as, for example, DMF. Alternatively, the compounds of general formula (Va) are accessible by Mitsonobu type condensation (*Synthesis* (1981), 1) between 4-phenyl-1,2,3,6-tetrahydropyrine and alcoholic derivatives of general formula (XVIII).

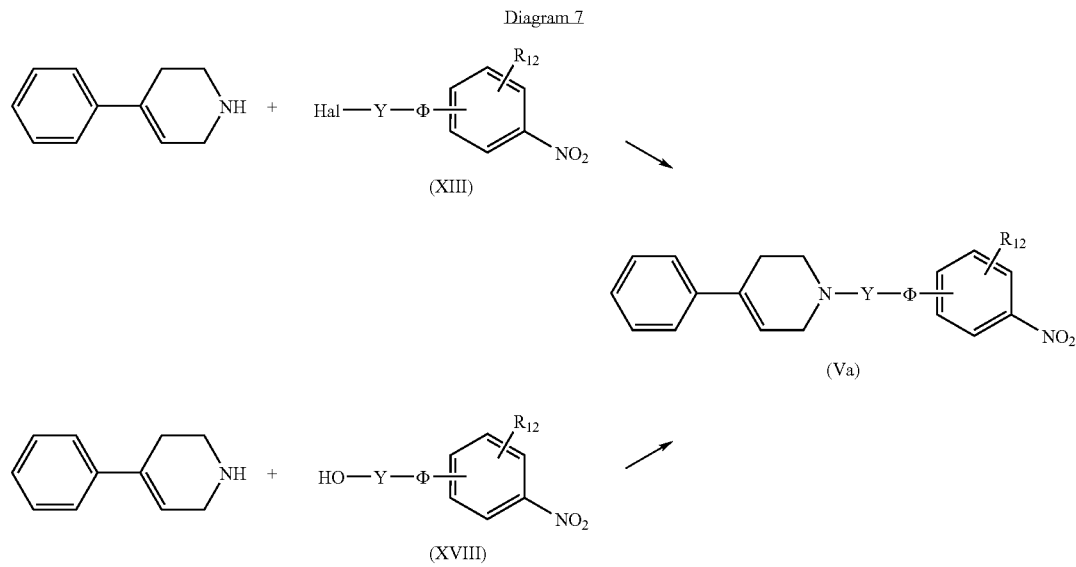

Diagram 7

Synthesis of Theophylline Derivatives:

The theophylline derivatives of general formula (Vb) (specific case of the intermediates of general formula (V)), Diagram 8, in which Y, Φ and $R_{12}$ are as defined above, are prepared by condensation of commercial Theophylline with the halogenated derivatives of general formula (XIV) in the presence of a base such as, for example, NaOH, in a hydroalcoholic solvent.

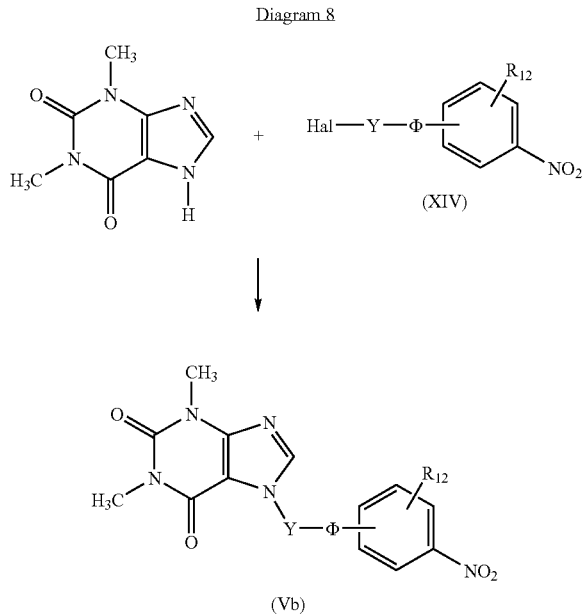

Synthesis of the Ethers of General Formula (V):

When Φ represents $-(CH_2)_p-O-(CH_2)_q-$, with A, Q, $R_{12}$, p and q as defined above, the ethers of general formula (V), Diagram 9, can be prepared in a single stage by condensation of the alcohols of general formula (XV) with the halogenated derivatives of general formula (XVI) in the presence of a base such as for example NaH in a polar solvent such as for example THF.

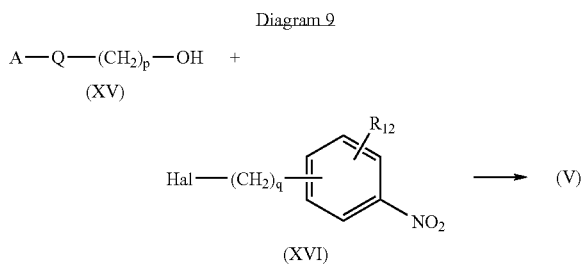

When Φ represents $-(CH_2)_p-O-(CH_2)_q-$, with A, $R_{12}$, p and q as defined above, the ethers of general formula (V) can also be prepared from the halogenated derivatives of formula (XVII) and the alcohols of general formula (XVIII), Diagram 10, in the presence of a base such as for example NaH in a polar solvent such as for example DMF.

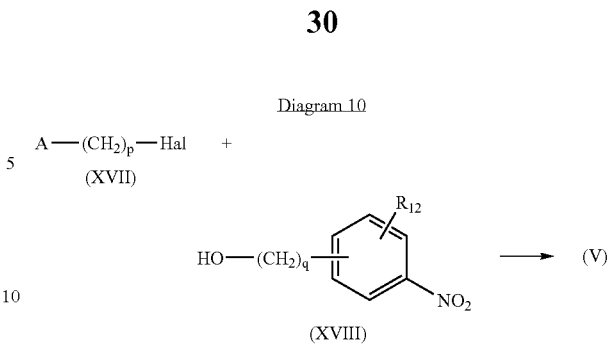

Synthesis of Carboxamides (A-X—N—CO— Series):

The carboxamides of general formula (V), Diagram 11, in which A, $R_{12}$, $R_{15}$, Y and Φ are as defined above, are prepared under the same peptidic coupling conditions as the carboxamides of the A-X—CO—N— series. The preparations of the non-commercial amines of general formula (XIX) and acids of general formula (XX) are described in the "Preparation of the Intermediates" chapter.

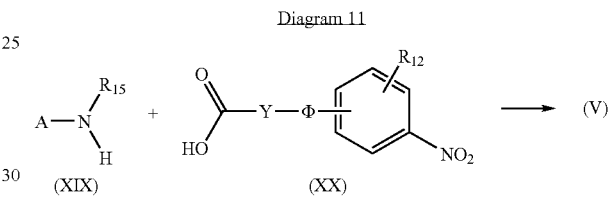

Synthesis of the Amines by Reducing Amination:

The amines of general formula (V), Diagram 12, in which A, $R_{12}$, $R_{16}$, Y, m and Φ are as defined above, can be prepared by condensation of an aldehyde of general formula (XXI) with a commercial amine of general formula (XXII) in a reducing medium. The reaction takes place in an alcoholic solvent such as, for example, methanol in the presence of a pulverulent 4 Å molecular sieve, activated beforehand, and of a reducing agent such as, for example, $NaBH_4$ or $NaBH_3CN$. Before te addition of the reducing agent, some imines can be isolated as intermediates of general formula (V).

The secondary amines of general formula (V) are then protected in the form of tert-butyl carbamate in the presence of di-tert-butyldicarbonate, and of a base such as, for example, triethylamine and in a solvent such as, for example, dichloromethane. The syntheses of the non-commercial aldehydes of general formula (XXI) are described in the "Preparation of the Intermediates" chapter.

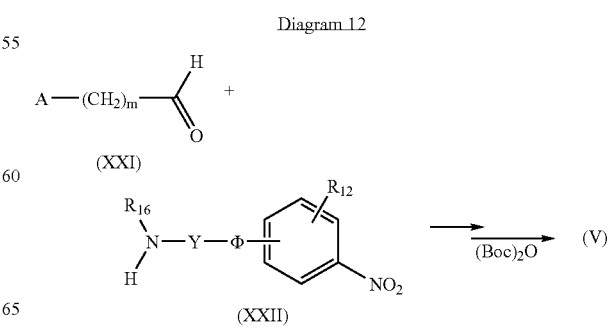

The amines of general formula (V), Diagram 13, in which A, X, $R_{12}$, $R_{16}$, p and q are as defined above, can also be prepared by condensation of an amine of general formula (XXIII) with a commercial aldehyde of general formula (XXIV) in a reducing medium under the conditions described previously. The secondary amines of general formula (V) are then protected in the form of tert-butyl carbamate, under the conditions described previously. The syntheses of the amines of general formula (XXIII) are described in the "Preparation of the Intermediates" chapter. Moreover, the non-commercial aldehydes of general formula (XXVI) can be prepared according to J. Org. Chem., 1993, 58, 1385-92.

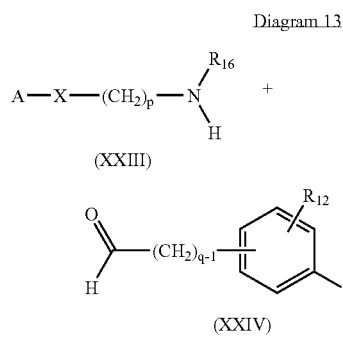

Synthesis of the Amines by Reduction of the Carboxamides:

The amines of general formula (V), Diagram 14, in which A, X, $R_{12}$, $R_{16}$ and q are as defined above, are accessible by reduction of the carboxamide derivatives of general formula (V), the synthesis of which is described in the "Synthesis of the carboxamides" chapter (Diagram 4). The reduction stage is carried out in an anhydrous medium, by heating at 70-80° C., in the presence of a carboxamide selective reagent such as, for example, $BH_3$.THF, in a solvent such as, for example, THF. The secondary amines thus prepared can be protected in the form of tert-butyl carbamate under the conditions described previously.

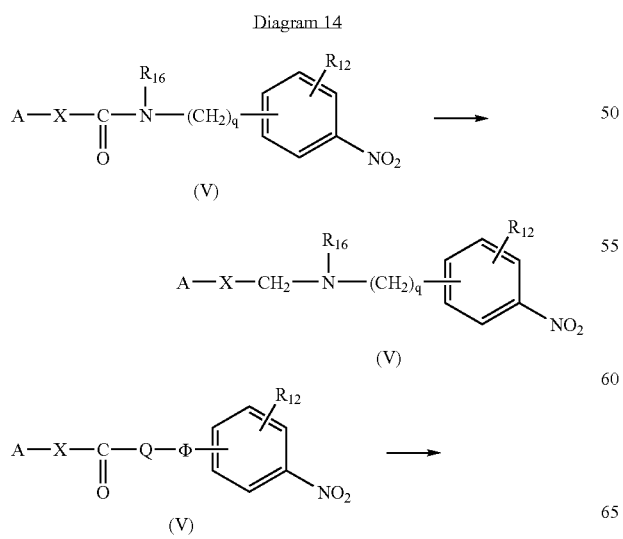

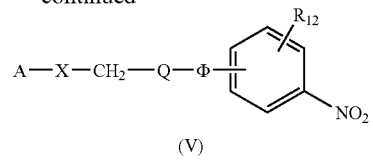

Synthesis of the Ureas:

The ureas of general formula (V), Diagram 15, in which A, Y, Φ, $R_{12}$, $R_{15}$ and $R_{16}$ are as defined above, are accessible by reaction of the amines of general formula (XIX) with the amines of general formula (XXII) in the presence of triphosgene and of a base such as, for example, diisopropylethylamine in an inert solvent such as dichloromethane according to an experimental protocol described in J. Org. Chem. (1994) 59 (7), 1937-1938.

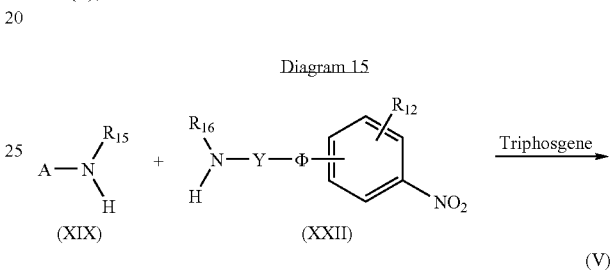

Synthesis of Pyrrolidinyl-Pyrimidine Derivatives:

The pyrimidine derivatives of general formula (V), Diagram 16, in which Q represents piperazine, Φ and $R_{12}$ being as defined above, are prepared by condensation of 4-chloro-2,6-di-pyrrolidin-1-yl-pyrimidine (J. Med. Chem. (1990) 33 (4), 1145-1151) with the piperazine derivatives of general formula (X), by heating, for 24 to 48 hours, in anhydrous pyridine at a temperature of 80-110° C.

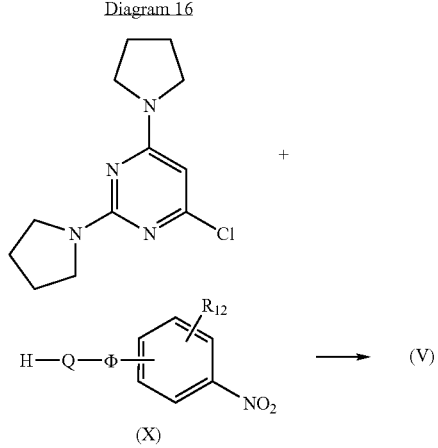

Synthesis of the Carboxamides (A-X—CO—N Series):

The carboxamides of general formula (VI), Diagram 17, in which A, Y, Φ, $R_{12}$, $R_{15}$, Gp and Gp' are as defined above, can be prepared from the commercial acids of general formula (VII) and the amines of general formulae (XXV) or (XXVI) under the standard conditions for peptide synthesis as described previously. The syntheses of the amines of general formulae (XXV) and (XXVI) are described in the "Preparation of the Intermediates" chapter.

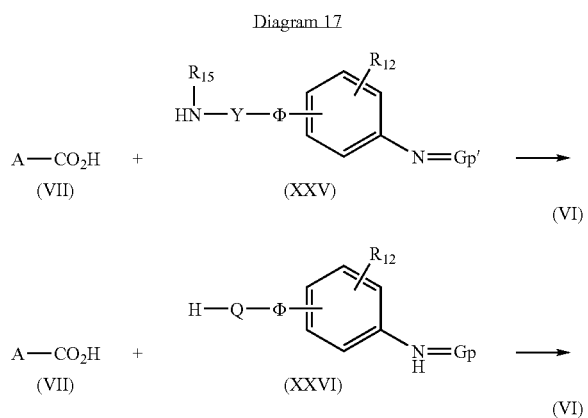

Synthesis of the Carboxamides (A-X—N—CO Series):

The carboxamides of general formula (VI), Diagram 18, in which A, Y, Φ, $R_{12}$, $R_{15}$ and Gp are as defined above, can be prepared by condensation of the amines of general formula (XIX), described previously, with the acids of general formula (XXVII) under the standard conditions for peptide synthesis as described previously. The acids of general formula (XXVII) are easily accessible by protection of the aniline function in the form, for example, of a tert-butyl carbamate under standard conditions.

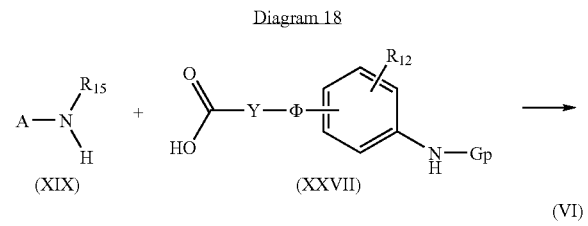

Preparation of Different Synthesis Intermediates:

Synthesis of Intermediates (VII):

The non-commercial acids of general formula (VII) in which A is as defined above are accessible using the methods of the literature. For example, 2-hydroxy-4,5,6-trimethoxybenzoic acid is obtained in two stages from 3,4,5-trimethoxyphenol according to J. Org. Chem. (1961) 26, 1221-1223, Acta Chem. Scandinavica (1973) 27, 888-890 or Can. J. Chem. (1972) 50, 1276-1282.

Certain acids of general formula (VII), in which A is as defined above, include an amine ($R_1$ substituent) which has to be protected in the form of a carbamate, in particular tert-butyl, before carrying out the condensation stage. This protection is carried out under standard conditions described in "M. Bodanszky et A. Bodanszky, The Practice of Peptide Synthesis, 145 (Springer Verlag, 1984)".

The acid derivatives of the benzofuranes are prepared using an experimental protocol described in J. Org. Chem. (1989) 54, 560-569.

Synthesis of Intermediates (IX):

The non-commercial acids of general formula (IX) in which X represents —O—$(CH_2)_m$— with A as defined above are prepared from the hydroquinones of general formula (IX.1) obtained according to the literature (J. Chem. Soc. Perkin 1 (1981) 303-306). Condensation with commercial halogenoesters of general formula (IX.2) is carried out in the presence of a base such as, for example, $K_2CO_3$, by heating in a polar solvent such as, for example, THF for at least 5 hours. The esters of general formula (IX.3) obtained intermediately are then deprotected (in an acid medium in the case of the tert-butyl esters) in order to produce the acids of general formula (IX).

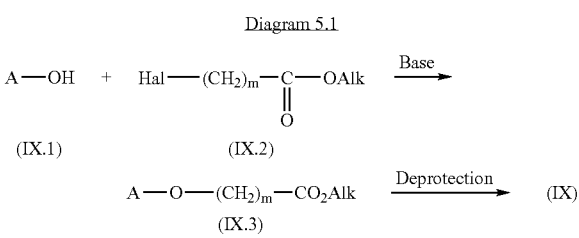

The acids of general formula (IX) in which X represents —S—$(CH_2)_m$— with A as defined above, are prepared according to the literature (J. Med. Chem. (1997) 40 (12), 1906-1918).

Synthesis of Intermediates (X):

The non-commercial amines of general formula (X), in which Q represents homopiperazine, 2-methylpiperazine, 2,5-dimethylpiperazine, 4-aminopiperidine, are synthesized in three stages from the corresponding commercial diamines. The diamines are selectively monoprotected in the form of carbamate (Synthesis (1984), (12), 1032-1033; Synth. Common. (1990), 20, (16), 2559-2564) before reaction by nucleophilic substitution on a halogen nitrobenzene, in particular 4-fluoronitrobenzene. The amines, previously protected, are released in the last stage, according to methods described in the literature (T. W. Greene and P. G. M. Wuts, Protective Groups in Organic Synthesis, Second edition (Wiley-Interscience, 1991)), in order to produce the intermediates of general formula (X).

Synthesis of Intermediates (XIX):

The amines of general formula (XIX), which are indoline or 1,2,3,4-tetrahydroquinoline derivatives, Diagram 11.1, in which T and $R_{17}$ are as defined above, can be prepared from the corresponding nitro derivatives of general formula (XIX.1). 6-nitro-1,2,3,4-tetrahydroquinoline is described in Can. J. Chem. (1952), 30, 720-722. The alkylation of the amine is carried out in a standard fashion by a strong base such as, for example, NaH, in an aprotic polar solvent such as, for example, DMF in the presence of a halogenated derivative such as, for example, MeI or $PhCH_2Br$. The nitro derivative of general formula (XIX.2) obtained intermediately is then reduced, for example, by Raney Nickel in the presence of hydrazine hydrate in order to produce the anilines of general formula (XIX).

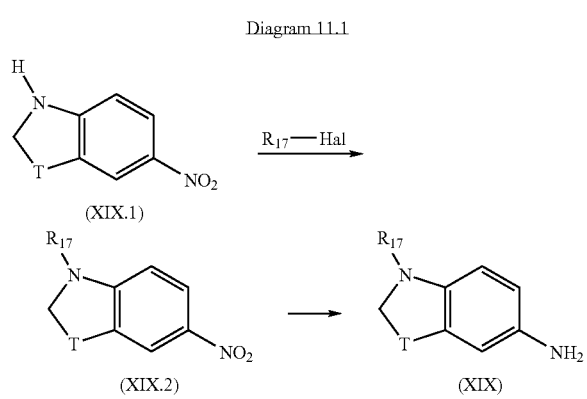

Diagram 11.1

Certain non-commercial phenylenediamine derivatives of general formula (XIX) can also be prepared according to *Farmaco* (1951) 6, 713-717.

In the specific case where A is a phenolic derivative, the anilines of general formula (XIX) are obtained by hydrogenation, in the presence of Pd/C, of the nitrophenol precursor derivatives. The nitrated derivatives of the di-tert-butyl phenols are accessible according to a method described in *J. Org. Chem.* (1968) 33 (1), 223-226.

Synthesis of Intermediates (XX):

The non-commercial carboxylic acids of general formula (XX) in which $R_{12}$, Y and Φ are as defined above are accessible by methods described in literature. The syntheses of several ω-(4'-nitrophenyl)alkanoic acids are described in *J. Med. Chem.* (1978) 21 (5), 430-437.

The synthesis of the carboxylic acids of general formula (XX), in which $R_{12}$ and Y are as defined above and Φ=thiazolidine, is carried out following a protocol described in *Liebigs Ann. Chem.* (1987), 927-934.

Synthesis of Intermediates (XXI):

The non-commercial aldehydes of general formula (XXI) in which A and m are as defined above are accessible from methods in the literature: *Bull. Chem. Soc. Jpn.* (1978) 51 (8), 2433-2434, *Bioorg. Med. Chem. Lett.* (1998)-8, 3453-3458.

Synthesis of Intermediates (XXIII):

The amines of general formula (XXIII), Diagram 13.1, in which A, X, $R_{16}$, Gp and p are as defined above, are prepared by condensation of the amines of general formula (XIX), described previously, and the protected amino acids of general formula (XXIII.1), under the standard conditions of peptide synthesis (see chapter Synthesis of the carboxamides (Diagram 4)). Deprotection of the amine of compounds of general formula (XXIII.2) is then carried out in acidic medium such as, for example, trifluoroacetic acid or hydrochloric acid.

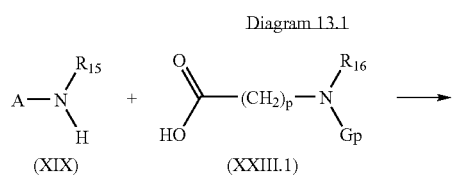

Diagram 13.1

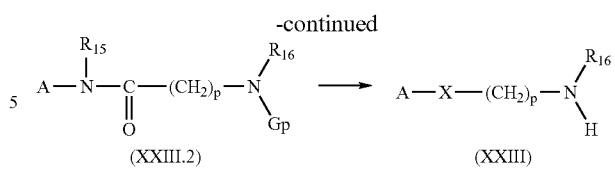

Synthesis of Intermediates (XXV):

The amines of general formula (XXV), in which Y and Φ are as defined above, are prepared in several steps from commercial aniline derivatives of general formula (XXV.1), Diagram 17.1. In order to protect the aniline function, a protective group is used which is resistant to a strong basic medium, for example the 2,5-dimethylpyrrole group. By the heating under reflux, in an appropriate solvent (e.g. toluene), of a mixture of the intermediate of general formula (XXV.1) with 2,5-hexanedione and paratoluenesulphonic acid, with simultaneous elimination of the water formed during the reaction, the intermediate of general formula (XXV.2) is obtained. The intermediate of general formula (XXV.3) is obtained by double alkylation of a carbon using two equivalents of a strong base, such as, for example, NaH in DMSO (*J. Org. Chem.* (1971) 36 (9), 1308-1309), in the presence of a dihalogenated derivative. The amines of general formula (XXV) are then obtained by reduction of the nitrile using, for example, $LiAlH_4$, in a solvent such as, for example, anhydrous THF.

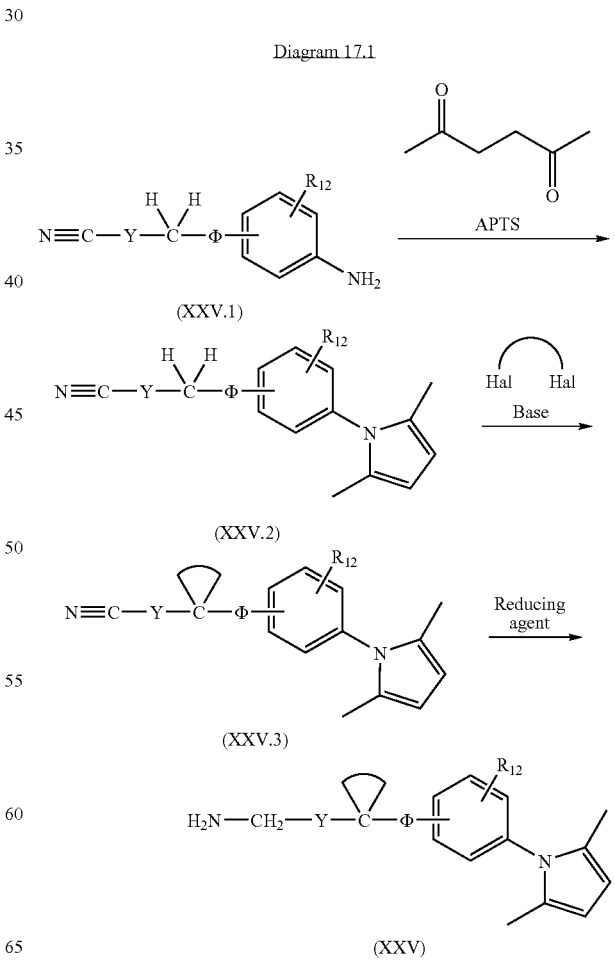

Diagram 17.1

Synthesis of Intermediates (XXVI):

The amines of general formula (XXVI), Diagram 17.2, in which $R_{12}$ and $\Phi$ are as defined above, are prepared in several stages from a commercial azetidine derivative and a halogenated derivative of general formula (XIII). The condensation stage is carried out in a standard fashion in the presence of a strong base such as, for example, NaH in an inert anhydrous solvent such as, for example, THF. Reduction of the nitro derivative by tin chloride (*J. Heterocycle Chem.* (1987), 24, 927-930; *Tetrahedron Letters* (1984), 25 (8), 839-842) produces the aniline derivative of general formula (XXVI.2) which is directly protected in the form of a tert-butyl carbamate under the conditions described previously. The amine of general formula (XXVI) is obtained by hydrogenolysis of the dibenzyl group in the presence of palladium hydroxide.

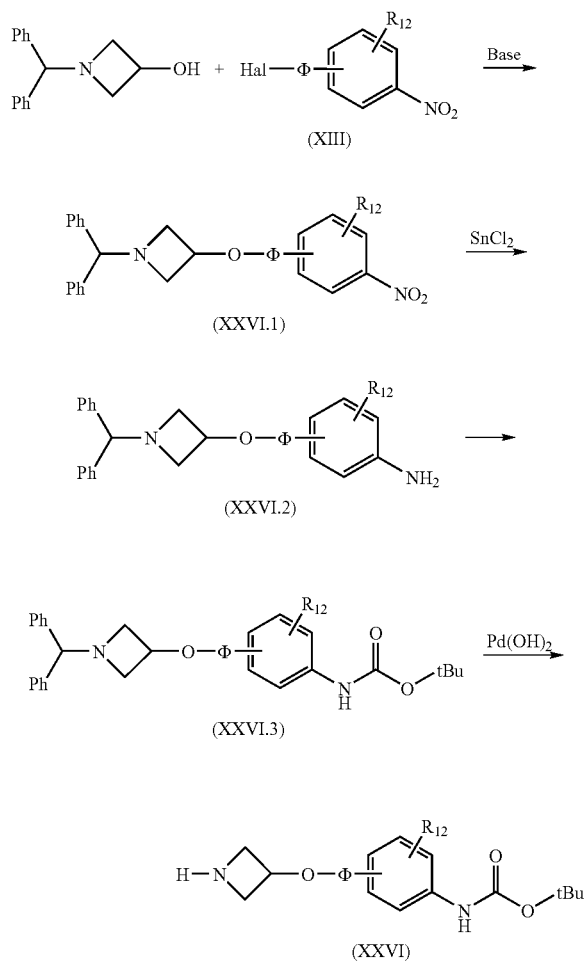

Diagram 17.2

Unless they are defined differently, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are presented to illustrate the above procedures and should in no way be considered as restricting the scope of the invention.

EXAMPLES

Example 1

2-hydroxy-5-methoxy-N-{2-[4-[(2-thienyl(imino)methyl)amino]phenyl]ethyl}-benzamide hydrochloride 1.1.) 2-hydroxy-5-methoxy-N-(2-(4-nitrophenyl)ethyl}-benzamide 4-nitrophenethylamine hydrochloride (1.81 g; 8.9 mmole), triethylamine (2.8 ml; 20=mole), hydroxybenzotriazole (1.45 g; 10.7 mmole) and 1-(3-dimethylaminopropyl)-3-ethyl-carbodiimide hydrochloride (3.75 g; 19.62 mmole) are added to a solution of 1.5 g (8.9 mmole) of 5-methoxy-salicylic acid in dichloromethane (80 ml). The reaction medium is agitated overnight at 25° C. The mixture is diluted with 40 ml of water and agitated for ten minutes, then the product is extracted with dichloromethane. The organic solution is dried over sodium sulphate, filtered and concentrated under vacuum and the evaporation residue is purified on a silica column (eluent=ethyl acetate/heptane; 50/50) in order to produce a white solid which is obtained with a yield of 64%. Melting point: 200° C.

NMR $^1$H (DMSO d6, 400 MHz, δ): 3.00 (m, 2H, $CH_2$); 3.60 (m, 2H, $CH_2$); 3.70 (S, 3H, —$OCH_3$); 6.80 (d, 1H, arom., J=8.8 Hz); 7.00 (d, 1H, arom., J=8.8 Hz); 7.35 (s, 1H, arom.); 7.50 (d, 2H, arom., J=7.8 Hz); 8.10 (d, 2H, arom., J=7.6 Hz); 8.90 (broad s, 1H, CO—NH); 11.90 (broad s, 1H, —OH).

1.2) 2-hydroxy-5-methoxy-N-{2-(4-aminophenyl) ethyl}-benzamide

Intermediate 1.1, 2.10 g (6.64 mmole) is dissolved in a mixture of ethanol (40 ml) and dichloromethane (60 ml) and 0.3 g of palladium on carbon (10%) is added. The reaction medium is placed under a hydrogen atmosphere under a pressure of 4 bars. The catalyst is filtered out and the solvent evaporated off under reduced pressure. The evaporation residue is purified on a silica column (eluent=ethyl acetate/heptane; 50/50) in order to produce a white-cream solid. Melting point: 130° C.

NMR $^1$H (DMSO d6, 400 MHz, δ): 2.67 (t, 2H, $CH_2$, J=7.4 Hz); 3.43 (m, 2H, $CH_2$); 3.73 (S, 3H, —$OCH_3$); 4.90 (S, 2H, $NH_2$); 6.50 (d, 2H, arom., J=7.8 Hz); 6.82 (d, 1H, arom., J=8.8 Hz); 6.90 (d, 2H, arom., J=7.8 Hz); 7.00 (d, 1H, arom., J=8.8 Hz); 7.39 (S, 1H, arom.); 8.87 (broad 1H, CO—NH); 12.09 (broad s, 1H, —OH).

1.3) 2-hydroxy-5-methoxy-N-{2-[4-[(2-thienyl(imino)methyl)amino]phenyl]ethyl}-benzamide hydrochloride Intermediate 1.2 (0.6 g; 2.1 mmole) is dissolved in 2-propanol (10 ml), 0.896 g of S-methyl-2-thiophenethiocarboximide hydroiodide (3.14 mmole) (Ann. Chim. (1962), 7, 303-337) is added.

After heating at 50° C. for 15 hours, the reaction mixture is concentrated to dryness under vacuum. The residue is taken up in ethyl acetate and a saturated solution of sodium carbonate. After decantation, the organic phase is washed successively with 50 ml of a saturated solution of sodium carbonate, water and brine. The organic solution is dried over sodium sulphate, filtered and evaporated under reduced pressure. The evaporation residue is purified on a silica column (eluent ethanol/dichloromethane, 5/95). 0.523 g of free base is obtained. The hydrochloride is prepared from 0.523 g (1.32 mmole) of the base dissolved in 20 ml of acetone and salified in the presence of 2.0 ml (2.0 mmole) of a molar solution of HCl in anhydrous diethyl ether. The crystals obtained are filtered and rinsed in diethyl ether in order to obtain after drying 0.58 g (yield of 64%) of the sought product in the form of a white solid. Melting point: 242° C.

NMR $^1$H (DMSO d6, 400 MHz, δ): 2.94 (t, 2H, CH$_2$, J=7.2 Hz); 3.58 (m, 2H, CH$_2$); 3.73 (s, 3H, —OCH$_3$); 6.85 (d, 1H, arom., J=9.0 Hz); 7.01 (d, 1H, arom., J=8.8 Hz); 7.20-7.70 (m, 6H, arom.); 8.16 (m, 2H, thiophene); 8.88 (broad s, 1H, NH$^+$); 9.11 (broad t, 1H, CO-NTH, J=5.15 Hz); 9.83 (broad s, 1H, NH$^+$); 11.54 (broad s, 1H, NH$^+$); 12.10 (s, 1H, —OH).

IR: $v_{C=N}$ (amidine): 1645 cm$^{-1}$; $v_{C=O}$ (amide): 1645 cm$^{-1}$.

Example 2

2-hydroxy-5-methylthio-N-{2-[4-[(2-thienyl(imino)methyl)amino]phenyl]ethyl-benzamide hydroiodide The experimental protocol used is the same as that described for Example 1, except that 5-methylthiosalicylic acid replaces 5-methoxysalicylic acid. The hydroiodide formed precipitates during the reaction. The crystals formed are filtered out and washed with diethyl ether. An off-white solid is obtained. Melting point: 211.4-212.6° C.

NMR $^1$H (DMSO d6, 400 MHz, δ): 2.49 (s, 3H, —SCH$_3$); 2.94 (t, 2H, CH$_2$, J=7.36 Hz); 3.57 (m, 2H, CH$_2$); 6.90 (d, 1H, arom., J=8.64 Hz); 7.20-7.60 (m, 6H, arom.); 7.80 (s, 1H, arom.); 8.10 (m, 2H, thiophene); 8.87 (broad s, 1H, NH$^+$); 9.02 (broad t, 1H, CO—NH, J=5.12 Hz); 9.77 (broad s, 1H, NH$^+$); 11.35 (broad s, 1H, NH$^+$); 12.48 (s, 1H, —OH).

IR: $v_{C=N}$ (amidine): 1639 cm$^{-1}$; $v_{C=O}$ (amide): 1656 cm$^{-1}$.

Example 3

2,5-dihydroxy-N-{2-[4[(2-thienyl(imino)methyl)amino]phenyl]ethyl-benzamide hydrochloride The experimental protocol used is the same as that described for Example 1, with 2,5-dihydroxybenzoic acid replacing 5-methoxysalicylic acid. A pinkish white solid is obtained. Melting point: 250° C.

NMR $^1$H (DMSO d6, 400 MHz, δ): 2.92 (t, 2H, CH$_2$, J=7.20 Hz); 3.55 (m, 2H, CH$_2$); 6.75 (d, 1H, arom., J=8.76 Hz); 6.85 (d, 1H, arom., J=8.76 Hz); 7.24 (s, 1H, arom.); 7.30-7.50 (m, 5H, arom.); 8.16 (m, 2H, thiophene); 8.83 (m, 1H, CO—NH); 8.9 (broad s, 1H, NH$^+$); 9.07 (s, 1H, —OH); 9.8 (broad s, 1H, NH$^+$); 11.40 (s, 1H, —OH); 11.70 (S, 1H, NH$^+$).

IR: $v_{C=N}$ (amidine): 1652 cm$^{-1}$; $v_{C=O}$ (amide): 1668 cm$^{-1}$.

Example 4

2-hydroxy-3-isopropyl-N-{2-[4-[(2-thienyl(imino)methyl)amino]phenyl]ethyl}-benzamide hydrochloride The experimental protocol used is the same as that described for Example 1, with 2-hydroxy-3-isopropyl-benzoic acid replacing 5-methoxysalicylic acid. A white solid is obtained. Melting point: 142.5-144° C.

NMR $^1$H (DMSO d6, 400 MHz, δ): 1.17 (d, 6H, isopropyl, J=6.9 Hz); 2.93 (m, 2H, CH$_2$); 3.24 (m, 1H, isopropyl); 3.58 (m, 2H, CH$_2$); 6.82 (t, 1H, arom., J=7.8 Hz); 7.20-7.60 (m, 6H, arom.); 7.80 (d, 1H, arom. J=7.9 Hz); 8.19 (m, 2H, thiophene); 8.89 (broad s, 1H, NH$^+$); 9.23 (broad s, 1H, CO—NH); 9.86 (broad s, 1H, NH$^+$); 11.62 (broad s, 1H, NH$^+$); 13.45 (s, 1H, —OH).

IR: $v_{C=N}$ (amidine): 1637 cm$^{-1}$; $v_{C=O}$ (amide): 1648 cm$^{-1}$.

Example 5

2,6-dihydroxy-N-{2-[4-[(2-thienyl(imino)methyl)amino]phenyl]ethyl}-benzamide hydrochloride The pin protocol used is the same as that described for Example 1, with 2,6-dihydroxybenzoic acid replacing 5-methoxysalicylic acid. A pale yellow-white solid is obtained. Melting point >280° C.

NMR $^1$H (DMSO d6, 400 MHz, δ): 2.94 (t, 2H, CH$_2$, J=7.14 Hz); 3.61 (m, 2H, CH$_2$); 6.40 (d, 2H, arom., J=8.32 Hz); 7.14 (t, 1H, arom., J=8.28 Hz), 7.20-7.60 (m, 5H, arom.); 8.17 (m, 2H, thiophene); 8.9 (broad s, 1H, NH$^+$); 9.03 (t, 1H, CO—NH, J=5.24 Hz); 9.85 (broad s, 1H, NH$^+$); 11.55 (broad s, 1H, NH$^+$); 12.71 (broad s, 2H, —OH). IR: $v_{C=N}$ (amidine): 1593 cm$^{-1}$; $v_{C=O}$ (amide): 1633 cm$^{-1}$.

Example 6

2-hydroxy-4,6-dimethoxy-N-{2-[4-[(2-thienyl(imino)methyl)amino]phenyl]ethyl}-benzamide hydrochloride The experimental protocol used is the same as that described for Example 1, with -2-hydroxy-4,6-dimethoxy benzoic acid replacing 5-methoxysalicylic acid. A white solid is obtained. Melting point: 196-199° C.

NMR $^1$H (DMSO d6, 400 MHz, δ): 2.92 (t, 2H, CH$_2$, J=7.24 Hz); 3.58 (m, 2H, CH$_2$); 3.76 (s, 3H, —OCH$_3$); 3.85 (s, 3H, —OCH$_3$); 6.07 (s, 1H, arom.); 6.10 (s, 1H, arom.); 7.30-7.60 (m, 5H, arom.); 8.17 (m, 2H, thiophene); 8.58 (broad t, 1H, CONH, J=5.36 Hz); 8.88 (broad s, 1H, NH$^+$); 9.85 (broad s, 1H, NH$^+$); 11.60 (broad s, 1H, NH$^+$); 14.39 (s, 1H, —OH).

IR: $v_{C=N}$ (amidine): 1598 cm$^{-1}$; $v_{C=O}$ (amide): 1637 cm$^{-1}$.

Example 7

2-hydroxy-4,5,6-trimethoxy-N-{2-[4-[(2-thienyl(imino)methyl)amino]phenyl]ethyl}-benzamide hydrochloride The experimental protocol used is the same as that described for Example 1, with 2-hydroxy-4,5,6-trimethoxy-benzoic acid (*J. Org. Chem.* (1961) 26, 1221-1223; *Acta Chem. Scandinavica* (1973) 27, 888-890) replacing 5-methoxysalicylic acid. Melting point: 90-95° C.

NMR $^1$H (DMSO d6, 400 MHz, δ): 2.95 (t, 2H, CH$_2$, J=7.12 Hz); 3.61 (m, 2H, CH$_2$); 3.66 (s, 3H, —OCH$_3$); 3.79 (S, 3H, —OCH$_3$); 3.80 (S, 3H, —OCH$_3$); 6.32 (S, 1H, arom.); 7.39-7.48 (m, 5H, arom.); 8.16 (m, 2H, thiophene); 8.62 (broad s, 1H, CO—NH); 8.90 (broad s, 1H, NH$^+$), 9.80 (broad s, 1H, NH$^+$); 11.40 (broad s, 1H, NH$^+$); 13.67 (s, 1H, OH).

IR: $v_{C=N}$ (anidine): 1591 cm$^{-1}$; $v_{C=O}$ (amide): 1631 cm$^{-1}$.

Example 8

2-hydroxy-3,5-di-tert-butyl-N-{2-[4-[(2-thienyl (imino)methyl)amino]phenyl]ethyl-benzamide hydrochloride The experimental protocol used is the same as that described for Example 1, with 2-hydroxy-3,5-di-tert-butyl acid replacing 5-methoxy-salicylic acid. A white solid is obtained. Melting point: 172.4-173.8° C.

NMR $^1$H (DMSO d6, 400 MHz, δ): 1.28 (s, 9H, t-Bu); 1.36 (s, 9H, t-Bu); 2.96 (t, 2H, CH$_2$, J=7.28 Hz); 3.58 (m, 2H, CH$_2$); 7,36-7.46 (m, 6H, arom.); 7.70 (s, 1H, arom.); 8.17 (m, 2H, thiophene), 8.88 (broad s, 1H, NH$^+$); 9.22 (broad t, 1H, CONH, J=5.32 Hz); 9.82 (broad s, 1H, NH$^+$); 11.55 (broad s, 1H, NH$^+$); 13.60 (s, 1H, —OH).

IR: $v_{C=N}$ (amidine): 1585 cm$^{-1}$; $v_{C=O}$ (amide): 1631 cm$^{-1}$.

Example 9

2-hydroxy-3,5-diisopropyl-N-{2-[4-[(2-thienyl (imino)methyl)amino]phenyl]ethyl}-benzamide hydrochloride The experimental protocol used is the same as that described in Example 1, with 2-hydroxy-3,5-diisopropylbenzoic acid replacing 5-methoxysalicylic acid. A white solid is obtained. Melting point: 212.6°-214° C.

NMR $^1$H (DMSO d6, 400 MHz, δ). 1.35 (m, 12H, isopropyl); 2.98 (m, 1H, isopropyl); 3.12 (t, 2H, CH$_2$, J=7.58 Hz); 3.38 (m, 1H, isopropyl); 3.72 (m, 2H, CH$_2$); 7.37 (s, 1H, arom.); 7.54-7.63 (m, 5H, arom.); 7.77 (S, 1H, arom.); 8.33 (m, 2H, thiophene); 9.00 (broad s, 1H, NH$^+$); 9.30 (m, 1H, CONH); 10.00 (broad s, 1H, NH$^+$).

IR: $v_{C=N}$ (amidine): 1590 cm$^{-1}$; $v_{C=O}$ (amide): 1637 cm$^{-1}$.

Example 10

2,4-dihydroxy-3,6-dimethyl-N-{2-[4-[(2-thienyl (imino)methyl)amino]phenyl]ethyl-benzamide hydrochloride The experimental protocol used is the same as that described for Example 1, with 2,4-dihydroxy-4,6-dimethylbenzoic acid replacing 5-methoxysalicylic acid. A beige solid is obtained. Melting point: 150.3-151.9° C.

NMR $^1$H (DMSO d6, 400 MHz, δ): 2.08 (S, 3H, CH$_3$); 2.38 (S, 3H, CH$_3$); 3.09 (t, 2H, CH$_2$, J=7.36 Hz); 3.61 (m, 2H, CH$_2$); 6.38 (s, 1H, arom.); 7.55-7.63 (m, 5H, arom.); 8.15 (broad t, 1H, CONH, J=5.28 Hz); 8.35 (m, 2H, thiophene); 9.00 (broad s, 1H, NH$^+$); 9.78 (broad s, 1H, NH$^+$); 10.00 (s, 1H, —OH); 10.70 (broad s, 1H, —NH$^+$); 11.69 (broad s, 1H, NH$^+$).

IR: $v_{C=N}$ (amidine): 1590 cm$^{-1}$; $v_{C=O}$ (amide): 1637 cm$^{-1}$.

Example 11

2,7-dihydroxy-N-{2-[4-[(2-thienyl(imino)methyl) amino]phenyl]ethyl}-2-naphthalenecarboxamide hydrochloride The experimental protocol used is the same as that described for Example 1, with 3,7-dihydroxy-2-naphthoic acid replacing 5-methoxy salicylic acid. A yellow solid is obtained. Melting point, 219-219.7-° C.

NMR $^1$H (DMSO d6, 400 MHz, δ): 2.98 (t, 2H, CH$_2$ J=7.30 Hz); 3.64 (m, 2H, CH$_2$); 7.09-7.60 (m, 9H, arom.); 8.16 (m, 2H, thiophene); 8.32 (S, 1H, arom.); 8.90 (broad s, 1H, NH$^+$); 9.16 (broad s, 1H, CONH); 9.60 (s, 1H, —OH); 9.80 (broad s, 1H, NH$^+$); 11.40 (broad s, 1H, NH$^+$); 11.77 (s, 1H, OH).

IR: $v_{C=N}$ (amidine): 1625 cm$^{-1}$; $v_{C=O}$ (amide): 1657 cm$^{-1}$

Example 12

2-hydroxy-4-methoxy-N-{2-[4-[(2-thienyl(imino) methyl)amino]phenyl]ethyl}-benzamide hydrochloride The experimental protocol used is the same as that described for Example 1, with 2-hydroxy-4-methoxybenzoic acid replacing 5-methoxysalicylic acid. Melting point >250° C.

NMR $^1$H (DMSO d6, 400 MHz, δ): 2.93 (t, 2H, CH$_2$, J=7.20 Hz); 3.54 (m, 2H, CH$_2$); 3.76 (s, 3H, —OCH$_3$); 6.44 (m, 2H, arom.); 7.40 (m, 5H, arom.); 7.87 (d, 1H, arom., J=8.80 Hz); 8.17 (m, 2H, thiophene); 8.91 (broad s, 1H, CONH); 8.91 (broad s, 1H, NH$^+$); 9.82 (broad s, 1H, NH$^+$); 11.54 (broad s, 1H, NH$^+$); 13.08 (s, 1H, —OH).

IR: $v_{C=N}$ (amidine): 1599 cm$^{-1}$; $v_{C=O}$ (amide): 1640 cm$^{-1}$.

Example 13

2-hydroxy-3-isopropyl-5-methoxy-N-{2-[4-[(2-thienyl(imino)methyl) amino]phenyl]ethyl}-benzamide hydrochloride The experimental protocol used is the same as that described for Example 1, with 2-hydroxy-3-isopropyl-5-methoxybenzoic acid (Can. J. Chem. (1972) 50, 1276-1282) replacing 5-methoxysalicylic acid. A white solid is obtained. Melting point: 170-175° C.

NMR $^1$H (DMSO d6, 400 MHz, δ): 1.15 (d, 6H, isopropyl, J=6.88 Hz); 2.96 (t, 2H, CH$_2$, J=7.36 Hz); 3.23 (m, 1H, isopropyl); 3.57 (m, 2H, CH$_2$); 3.75 (s, 3H, —OCH$_3$); 6.93 (s, 1H, arom.); 7.39 (m, 6H, arom.); 8.17 (m, 2H, thiophene); 8.90 (broad s, 1H, NH$^+$); 9.27 (broad t, 1H, CONH, J=5.14 Hz); 9.90 (broad s, 1H, NH$^+$); 11.60 (broad s, 1H, NH$^+$); 13.00 (s, 1H, OH).

IR: $v_{C=N}$ (amidine): 1594 cm$^{-1}$; $v_{C=O}$ (amide): 1648 cm$^{-1}$.

Example 14

N-(2-hydroxy-3-tert-butyl-5-methoxy)-4-{[2-thienyl (imino)methyl]amino}benzene-butanamide hydrochloride 14.1.) N-(2-methoxy-methoxy-3-tert-butyl-5-methoxy)-4-nitrobenzene-butanamide The experimental protocol used is the same as that described for intermediate 1,1, with 4-(4-nitrophenyl)butanoic acid replacing 5-methoxysalicylic acid and 2-methoxymethoxy-3-tert-butyl-5-methoxyaniline (*Biorg & Med. Chem.* (1998), 6, 849-868) replacing 4-nitrophenethylamine hydrochloride. A red oil is obtained with a yield of 82%.

NMR $^1$H (DMSO d6, 400 MHz, δ): 1.32 (s, 9H, t-Butyl); 1.93 (m, 2H, CH$_2$); 2.37 (m, 2H, CH$_2$); 2.77 (m, 2H, CH$_2$); 3.53 (s, 3H, OCH$_3$); 3.68 (s, 3H, OCH$_3$); 4.90 (s, 2H, —OCH$_2$O—); 6.57 (s, 1H, arom.); 7.38 (s, 1H, arom.); 7.51 (d, 2H, arom., J=8.50 Hz); 8.16 (d, 2H, arom., J=8.50 Hz); 9.28 (s, 1H, NHCO).

14.2) N-(2-hydroxy-3-tert-butyl-5-methoxy)-4-nitro-benzenebutanamide

Concentrated hydrochloric acid (0.6 ml) is added to a solution of 1.49 g (3.86 mmole) of N-(2-methoxy-methoxy-3-tert-butyl-5-methoxy)$_4$-nitrobenzene-butanamide in methanol (30 ml). The reaction medium is agitated overnight at 25° C. The solvents are evaporated off and the residue washed successively with 3×40 ml of water then with 40 ml of brine. The organic solution is dried over sodium sulphate, filtered and concentrated under reduced pressure in order to produce a brown oil, which is sufficiently pure to be used directly in the following stage.

NMR $^1$H (DMSO d6, 400 MHz, δ): 1.34 (s, 9H, t-Bu); 1.76 (m, 2H, CH$_2$); 2.44 (m, 2H, CH$_2$); 2.78 (m, 2H, CH$_2$); 3.65 (s, 3H, OCH$_3$); 6.61 (s, 1H, arom.); 6.66 (S, 1H, arom.); 7.53 (d, 2H, arom, J=8.62 Hz); 8.18 (d, 2H, arom., J=8.62 Hz); 8.56 (s, 1H, NH—CO); 9.94 (s, 1H, —OH).

14.3) N-(2-hydroxy-3-tert-butyl-5-methoxy)-4-aminobenzene-butanamide

The experimental protocol used is the same as that described for intermediate 1.2, with N-(2-hydroxy-3-tert-butyl-5-methoxy)-4-nitro-benzenebutanamide replacing 2-hydroxy-5-methoxy-N-{2-(4-nitrophenyl) ethyl}-benzamide.

14.4) N-(2-hydroxy-3-tert-butyl-5-methoxy)-4-{[2-thienyl (imino) methyl]amino}benzenebutanamide hydrochloride The experimental protocol used is the same as that described for Example 3, with N-(2-hydroxy-3-tert-butyl-5-methoxy)-4-aminobenzene-butanamide replacing 2-hydroxy-5-methoxy-N-{2-(4-aminophenyl)ethyl}-benzamide. Melting point: 146-154-° C.

NMR $^1$H (DMSO d6, 400 MHz, δ) 1.34 (s, 9H, t-Butyl); 1.96 (m, 2H, CH$_2$); 2.70 (m, 2H, CH$_2$); 3.42 (m, 2H, CH$_2$); 3.65 (s, 3H, —OCH$_3$); 6.59 (s, 1H, arom.); 6.83 (s, 1H, arom.); 7.36-7.41 (m, 5H, arom.); 8.17 (m, 2H, thiophene); 8.75 (s, 1H, NHCO); 8.90 (broad s, 1H, NH$^+$); 9.80 (broad s, 1H, NH$^+$); 10.35 (s, 1H, —OH); 11.60 (broad s, 1H, NH$^+$).

IR: $v_{C=N}$ (amidine): 1596 cm$^{-1}$; $v_{C=O}$ (amide): 1698 cm$^{-1}$.

Example 15

3,4-dihydro-6-hydroxy-2,5,7,8-tetramethyl-N-{2-[4-[(2-thienyl(imino) methyl)amino]phenyl]ethyl}-2H-1-benzopyran-2-carboxamide hydrochloride The experimental protocol is the same as that used for Example 1.1, with TROLOX replacing 5-methoxy-salicylic acid. A white solid is obtained. Melting point: 160-168° C.

NMR $^1$H (DMSO d6, 400 MHz, δ): 1.34 (s, 3H, —CH$_3$); 1.70 (m, 1H, CH$_2$-Trolox); 1.99 (s, 3H, —CH$_3$); 2.07 (s, 6H, CH$_3$×2); 2.13 (m, 1H, CH$_2$-Trolox); 2.40 (m, 1H, CH$_2$-Trolox); 2.60 (m, 1H, CH$_2$-Trolox); 2.72 (m, 2H, CH$_2$); 3.31 (m, 2H, CH$_2$); 4.30 (broad s, 1H, NH$^+$); 7.20-7.23 (m, 6H, Arom); 7.57 (s, 1H, —OH); 8.17 (m, 2H, thiophene); 8.90 (broad s, 1H, NH$^+$); 9.80 (broad s, 1H, NH$^+$).

IR $v_{C=N}$ (amidine): 1599 cm$^{-1}$; $v_{C=O}$ (amide): 1653 cm$^1$.

Example 16

3,4-dihydro-6-hydroxy-2,5,7,8-tetramethyl-N-{1-[4-[(2-thienyl(imino)methyl)amino]phenyl]methyl}-2H-1-benzopyran-2-carboxamide hydrochloride The experimental protocol used is the same as that described for Example 1, with Trolox replacing 5-methoxy-salicylic acid. A white solid is obtained.

Melting point: 128-130° C.

NMR $^1$H (400 MHz, DMSO d6, δ): 1.45 (s, 3H, CH$_3$); 1.95 (m, 2H, Ω CH$_2$—CH$_2$); 2.00 (s, 3H, CH$_3$); 2.10 (2s, 6H, 2×CH$_3$); 2.50 (m, 2H, Ω CH$_2$—CH—)); 4.25 (m, 2H, CH$_2$—N); 6.35 (broad s, 2H, OH+NH$^+$); 6.65 (d, 2H, arom.); 6.90 (d, 2H, arom.); 7.10 (m, 1H, arom.); 7.60 (m, 2H, arom.); 7.75 (broad s, 2H, NH$^+$).

IR: $v_{C=N}$ (amidine): 1617 cm$^{-1}$; $v_{C=O}$ (amide): 1654 cm$^{-1}$.

Example 17

N-(4-hydroxyphenyl)-2-thiophenecarboximidamide hydroiodide

A mixture comprising 0.55 g (5 mmole) of 4-aminophenol and of 1.42 g (5 mmole) of S-methyl-2-thiophenethiocarboximide hydroiodide in solution in 20 ml of isopropanol is agitated for 2 hours at 40° C. The precipitate formed is then filtered and rinsed twice with 25 ml of ethyl ether. After drying the expected product is obtained in the form of a white powder with a yield of 77%.

Melting point: 258-259° C.

Example 18

N-(2-hydroxyphenyl)-2-thiophenecarboximidamide hydrochloride

The experimental protocol used is the same as that described for Example 17, with 2-aminophenol replacing 4-aminophenol. The reaction product is purified on a silica column (eluent: dichloromethane/methanol: 9/1). The free base is then salified using a 1M solution of HCl in anhydrous ethyl ether. The hydrochloride is obtained in the form of a cream powder with a yield of 20%.

Melting point: 206-207° C.

Example 19

N-(3-hydroxyphenyl)-2-thiophenecarboximidamide hydroiodide

The experimental protocol used is the same as that described for Example 17, with 3-aminophenol replacing 4-aminophenol. After drying the expected product is obtained in the form of a cream powder with a yield of 72%.

Melting point: 198-200° C.

Example 20

N-(3-hydroxy-4-methoxyphenyl)-2-thiophenecarboximidamide hydrochloride

The experimental protocol used is the same as that described for Example 0.18, with 5-amino-2-methoxyphenol replacing 2-aminophenol. After drying the expected product is obtained in the form of a cream powder with a yield of 30%.

Melting point: 253-254° C.

Example 21

N-(3-hydroxy-4-methylphenyl)-2-thiophenecarboximidamide hydrochloride

The experimental protocol used is the same as that described for Example 18, with 3-amino-o-cresol replacing 2-aminophenol. After drying the expected product is obtained in the form of a cream powder with a yield of 61%.

Melting point: 245-246° C.

Example 22

N-(4-methoxyphenyl)-2-thiophenecarboximidamide hydrochloride

The experimental protocol used is the same as that described for Example 18, with p-anisidine replacing 2-aminophenol. After drying the expected product is obtained in the form of a cream powder with a yield of 40%.

Melting point 78-79° C.

Example 23

N-(3,5-dimethyl-4-hydroxyphenyl)-2-thiophenecarboximidamide hydroiodide 23.1) 4-amino-2,6-dimethylphenol A solution of 1 g (6 mmole) of 2,6-dimethyl-4-nitrophenol in 20 ml of ethanol is placed under 1.5 bar of hydrogen in the presence, of 10% Pd/C for 1 hour. The Pd/C is eliminated by filtration on celite and the filtrate is concentrated under reduced pressure. The evaporation residue crystallizes spontaneously, it is washed twice with 50 ml of heptane and dried overnight under vacuum. A cream coloured solid is obtained with a yield of 86%.

Melting point: 139-140° C.

23.2) N-(3,5-dimethyl-4-hydroxyphenyl)-2-thiophenecarboximidamide hydroiodide

The experimental protocol used is the same as that described for Example 17, with 4-amino-2,6-dimethylphenol replacing 4-aminophenol. After drying the expected product is obtained in the form of a white powder with a yield of 65%.

Melting point: 253-254° C.

Example 24

N-(3,5-dichloro-4-hydroxyphenyl)-2-thiophenecarboximidamide hydrochloride

The experimental protocol used is the same as that described for Example 18, with 4-amino-2,6-dichlorophenol replacing 2-aminophenol. After drying the expected product is obtained in the form of a cream powder with a yield of 30%.

Melting point: >260° C.

Example 25

N-(3,5-bis-(1,1-dimethylethyl)-4-hydroxyphenyl)-2-thiophenecarboximidamide hydrochloride 25.1) 4-amino-2,6-bis-(1,1-dimethylethyl)-phenol 3.6 g (14 mmole) of 4-nitro-2,6-bis-(1,1-dimethylethyl)-phenol (J. Org. Chem. (1968), 33 (1), 223-226) is dissolved in 60 ml of a mixture (2/1) of ethanol and dichloromethane, in a 250 ml Parr bottle, in the presence of a catalytic quantity of 10% Pd/C. The mixture is agitated for 2 hours, at 20° C., under 20 PSI of hydrogen. After filtration on celite, the filtrate is concentrated to dryness under reduced pressure. The reddish brown powder obtained is suspended in heptane (30 ml), filtered and rinsed with the same volume of heptane. The expected product is obtained in the form of a salmon pink powder with a yield of 50% (1.56 g).

Melting point: 123-124° C.

NMR $^1$H (100 MHz, CDCl$_3$, δ): 6.60 (s, 2H, Ph); 4.65 (broad s, 1H, OH); 3.15 (broad s, 2H, NH$_2$); 1.42 (s, 18H, 2× tBu).

25.2) N-(3,5-bis-(1,1-dimethylethyl)-4-hydroxyphenyl)-2-thiophenecarboximidamide hydrochloride The experimental protocol used is the same as that described for Example 18, with 4-amino-2,6-bis-(1,1-dimethylethyl)-phenol replacing 2-aminophenol. After drying the expected product is obtained in the form of a pale yellow powder with a yield of 65%.

Melting point: 258-259° C.

NMR $^1$H (400 MHz, DMSO d6, δ): 1.42 (s, 18H, 2× tBu); 7.18 (s, 2H, Ph); 7.38 (s, 1H, OH); 7.39 (s, 1H, thiophene); 8.18 (m, 2H, thiophene); 8.80 (broad s, 1H, NH$^+$); 9.70 (broad s, 1H, NH$^+$); 11.30 (broad s, 1H, NH$^+$).

Example 26

N-{4-[4-[(3,4-dihydro-6-hydroxy-2,5,7,8-tetramethyl-2H-1-benzopyran-2-yl)methyl]-1-piperazinyl]phenyl}-2-thiophenecarboximidamide 26.1) 3,4-dihydro-2,5,7,8-tetramethyl-2-{4[(phenylmethyl)-1-piperazinyl]-carbonyl}-2H-1-benzopyran-6-ol 3.3 g (20.4 mmole) of 1,1'-carbonyldiimidazole is added to a solution of 5 g (20 mmole) of trolox in 40 ml of THF. After agitation for 1 hour at 23° C., 3.52 g (20 mmole) of 1-benzyl-piperazine dissolved in 20 ml of THF is added. After agitation for 15 hours, the reaction mixture is concentrated under vacuum. The evaporation residue is dissolved in 50 ml of dichloromethane and the solution is washed twice with 50 ml of water. The organic phase is dried over sodium sulphate, filtered and concentrated under vacuum. The evaporation residue is purified on a silica column (eluent: ethyl acetate/heptane: 3/2). 6.17 g of a white powder is obtained with a yield of 75%.

Melting point: 63-65° C.

26.2) 3,4-dihydro-2,5,7,8-tetramethyl-2-{4[(phenylmethyl)-1-piperazinyl]-methyl}-2H-1-benzopyran-6-ol A solution of 4 g (9.8 mmole) of intermediate 26.1 is added dropwise to a suspension of 0.74 g (19.6 mmole) of LiAlH$_4$ in 20 ml of THF at 0° C. After 15 minutes at 0° C., the reaction mixture is agitated for 18 hours at 23° C. The reaction is then cooled down using an ice bath and hydrolyzed by successively adding 4 ml of ethyl acetate, 0.8 ml of water, 0.8 ml of 15% soda and finally 2.4 ml of water. The reaction mixture is then filtered on celite and the precipitate is washed 3 times with 25 ml of ethyl acetate. The filtrate is concentrated under vacuum and the residue is purified on a silica column (eluent: ethyl acetate/heptane: 1/1). An orange oil is obtained with a yield of 65%.

26.3) 3,4-dihydro-2,5,7,8-tetramethyl-2-[(1-piperazinyl)-methyl]-2H-1-benzopyran-6-ol 0.4 g of 10% Pd/C is added to a solution of 2.52 g (6.39 mmole) of intermediate 26.2 in 15 ml of acetic acid. The mixture is agitated under 3 bars of hydrogen for 1 hour. The catalyst is eliminated by filtration and the filtrate is concentrated under vacuum. The residue is partitioned in a mixture of 80 ml of ethyl acetate and 100 ml of 2N NaOH. After decantation, the organic solution is washed twice with 150 ml of water, dried over sodium sulphate and filtered. The filtrate is concentrated under vacuum and the residue purified on a silica column (eluent; dichloromethane/methanol/$NH_4OH$ (28%): 25/110.5). A white solid is obtained with a yield of 62%.

26.4) 3,4-dihydro-2,5,7,8-tetramethyl-2-{4[(4-nitrophenyl)-1-piperazinyl]-methyl}-2H-1-benzopyran-6-ol 0.6 g (1.97 mmole) of intermediate 26.3, 0.54 g (3.94 mmole) of potassium carbonate and 0.31 g (2.17 mmole) of 1-fluoro-4-nitrobenzene are dissolved in 20 ml of DMF. The reaction mixture is heated at 100° C. for 16 hours. After returning to 23° C., the mixture is diluted with 30 ml of water and 30 ml of ethyl acetate. The organic phase is decanted, washed twice with 20 ml of water, dried over sodium sulphate and filtered. The filtrate is concentrated under vacuum and the evaporation residue is purified on a silica column (eluent: ethyl acetate/heptane: 1/1). A yellow powder is obtained with a yield of 52%.

Melting point: 72-75° C.

26.5) 3,4-dihydro-2,5,7,8-tetramethyl-2-{4[(4-aminophenyl)-1-piperazinyl]-methyl}-2H-1-benzopyran-6-ol The experimental protocol is identical to that described for intermediate 1.2, with intermediate 26.4 replacing intermediate 1.1. A yellow solid is obtained with a yield of 37%.

NMR $^1$H (100 MHz, $CDCl_3$, δ): 1.30 (s, 3H, $CH_3$); 2.00 (m, 4H, $CH_2$—$CH_2$); 2.10 (s, 6H, 2×$CH_3$); 2.20 (s, 3H, $CH_3$); 2.60 (s, 2H, $CH_2$); 2.75 (m, 6H, piperazine, $NH_2$); 3.00 (m, 4H, piperazine); 4.00 (broad s, 1H, OH); 6.70 (m, 4H, arom.).

26.6) N-{4-[4-[(3,4-dihydro-6-hydroxy-2,5,7,8-tetramethyl-2H-1-benzopyran-2-yl)methyl]-1-piperazinyl]phenyl}-2-thiophenecarboximidamide The experimental protocol is the same as that described for intermediate 1.3 except that the product remains in the form of a free base. A yellow powder is obtained with a yield of 55%. Melting point: 100-102° C.

NMR $^1$H (400 MHz, DMSO d6, δ): 1.25 (s, 3H, $CH_3$); 1.90 (m, 2H, Ω $CH_2$—$CH_2$); 2.14 (s, 3H, $CH_3$); 2.15 (s, 3H, $CH_3$); 2.20 (s, 3H, $CH_3$); 2.60 (s, 2H, $NH_2$); 2, 65 (broad s, 2H, Ω $CH_2$—$CH_2$); 2.80 (m, 4H, piperazine); 3.15 (m, 4H, piperazine); 4.80 (broad s, 1H, OH); 6.90 (s, 4H, arom.); 7.05 (m, 1H, thiophene); 7.40 (m, 2H, thiophene).

(MH)+: 505.3.

Example 27

1-(2-hydroxy-4,6-dimethoxybenzoyl)-3-{4-[(imino (2-thienyl)methyl) amino]phenoxy}azetidine hydrochloride 27.1) 1-(diphenylmethyl)-3-(4-nitrophenoxy)azetidine 0.5 g (2 mmole) of 1-(diphenylmethyl)-3-hydroxyazetidine is added to a suspension of 0.06 g (2.3 mmole) of NaH in 20 ml of dry THF, under an argon atmosphere. After agitation for one hour at 23° C., a solution of 0.29 g (2.1 mmole) of 4-fluoronitrobenzene in 5 ml of dry THF is added dropwise to the reaction mixture. Agitation is maintained for another 2 hours at 23° C. and the mixture is finally poured into 25 ml of water. The product is extracted twice with 25 ml of ethyl acetate, the organic phase is then washed twice with 25 ml of brine, dried over magnesium sulphate, filtered and concentrated under vacuum. The product is purified on a silica column (eluent: 12% ethyl acetate in heptane). The pure fractions are evaporated in order to produce a colourless oil with a yield of 40%.

NMR $^1$H ($CDCl_3$, 400 MHz, δ): 3.20 (m, 2H, azetidine); 4.50 (s, 1H, CH-($Ph$)$_2$); 4.80 (m, 2H, azetidine); 4.90 (m, 1H, CH—O); 6.80 (m, 2H, H arom.); 7.20-7.50 (m, 10H, H arom.); 8.20 (m, 2H, H arom.).

27.2) 1-(diphenylmethyl)-3-(4-aminophenoxy)azetidine 3.59 g (16 mmole) of $SnCl_2$, $2H_2O$ is introduced into a solution of intermediate 27.1 (1.14 g; 3.18 mmole) in 50 ml of an ethyl acetate/ethanol/acetone mixture (2/1/2). The reaction mixture is heated to reflux for 5 hours and finally after cooling down, concentrated by half under vacuum. The evaporation residue is then poured into 50 ml of a saturated solution of cold $NaHCO_3$ and extracted with 100 ml of ethyl acetate. The cloudy mixture is filtered on celite and the filtrate is decanted. The organic phase is washed successively with 50 ml of water and 50 ml of brine. After drying over magnesium sulphate and filtration, the organic solution is concentrated under vacuum.

A colourless oil is obtained with a yield of 75%.

NMR $^1$H ($CDCl_3$, 400 MHz, δ): 3.10 (m, 2H, azetidine); 3.40 (broad s, 2H, $NH_2$); 4.40 (s, 1H, CH-($Ph$)$_2$); 4.70 (m, 2H, azetidine); 4.75 (m, 1H, CH—O); 6.60 (s, 4H, H arom.); 7.10-7.40 (m, 10H, H arom.).

27.3) 1-(diphenylmethyl)-3-{4-[(1,1-dimethylethoxy)carbonyl]-aminophenoxy}azetidine The protection of the amine is carried out in a standard fashion using BocOBoc in the presence of triethylamine in dichloromethane. A white solid is obtained with a yield of 77%. Melting point: 149-151° C.

NMR $^1$H (DMSO d6, 400 MHz, δ): 1.40 (s, 9H, tBu); 2.90 (broad s, 2H, azetidine); 3.60 (broad s, 2H, azetidine); 4.50 (s, 1H, CH-($Ph$)$_2$); 4.70 (m, 1H, CH—O); 6.70 (m, 2H, H arom.); 7.10-7.60 (m, 12H, H arom.); 9.10 (s, 1H, NH).

27.4) 3-{4-[(1,1-dimethylethoxy)carbonyl]aminophenoxy)azetidine:

The experimental protocol used is the same as that described for intermediate 1.2 except for the hydrogenation catalyst which is replaced by Pd(OH)$_2$. A white solid is obtained with a yield of 78%. Melting point: 184-186° C.

NMR $^1$H (DMSO d6, 400 MHz, δ): 1.50 (s, 9H, tBu); 3.50 (m, 2H, azetidine); 3.70 (m, 2H, azetidine); 4.90 (m, 1H, CH—O); 6.70 (m, 2H, H arom.); 7.30 (m, 2H, H arom.); 9.10 (s, 1H, NH).

27.5) 1-(2-hydroxy-4,6-dimethoxybenzoyl)-3-{4-[(1,1-dimethylethoxy)carbonyl]-aminophenoxy}azetidine The experimental protocol used is the same as that described for Example 1, with 2-hydroxy-4,6-dimethoxybenzoic acid replacing 5-methoxysalicylic acid. A white solid is obtained. Melting point: 95° C.

NMR $^1$H (DMSO d6, 400 MHz, δ): 1.45 (s, 9H, Boc); 3.72 (s, 3H, —OCH$_3$); 3.73 (s, 3H, —OCH$_3$); 3.90 (m, 2H, CH—, azetidine); 4.20 (m, 1H, CH$_2$, azetidine); 4.40 (m, 1H, CH$_2$, azetidine); 5.00 (m, 1H, CH, azetidine); 6.07 (d, 2H, arom., J=8.95 Hz); 6.76 (d, 2H, arom., J=8.95 Hz); 7.36 (m, 2H, arom.); 9.2 (broad s, NH-Boc); 10.3 (broad s, 1H, —OH).

27.6) 1-(2-hydroxy-4,6-dimethoxybenzoyl)-3-aminophenoxy-azetidine:

Intermediate 27.5 (0.8 g; 1.8 mmole) is introduced into 20 ml of dichloromethane in a flask under an argon atmosphere. The solution is cooled down using an ice bath and trifluoroacetic acid (0.7 ml; 9.0 mmole) is added dropwise. Agitation is maintained while returning to ambient temperature overnight. The reaction mixture is evaporated to dryness, the residue is taken up in sodium bicarbonate and then extracted with ethyl acetate. The organic phase is dried over sodium sulphate, filtered and concentrated under vacuum. Purification is then carried out on a silica column (eluent=chloroform with 3% ethanol) in order to produce a white solid with a yield of 52%. Melting point: 95° C.

NMR $^1$H (CDCl$_3$, 400 MHz, δ); 3.60 (m, 2H, CH$_2$, azetidine); 3.80 (s, 3H, —OCH$_3$); 3.83 (s, 3H, —OCH$_3$); 4.20 (broad s, 2H, CH$_2$); 4.37 (m, 2H, CH$_2$, azetidine); 4.86 (m, 1H, CH, azetidine); 5.95 (s, 1H, arom.); 6.15 (s, 1H, arom.); 6.62 (m, 4H, arom.); 11.61 (broad s, 1H, —OH).

27.7) 1-(2-hydroxy-4,6-dimethoxybenzoyl)-3-{4-[(imino(2-thienyl)methyl)amino]phenoxy}azetidine hydrochloride The experimental protocol used is the same as that described for intermediate 1.3, with intermediate 27.6 replacing 2-hydroxy-5-methoxy-N-{2-(4-aminophenyl)ethyl}-benzamide. A white solid is obtained. Melting point: 185-187.7° C.

NMR $^1$H (DMSO d6, 400 MHz, δ): 3.71 (s, 3H, —OCH$_3$); 3.73 (s, 3H, —OCH$_3$); 3.85 (m, 2H, CH$_2$, azetidine); 4.32 (m, 2H, CH$_2$, azetidine); 5.08 (m, 1H, CH, azetidine); 6.09 (m, 2H, arom.); 7.02 (m, 2H, arom.); 7.36 (m, 3H, arom.); 8.16 (m, 2H, thiophene); 8.74 (broad s, 1H, NH$^+$); 9.72 (broad s, 1H, NH$^+$); 10.33 (s, 1H, —OH); 11.39 (broad s, 1H, NH$^+$).

IR: $v_{C=N}$ (amidine): 1590 cm$^{-1}$.

Example 28

N-(2-hydroxy-5-methoxy)-4-{[2-thienyl(imino)methyl]amino}benzene-butanamide hydrochloride 28.1) 2-amino-4-methoxyphenol The experimental protocol used is the same as that described for intermediate 1.2, with 4-methoxy-2-nitrophenol replacing 2-hydroxy-5-methoxy-N-{2-(4-nitrophenyl)ethyl}-benzamide.

28.2) N-(2-hydroxy-5-methoxy)-4-nitro-benzene-butanamide

The experimental protocol used is the same as that described for intermediate 1.1, with 4-(4-nitrophenyl)butanoic acid replacing 5-methoxysalicyclic acid and with 2-amino-4-methoxyphenol replacing 4-nitrophenethylamine hydrochloride.

28.3) N-(2-hydroxy-5-methoxy)-4-amino-benzene-butanamide.

The experimental protocol used is the same as that described for intermediate 1.2, N-(2-hydroxy-5-methoxy)-4 nitro-benzene-butanamide replacing 2-hydroxy-5-methoxy-N-{2-(4-nitrophenyl)ethyl}-benzamide.

28.4) N-(2-hydroxy-5-methoxy)-4-{[2-thienyl(imino)methyl]amino}benzene-butanamide hydrochloride The experimental protocol used is the same as that described for Example 1, with N-(2-hydroxy-5-methoxy)-4-amino-benzene-butanamide replacing 2-hydroxy-5-methoxy-N-{2-(4-aminophenyl) ethyl}-benzamide. Melting point: 199.1-200.7° C.

NMR $^1$H (DMSO d6, 400 MHz, δ): −1.9 (m, 2H, CH$_2$); 2.45 (m, 2H, CH$_2$); 2.70 (m, 2H, CH$_2$); 3.64 (s, 3H, —OCH$_3$); 6.51-6.9 (m, 2H, arom.); 7.36 (m, 6H, arom.); 8.17 (m, 2H, thiophene); 8.88 (broad s, 1H, NH$^+$); 9.38 (s, 2H, —OH & CONH); 9.81 (broad s, 1H, NH$^+$); 11.52 (broad s, 1H, NH$^+$).

IR: $v_{C=N}$ (amidine): 1662 cm$^{-1}$; $v_{C=O}$ (amide): 1693 cm$^{-1}$.

Example 29

N-(2-hydroxy-5-methoxy)-4-{[2-thienyl(imino)methyl]amino}benzene-propanamide 29.1) N-(2-hydroxy-5-methoxy)-4-N-Boc-benzene-propanamide.

The experimental protocol used is the same as that described for intermediate 28.2, with 3-(4-t-butoxycarbonylamino)phenylpropanoic acid replacing 4-(4-nitrophenyl)butanoic acid.

29.2) N-(2-hydroxy-5-methoxy)-4-amino-benzene-propanamide.

The experimental protocol used is the same as that described for intermediate 14.2, with N-(2-hydroxy-5-methoxy)-4-N-(4-t-butoxycarbonylamino)benzenepropanamide replacing N-(2-methoxymethoxy-3-tert-butyl-5-methoxy)$_4$-nitrobenzenebutanamide.

29.3) N-(2-hydroxy-5-methoxy)-4-{[2-thienyl (imino) methyl amino}-benzene-propanamide hydrochloride The experimental protocol used is the same as that described for Example 28, with N-(2-hydroxy-5-methoxy)-4-amino-benzene-propanamide replacing N-(2-hydroxy-5-methoxy)-4-amino-benzene-butanamide.

Melting point: 197.6-197.8° C.

NMR $^1$H (DMSO d6, 400 MHz, δ): 2.49 (m, 2H, CH$_2$); 2.70 (m, 2H, CH$_2$); 3.61 (s, 3H, —OCH$_3$); 6,50-7.00 (m, 2H, arom.); 7.40 (m, 6H, arom.); 8.90 (broad s, 1H, NH$^+$); 9.40 (s, 2H, —OH and —CONH); 9.90 (broad s, 1H, NH$^+$); 11.60 (broad s, 1H, NH$^+$).

IR: $v_{C=N}$ (amidine): 1660 cm$^{-1}$; $v_{C=O}$ (amide): 1685 cm$^{-1}$.

Example 30 tert-butyl 2-{[(4-{[amino(2-thienyl)methylidene] amino}phenethyl) amino]-carbonyl}-4-methoxyphenylcarbamate The experimental protocol used is the same as that described for Example 1, with 2-[(tert-butoxycarbonyl) amino]-5-methoxy benzoic acid (prepared in a standard fashion from commercial 2-amino-5-methoxy benzoic acid) replacing 5-methoxy salicylic acid.

White solid. Melting point: 190-192° C.

Example 31

2-amino-N-(4-{[amino(2-thienyl)methylidene]amino}phenethyl)-5-methoxybenzamide

Compound 31 is prepared from compound 30 which is treated in a standard fashion with hydrochloric acid in an organic solution, the product of the reaction is then purified on a silica column (eluent $CH_2Cl_2$/MeOH/$NH_4OH$: 80/20/0.5).

White solid. Melting point >200° C.

Example 32

5-amino-N-(4-{[amino(2-thienyl)methylidene]amino) phenethyl)-2-hydroxybenzamide

The experimental protocol used is identical to that described for Example 31, with 5-[(tert-butoxycarbonyl)amino]2-hydroxybenzoic acid replacing 2-amino-5-methoxy benzoic acid in the first stage.

Yellowish white solid. Melting point >260° C.

Example 33

N-(4-{[amino(2-thienyl)methylidene]amino}phenethyl)-2-hydroxy-5-methoxy-3-methyl-benzamide The experimental protocol used is the same as that described for Example 1, with 2-hydroxy-5-methoxy-3-methyl-benzoic acid (*Can. J. Chem.* (1972) 50, 1276-1282) replacing 5-methoxy salicylic acid.

Pale yellow solid. Melting point: 175.2-175.8° C.

Example 34

N-[2-(4-{[amino(2-thienyl)methylidene]amino}amino)-2-oxoethyl]-3,5-di(tert-butyl)-4-hydroxybenzamide The experimental protocol used is the same as that described for Example 1, starting with 3,5-di(tert-butyl)-4-hydroxybenzoic acid and glycine-p-nitroanilide.

White solid. Melting point >250° C.

Example 35

N'-{4-[4-(1,2,3,4-tetrahydro-2-naphthalenylcarbonyl)-1-piperazinyl]phenyl}-2-thiophenecarboximidamide hydrochloride The experimental protocol used is the same as that described for Example 1, starting with 1,2,3,4-tetrahydro-2-naphthoic acid and 4-nitrophenylpiperazine.

Pale yellow solid. Melting point: 191-194° C.

Example 36

4-(4-{[amino(2-thienyl)methylidene]amino}phenyl)-N-{4-[(methylsulphonyl)amino]phenyl}butanamide The experimental protocol used is the same as that described for Example 1, starting with 4-nitrophenylbutanoic acid and N-(4-aminophenyl)methanesulphonamide (*Farmaco* (1951) 6, 713-717).

Pale yellow solid. Melting point: 187.3-187.5° C.

Example 37

4-(4-{[amino(2-thienyl)methylidene]amino) phenyl)-N-[4-(dimethylamino)phenyl]butanamide hydrochloride The experimental protocol used is the same as that described for Example 1, starting with 4-nitrophenylbutanoic acid and N,N-dimethyl-p-phenylenediamine.

Pink solid. Melting point: 175-179° C.

Example 38

5-(4-{[amino(2-thienyl)methylidene]amino}phenyl)-N-[4-(dimethylamino)phenyl]pentanamide hydrochloride The experimental protocol used is the same as that described for Example 1, starting with 4-nitrophenylpentanoic acid (*J. Med. Chem.* (1978) 21 (5), 430-437) and N,N-dimethyl-p-phenylenediamine. White solid. Melting point: 166-168° C.

Examples 39 to 43 are synthesized according to the same strategy as that used for Example 1, except the nitro derivative reduction stage which is not carried out with hydrogen and Pd/C but in the presence of $SnCl_2,2H_2O$ as indicated in the synthesis of intermediate 27.2.

Example 39

(E)-N-(4-{[amino(2-thienyl)methylidene]amino}phenethyl)-3-(2-hydroxyphenyl)-2-propenamide White solid. Melting point: 145-155° C.

Example 40

(E)-N-(4-{[amino(2-thienyl)methylidene]amino}phenethyl)-3-(4-hydroxyphenyl)-2-propenamide Beige solid. MH+: 392.12.

Example 41

(E)-N-(4-{[amino(2-thienyl)methylidene]amino}phenethyl)-3-(3,4-dihydroxyphenyl)-2-propenamide Yellow oil. MH+: 408.08.

Example 42

(E)-N-(4-{[amino(2-thienyl)methylidene]amino}phenethyl)-3-(4-hydroxy-3,5-dimethoxyphenyl)-2-propenamide Pale yellow solid. Melting point: 196.4-197.6° C.

Example 43

(4R)-2-(3-{[amino(2-thienyl)methylidene]amino]-phenyl)-N-[4-(dimethylamino)phenyl]-1,3-thiazolidine-4-carboxamide hydrochloride Compound 43 is prepared from (4R)-2-(4-nitrophenyl)-thiazolidine-4-carboxylic acid (*Liebigs Ann. Chem.* (1987), 927-934).

White solid. Melting point: 195-197° C.

Example 44

N'-[4-(4-{2-[3,5-di(tert-butyl)-4-hydroxy-phenoxy]acetyl}-1-piperazinyl)phenyl]-2-thiophenecarboximidamide dihydrochloride 44.1) 2-[3,5-di(tert-butyl)-4-hydroxyphenoxy] acetic acid:

3.6 ml (46 mmole) of trifluoroacetic acid is added to a solution of 1.56 g (4.64 mmole) of tert-butyl 2-[3,5-di(tert-butyl)-4-hydroxyphenoxy] acetate (prepared according to *J. Heterocycl. Chem.* (1994) 31, 1439-1443) in 20 ml of dichloromethane. The reaction mixture is agitated for 1 hour, concentrated under vacuum and the residue is dissolved in 50 ml of Et2O. The organic solution is extracted twice with 25 ml of a saturated solution of NaHCO3, the aqueous phase is then washed with 25 ml of Et2O. The basic aqueous solution is then acidified, at 0° C., with a saturated solution of KHSO4 and finally the expected product is extracted using twice 25 ml of Et2O. The organic solution is dried over sodium sulphate, filtered and concentrated under vacuum in order to produce a white powder with a yield of 70%. Melting point: 172-173° C.

44.2) N'-[4-(4-{2-[3,5-di(tert-butyl)-4-hydroxyphenoxy]acetyl}-1-piperazinyl)phenyl]-2-thiophenecarboximidamide dihydrochloride:

The experimental protocol used is the same as that described for Example 1, starting with intermediate 44.1 and 4-nitrophenylpiperazine.

Yellow solid. Melting point: 187-188° C.

Example 45

N-{4-[4-(2-{[3,5-di(tert-butyl)-4-hydroxyphenyl]thio}acetyl)-1-piperazinyl]phenyl}-2-thiophenecarboximidamide The experimental protocol used is the same as that described for Example 1, starting with 2-{[3,5-di(tert-butyl)-4-hydroxyphenyl]thio}acetic acid (prepared according to *J. Med. Chem.* (1997) 40 (12), 1906-1918) and 4-nitrophenylpiperazine.

Yellow solid, Melting point: 67-69° C.

Example 46

N'-(4-{4-[2-(4-hydroxy-2,3,5,6-tetramethylphenoxy)-acetyl]-1-piperazinyl}phenyl)-2-thiophenecarboximidamide hydrochloride The experimental protocol used is the same as that described for Example 1, starting with 2-(4-hydroxy-2,3,5,6-tetramethylphenoxy)acetic acid and 4-nitrophenylpiperazine.

Pale yellow solid. Melting point: 210-212° C.

Example 47

N-(4-{[amino(2-thienyl)methylidene]amino}-phenethyl)-2-[3,5-di(tert-butyl)-4-hydroxyphenoxy]acetamide hydroiodide The experimental protocol used is the same as that described for Example 1, starting with intermediate 44.1 and 4-nitrophenethylamine. Yellow solid. Melting point: 158-159° C.

Example 48

N-{4-[2-({2-[3,5-di(tert-butyl)-4-hydroxyphenoxy]-ethyl}amino)ethyl]phenyl}-2-thiophenecarboximidamide hydrochloride 48.1) 2,6-di(tert-butyl)-4-{2-[(4-nitrophenetyl)amino]ethoxy}phenol:

1.92 g (4.5 mmole) of 2-[3,5-di(tert-butyl)-4-hydroxyphenoxy]-N-(4-nitrophenetyl)acetamide (synthesis intermediate of compound 47) is introduced into 80 ml of anhydrous THF in a flask, under an argon atmosphere. A solution of 13.45 ml (13.45 mmole) of BH3 in THF is added to the reaction mixture and the mixture is agitated while heating at reflux for 4 hours 30 minutes. At the end of the reaction, 10 ml of MeOH is added and heating is maintained for a further 30 minutes. The reaction mixture is then concentrated under vacuum, the residue is taken up in 30 ml of a MeOH/HCl 3N mixture (2/1) and the mixture is taken to reflux for another hour. The reaction mixture is returned to 22° C., diluted with 50 ml of $CH_2Cl_2$ and 2M aqueous soda is added until a basic pH is obtained. After decantation, the organic phase is washed successively with 20 ml of water and 20 ml of brine, dried over sodium sulphate, filtered and concentrated under vacuum. The expected product is purified by chromatography on a silica column (eluent: $CH_2Cl_2$/EtOH: 25/1). Pale yellow solid.

48.2) tert-butyl 2-[3,5-di(tert-butyl)-4-hydroxyphenoxy]ethyl(4-nitrophenetyl) carbamate 1.27 g (3 mmole) of intermediate 48.1 is dissolved in a mixture of 15 ml of $CH_2Cl_2$ and 0.53 ml (3 mmole) of N,N-diisopropylethylamine. The mixture is cooled down using an ice bath before the addition in one portion of 0.67 g (3 mmole) of (Boc)$_2$O. The reaction mixture is agitated at 23° C. for 5 hours. After concentration under vacuum, the residue is taken up in 50 ml of ethyl acetate and poured into a water-ice mixture. The organic phase is decanted, washed successively with 20 ml of water and 20 ml of brine.

After drying over sodium sulphate, filtration and concentration under vacuum, a yellow solid is obtained with a quantitative yield.

48.3) tert-butyl 4-aminophenetyl{2-[3,5-di(tert-butyl)-4-hydroxyphenoxy]-ethyl}carbamate 1.7 g (3 mmole) of intermediate 48.2 and 0.8 ml (15 mmole) of hydrazine hydrate are dissolved in 50 ml of absolute ethanol before the addition of 0.2 g of Raney Nickel. The reaction mixture is then heated to reflux until the starting-product totally disappears (4 hours 30 minutes). After cooling down; a small quantity of silica is added to the flask and the solvent is finally eliminated under vacuum. The powder thus obtained is placed directly at the top of a chromatography column. The product is eluted using a AcOEt/Heptane mixture: 1/2. The expected product is obtained in the form of an orange oil with a yield of 83%.

48.4) tert-butyl 4-{[amino(2-thienyl)methylidene]amino}phenethyl {2-[3,5-di(tert-butyl)-4-hydroxyphenoxy]ethyl}carbamate 0.93 g (1.9 mmole) of intermediate 48.3 and 0.60 g (2.1 mmole) of S-methyl-2-thiophenethiocarboximide hydroiodide (*Ann. Chim.* (1962) 7, 303-337) are dissolved in 50 ml of isopropanol. The reaction mixture is agitated for 15 hours at 60° C. After evaporation of the solvent under vacuum, the residue is taken up in 60 ml of AcOEt and 40 ml of a saturated solution of $Na_2CO_3$. The mixture is vigorously agitated and finally decanted. The organic phase is washed successively with 20 ml of water, 20 ml of brine, dried over sodium sulphate, filtered and concentrated under vacuum. The product is used directly in the following stage without additional purification.

48.5) N-{4-[2-({2-[3,5-di(tert-butyl)-4-hydroxyphenoxy]-ethyl}amino)ethyl]phenyl}-2-thiophenecarboximidamide 0.8 g (1.3 mmole) of intermediate 48.4 is dissolved in 20 ml of ethanol and 7 ml of a 3N solution of hydrochloric acid is added. The mixture is agitated for 1 hour at 23° C. After cooling down using an ice bath, the solution is rendered basic by adding $Na_2CO_3$. in powder form and the mixture is finally diluted with 50 ml of AcOEt. After vigorous agitation and decantation, the organic phase is washed with 20 ml of brine, dried over sodium sulphate, filtered and concentrated to dryness. The residue is purified on a silica column (eluent: AcOEt/Heptane/NH4OH: 12.5/12.5/0.5).

48.6) N-{4-[2-({2-[3,5-di(tert-butyl)-4-hydroxyphenoxy]-ethyl}-amino)ethyl]phenyl}-2-thiophenecarboximidamide hydrochloride Intermediate 48.5 (0.29 g, 0.6 mmole) is dissolved in 30 ml of absolute ethanol, the mixture is cooled down using an ice bath before the addition of 2.4 ml (2.4 mmole) of a 1N solution of HCl in anhydrous ether. After agitation for 30 minutes at 23° C., the solvent is evaporated off under vacuum in order to produce a pink solid. Melting point: 151-153° C.

Example 49 tert-butyl 3-{[amino(2-thienyl)methylidene]amino}benzyl {3-[4-(dimethylamino)anilino]-3-oxopropyl}carbamate 49.1) tert-butyl 3-[4-(dimethylamino)anilino]-3-oxopropyl carbamate:

The experimental protocol used is the same as that described for intermediate 1.1, starting with N-Boc-β-alanine and N,N-dimethyl-p-phenylenediamine. White solid.
Melting point: 166-168° C.

49.2) 3-amino-N-[4-(dimethylamino)phenyl]propanamide:

35 ml of a 6N solution of HCl is added to a solution of 3.46 g (11.3 mmole) of intermediate 49.1 in 85 ml of AcOEt. The reaction mixture is agitated for 15 minutes at 23° C. After decantation, the aqueous phase is collected, rendered basic by adding 2N NaOH at 0° C. The product is then extracted using twice 100 ml of $CH_2Cl_2$. The organic solution is then washed with 25 ml of brine, dried over sodium sulphate, filtered and concentrated under vacuum. A beige solid (73%) is obtained which is used as it is in the following stage.

49.3) N-[4-(dimethylamino)phenyl]-3-[(3-nitrobenzyl)amino]propanamide 1.15 g (5.5=mole) of intermediate 49.2, 0.92 g (6 mmole) of 3-nitrobenzaldehyde and 3 g of a previously activated pulverulent 4 Å molecular sieve are added successively to a flask containing 100 ml of anhydrous MeOH, under an inert atmosphere. The reaction mixture is agitated vigorously for 15 hours before the addition, by portions, of 0.24 g (6 mmole) of $NaBH_4$. The agitation is maintained for another 4 hours before the addition of 10 ml of water. After a quarter of an hour, the sieve is filtered out and the reaction mixture is extracted twice with 100 ml of $CH_2Cl_2$. The organic phase is washed successively with 50 ml of water, 50 ml of brine, dried over sodium sulphate, filtered and concentrated under vacuum. The residue is purified on a silica column (eluent: $CH_2Cl_2$/EtOH: 20/1). A beige solid is obtained with a yield of 86%.

49.4) tert-butyl 3-{[amino(2-thienyl)methylidene]amino}benzyl{3-[4-(dimethylamino)anilino]-3-oxopropyl}carbamate The experimental protocol used is identical to that described for the synthesis of intermediates 48.2 to 48.4. A white solid is obtained. Melting point: 70-72° C.

Example 50

3-[(3-{[amino(2-thienyl)methylidene]amino}-benzyl)amino]-N-[4-(dimethylamino)phenyl]propanamide hydrochloride This compound is obtained by conversion of compound 49 according to an experimental protocol described for intermediates 48.5 and 48.6. A beige solid is obtained. Melting point: 142-144° C.

Example 51

3-[(3-{[amino(2-thienyl)methylidene]amino}-benzyl)amino]-N-[3,5-di(tert-butyl)-4-hydroxyphenyl] propanamide hydrochloride The experimental protocol used is the same as that described for compound 50, with 4-amino-2,6-di(tert-butyl) phenol (intermediate 25.1) replacing N,N-dimethyl-p-phenylenediamine. A light beige solid is obtained. Melting point: 166-169° C.

Example 52

3-[(3-{[amino(2-thienyl)methylidene]amino}-benzyl)amino]-N-[4-(4-methyl-1-piperazinyl)phenyl] propanamide hydrochloride The experimental protocol used is the same as that described for compound 50, with 4-(4-methyl-1-piperazinyl) aniline replacing N,N-dimethyl-p-phenylenediamine. A light beige solid is obtained. Melting point: 195-197° C.

Example 53

3-[(3-{[amino(2-thienyl)methylidene]amino}-benzyl)amino]-N-[4-(4-morpholinyl)phenyl]propanamide hydrochloride The experimental protocol used is the same as that described for compound 50, with 4-(4-morpholinyl)aniline replacing-N,N-dimethyl-p-phenylenediamine. A light beige solid is obtained. Melting point: 190-192° C.

Example 54

3-[(3-{[amino(2-thienyl)methylidene]amino}-benzyl)amino]-N-(1-methyl-2,3-dihydro-1H-indol-5-yl)propanamide hydrochloride 54.1) 1-methyl-5-nitroindoline:

25 ml of anhydrous DMF is introduced into a 150 ml three-necked flask, under an inert atmosphere, followed by 0.84 g (21 mmole) of 60% NaH. The reaction mixture is cooled down using an ice bath before the dropwise addition of a solution of 3.28 g (20 mmole) of 5-nitroindoline in 5 ml of anhydrous DMF. Once this addition is complete, agitation is maintained for 1 hour at 23° C., before the dropwise introduction of a solution of 1.31 ml (21 mmole) of MeI in 5 ml of anhydrous DMF. Agitation is maintained for 15 hours at 23° C. The reaction is finally neutralized, at 0° C., with 20 ml of a saturated solution of $NH_4Cl$. The reaction mixture is then diluted with 20 ml of water and 50 ml of AcOEt. After decantation, the organic phase is washed successively with 20 ml of water, 20 ml of brine, dried over magnesium sulphate, filtered and concentrated under vacuum. A dark yellow powder is obtained.

54.2) 1-methyl-5-aminoindoline:

Approximately 400 mg of Raney nickel is added to a mixture of 2.84 g (15.9 mmole) of –1-methyl-5-nitroindoline and 4 ml (80 mmole) of hydrazine hydrate in 60 ml of absolute ethanol. The reaction mixture is heated to reflux for 5 hours. After returning to 23° C., a little silica is added to the flask and the solvent is evaporated off under vacuum. The evaporation residue is placed directly at the top of a chromatography column. The expected product is eluted using a Heptane/AcOEt mixture (3/7). A violet powder is obtained (65%) which is used directly in the following stage.

54.3) 3-[(3-{[amino(2-thienyl)methylidene]amino}-benzyl)amino]-N-(1-methyl-2,3-dihydro-1H-indol-5-yl)propanamide hydrochloride The experimental protocol used is the same as that described for compound 49, with 1-methyl-5-aminoindoline replacing N,N-dimethyl-p-phenylenediamine. Deprotection and salification are carried out according to the experimental protocol described for intermediate 48.5. A light beige solid is obtained. Melting point: 134-136° C.

Example 55

3-[(3-{[amino(2-thienyl)methylidene]amino}-benzyl)amino]-N-(1-benzyl-2,3-dihydro-1H-indol-5-yl)propanamide hydrochloride The experimental protocol used is the same as that described for compound 54, with benzyl bromide replacing iodomethane. A white solid is obtained. Melting point: 193-195° C.

Example 56

3-[(3-{[amino(2-thienyl)methylidene]amino}-benzyl)amino]-N-[1-(1-naphthylmethyl)-2,3-dihydro-1H-indol-5-yl]propanamide The experimental protocol used is the same as that described for compound 54, with 1-(chloromethyl)-naphthtalene replacing iodomethane. A beige solid is obtained. Melting point: 185-187° C.

Example 57

N'-[4-(2-{[5-(dimethylamino)-2-hydroxybenzyl]amino}ethyl)phenyl]-2-thiophenecarboximidamide The experimental protocol used is the same as that described for intermediates 49.3 and 48.2 to 48.5 starting with 4-nitrophenetylamine and 5-(dimethylamino)-2-hydroxybenzaldehyde (*Bull. Chem. Soc. Jpn.* (1978) 51 (8), 2433-2434). White solid. Melting point: 182.3-182.6° C.

Examples 58 to 65 are synthesized according to the same strategy as that used for Example 57.

Example 58

N-(4-{([(4-{[amino(2-thienyl)methylidene]amino}phenethyl)-amino]methyl}phenyl)acetamide White solid. Melting point: 237.8-239° C.

Example 59

N'-[4-(2-{[(8-hydroxy-2-quinolinyl)methyl]amino}ethyl)phenyl]-2-thiophenecarboximidamide Pale yellow solid. Melting point >230° C.

Example 60

N'-[4-(2-{[3-phenyl-2-propenyl]amino}ethyl)phenyl]-2-thiophenecarboximidamide hydroiodide White solid. Melting point: 151-153° C.

Example 61

N'-[4-(2-{[3-(4-hydroxy-3-methoxyphenyl)-2-propenyl]amino}ethyl)phenyl]-2-thiophenecarboximidamide di fumarate White solid. Melting point: 174-176° C.

Example 62

N'-[4-(2-{[3-(4-hydroxy-3,5-dimethoxyphenyl)-2-propenyl]amino}ethyl)phenyl]-2-thiophenecarbooximidamide dihydrochloride Beige solid. Melting point: 182-184° C.

Example 63

N'-[4-(2-{[5-(dimethylamino)-2-hydroxy-3-methoxybenzyl]amino}-ethyl)phenyl]-2-thiophenecarboximidamide 5-(dimethylamino)-2-hydroxy-3-methoxybenzaldehyde is prepared according to *Bull. Chem. Soc. Jpn.* (1978) 51 (8), 2433-2434). Brown foam.

Example 64

N'-(4-{2-[(2-hydroxy-4,6-dimethoxybenzyl)amino]ethyl}phenyl)-2-thiophenecarboximidamide White solid. Melting point >230° C.

Example 65

N'-[4-(2-{[(6-hydroxy-2,5,7,8-tetramethyl-3,4-dihydro-2H-chromen-2-yl)methyl]amino}ethyl)phenyl]-2-thiophenecarboximidamide This compound is prepared from 6-hydroxy-2,5,7,8-tetramethyl-2-chromanecarbaldehyde (*Bioorg. Med. Chem. Lett.* (1998) 8, 3453-3458).
White solid. Melting point >230° C.

Example 66

N'-(4-{2-[[(E)-3-(4-hydroxy-3,5-dimethoxyphenyl)-2-propenyl](methyl)amino]ethyl}phenyl)-2-thiophenecarboximidamide This compound is prepared from N-methyl-2-(4-nitrophenyl)-ethylamine hydrochloride and (E)-3-(4-hydroxy-3,5-dimethoxyphenyl)-2-propenal according to the experimental protocols described successively for intermediates 49.3, 27.2 and 1.3 (the product remaining in the form of the free base).
Pinkish white solid. Melting point: 153.2-154° C.

Example 67

4-{[(4-{[amino(2-thienyl)methylidene]amino}phenethyl)-amino]methyl}-1-pyridiniumolate 67.1) N'-(4-{2-[(4-pyridinylmethyl)amino]ethyl}phenyl)-2-thiophenecarboximidamide:
The experimental protocol used is the same as that described for compound 50 starting with isonicotinic aldehyde and 4-nitrophenethylamine.

67.2) 4-{[(4-{[amino(2-thienyl)methylidene]amino}phenethyl)-amino]methyl}-1-pyridiniumolate 0.1 g (0.23 mmole) of intermediate 67.2 is dissolved, under an argon atmosphere, in 10 ml of chloroform. The solution is cooled down to 0° C. before the dropwise addition of 0.052 g (0.3 mmole) of metachloroperbenzoic acid in 10 ml of chloroform. The reaction mixture is agitated for 30 minutes at 0° C. before being poured into a water+ice mixture. The product is extracted using twice 20 ml of $CH_2Cl_2$, the organic solution is washed with 20 ml of brine, dried over magnesium sulphate, filtered and concentrated under vacuum. The residue is purified on a silica column (eluent: $CH_2Cl_2$/EtOH/NH4OH: 0.5/9.5/0.5) in order to produce a yellow oil with a yield of 20%. MH+=453.18.

Example 68

N'-[4-(2-{[(2-hydroxy-4,6-dimethoxyphenyl)methylidene]-amino}ethyl)phenyl]-2-thiophenecarboximidamide The formation of the imine between the 2-hydroxy-4,6-dimethoxybenzaldehyde and 4-nitrophenethylamine is carried out according to the experimental protocol used for the synthesis of intermediate 49.3, except for the addition of $NaBH_4$. The other stages are identical to those described for the syntheses of intermediates 27.2 and 1.3 (the product remaining in the form of a free base). Bright yellow oil which partially crystallizes.

Example 69 tert-butyl 4-{[amino(2-thienyl)methylidene]amino}phenethyl(2-hydroxy-4,6-dimethoxybenzyl)carbamate The experimental protocol used is the same as that described for the synthesis of intermediates 49.3 and 49.4, starting with 2-hydroxy-4,6-dimethoxybenzaldehyde and 4-nitrophenetylamine. A pale yellow foam is obtained. MH+=512.23.

Example 70

N'-{4-[4-phenyl-3,6-dihydro-1(2H)-pyridinyl]phenyl}-2-thiophenecarboximidamide 70.1) 1-(4-nitrophenyl)-4-phenyl-1,2,3,6-tetrahydropyridine:
A mixture of 0.5 g (2.5 mmole) of 4-phenyl-1,2,3,6-tetrahydropyridine, 0.51 ml (2.8 mmole) of diisopropylethylamine, 0.71 g (5 mmole) of $K_2CO_3$, 0.40 g ((2.8 mmole) of 4-fluoronitrobenzene in 10 ml of DMF is heated at 100° C., for 24 hours. At the end of the reaction, the mixture is poured into 25 ml of a saturated solution of $NaHCO_3$ and the product is extracted using 25 ml of AcOEt. After decantation, the organic solution is washed twice with 20 ml of water followed by 20 ml of brine, drying over magnesium sulphate, filtration and evaporation of the solvent under vacuum produce a yellow solid with a yield of 42%. Melting point: 185-192° C. (decomposition).

70.2) N'-{4-[4-phenyl-3,6-dihydro-1 (2H)-pyridinyl]phenyl}-2-thiophene-carboximidami
The experimental-protocol used is the same as that described for intermediates 27.2 and 1.3 (the product remaining in the form of a free base).

Example 71

N'-(4-{2-[4-phenyl-3,6-dihydro-1 (2H)-pyridinyl]ethyl}phenyl)-2-thiophenecarboximidamide dihydrochloride 71.1) 1-(4-nitrophenethyl)-4-phenyl-1,2,3,6-tetrahydropyridine:
1.29 g (6.6 mmole) of 4-phenyl-1,2,3,6-tetrahydropyridine hydrochloride, 0.92 ml (6.6 mmole) of Et3N and 1.62 ml (6.6 mmole) of tributylphosphine are added to a solution of 1.0 g (5.98 mmole) of 4-nitrophenethyl alcohol in 25 ml of $CH_2Cl_2$. The reaction mixture is agitated vigorously at 23° C. and 1.04 ml (6.6 mmole) of diethylazodicarboxylate is added dropwise. After 4 hours, the reaction is stopped by adding 5 ml of a saturated solution of $NH_4Cl$. After decantation, the aqueous phase is extracted twice with 5 ml of $CH_2Cl_2$, the organic phases are combined and washed twice with 5 ml of water, twice with 5 ml of brine, dried over magnesium sulphate, filtered and concentrated under vacuum. The residue is purified on a silica column (eluent Heptane/AcOEt: 9/1 to 7/3) in order to produce 1.20 g of the expected product.

71.2) N'-(4-{2-[4-phenyl-3,6-dihydro-1 (2H)-pyridinyl]ethyl}phenyl)-2-thiophenecarboximidamide dihydrochloride The experimental protocol used is the same as that described for intermediates 27.2 and 1.3.

Pale yellow solid. Melting point: 185° C. (decomp.)

Example 72

N'-{4-[(1-benzhydryl-3-azetidinyl)oxy]phenyl}-2-thiophenecarboximidamide

The experimental protocol used is the same as that described for intermediate 1.3 (the product being isolated in the form of a free base), intermediate 27.2 replacing intermediate 1.2.

White solid. Melting point: 210-211° C.

Example 73

N'-[4-(2-quinolinylmethoxy)phenyl]-2-thiophenecarboximidamide hydroiodide 73.1) 2-[(4-nitrophenoxy)methyl]quinoline:

0.4 g (11 mmole) of 60% NaH is introduced into a flask containing 25 ml of anhydrous DMF under an argon atmosphere. A solution of 1.38 g (10 mmole) of 4-nitrophenol in 5 ml of anhydrous DMF is added dropwise, under agitation at 23° C. After 30 minutes a solution of 1.77 g (10 mmole) of 2-(chloromethyl)-quinoline in 5 ml of anhydrous DMF is added dropwise and agitation is continued for 15 hours while heating the mixture at 90° C. At the end of the reaction, the mixture is poured onto ice and an abundant precipitate forms. The suspension is filtered, rinsed twice with 25 ml of water followed by 20 ml of ethyl ether. A white solid is thus obtained with a yield of 75%. Melting point: 154-155° C.

73.2) N'-[4-(2-quinolinylmethoxy)phenyl]-2-thiophenecarboximidamide hydroiodide:

The experimental protocol used is the same as that described for intermediates 1.2 and 1.3, except that the hydroiodide precipitates spontaneously in the reaction, it is therefore isolated pure during simple filtration.

Example 74

N'-(4-{4-[2-hydroxy-2-methyl-4-(2,4,5-trimethyl-3,6-dioxo-1,4-cyclohexadien-1-yl)butanoyl]-1-piperazinyl}phenyl)-2-thiophenecarboximidamide The experimental protocol used is the same as that described in the literature (*Helv. Chim. Acta* (1963) 46, 333), starting with N-[4-(4-{[(2S)-6-hydroxy-2,5,7,8-tetramethyl-3,4-dihydro-2H-chromen-2-yl]carbonyl}-1-piperazinyl) phenyl]-2-thiophenecarboximidamide dihydrochloride (WO9842696, Example 27). A brown crystalline foam is obtained. MH+=534.20.

Example 75

N-{4-[2-(1,3-dimethyl-2,6-dioxo-1,2,3,6-tetrahydro-7H-purin-7-yl)ethyl]phenyl}-2-thiophenecarboximidamide fumarate 75.1) 1,3-dimethyl-7-(4-nitrophenetyl)-3,7-dihydro-1H-purine-2,6-dione:

A mixture of 0.59 g (3.26 mmole) of theophylline, 1.5 g (6,52 mmole) of 2-(4-nitrophenyl)ethyl bromide, 0.13 g (3.26 mmole) of NaOH pellets in 4 ml of water and 8 ml of isopropanol is heated to reflux for 24 hours. After returning to 23° C., the insoluble portion is filtered and the filtrate is extracted with 25 ml of $CH_2Cl_2$. The organic phase is washed with 10 ml of water followed by 10 ml of brine. After drying over sodium sulphate, filtration and concentration to dryness, the residue is purified on a silica column (eluent: $CH_2Cl_2$/MeOH: 95/5). A white solid is obtained with a yield of 50%.

75.2) N-{4-[2-(1,3-dimethyl-2,6-dioxo-1,2,3,6-tetrahydro-7H-purin-7-yl)ethyl]phenyl]-2-thiophenecarboximidamide fumarate The experimental protocol used is the same as that described for intermediates 1.2 and 1.3 except that the free base is salified in ethanol in the presence of fumaric acid. White solid. Melting point: 225-227° C.

Example 76

N'-(4-{4-[2,6-di(1-pyrrolidinyl)-4-pyrimidinyl]-1-piperazinyl}phenyl)-2-thiophenecarboximidamide 76.1) 4-[4-(4-nitrophenyl)-1-piperazinyl]-2,6-di(1-pyrrolidinyl)pyrimidine:

2.52 g (10 mmole) of 4-chloro-2,6-di-pyrrolidin-1-yl-pyrimidine (*J. Med. Chem.* (1990) 33 (4), 1145-1151) and 2.07 g (10 mmole) of 4-nitrophenylpiperazine are dissolved in a 250 ml flask containing 20 ml of anhydrous pyridine, under an argon atmosphere. The reaction mixture is heated at 100° C. for 48 hours. After cooling down, the contents of the flask are poured into 250 ml of water and the product is extracted using twice 50 ml of $CH_2Cl_2$. The organic phase is then washed with 50 ml of brine, dried over magnesium sulphate, filtered and concentrated under vacuum. The residue is purified on a silica column (eluent: Heptane/AcOEt: 2/1). An orange solid is obtained with a yield of 49%. Melting point: 200-201° C.

76.2) N'-(4-{4-[2,6-di(1-pyrrolidinyl)-4-pyrimidinyl]-1-piperazinyl}phenyl)-2-thiophenecarboximidamide The experimental protocol used is the same as that described for intermediates 1.2 and 1.3 except that the product is isolated in the form of a free base. Yellow solid. Melting point: 215-217° C.

Example 77

N'-{4-[2-({[4-(dimethylamino)anilino]carbonyl}amino)-ethyl]phenyl}-2-thiophenecarboximidamide hydroiodide 77.1) N-[4-(dimethylamino)phenyl]-N'-(4-nitrophenethyl)urea:

0.9 g (3.3 mmole) of triphosgene is dissolved in 5 ml of anhydrous $CH_2Cl_2$ in a 100 ml three-necked flask, under an argon atmosphere, and the solution is agitated at 23° C. Using a motorized syringe, a solution of 2.09 g (10 mmole) of N,N-dimethyl-p-phenylenediamine dihydrochloride and 5.2 ml (30 mmole) of diisopropylethylamine in 20 ml of anhydrous $CH_2Cl_2$ is added dropwise over 1 hour. Ten minutes after the addition is completed, a solution of 1.36 g (10 mmole) of 2-(4-aminophenyl)ethylamine and 1.8 ml of diisopropylethylamine in 5 ml of anhydrous $CH_2Cl_2$ is added in one portion. After agitation for 2 hours at 23° C., the precipitate formed is eliminated by filtration, the filtrate is washed with 10 ml of water followed by 10 ml of brine. The organic solution is dried over sodium sulphate, filtered and concentrated under vacuum.

The residue obtained is purified by being rapidly passed through a silica column (eluent: AcOEt). White solid.

77.2) N'-{4-[2-({[4-(dimethylamino)anilino]carbonyl}amino)-ethyl]phenyl}-2-thiophenecarboximidamide hydroiodide The experimental protocol used is the same as that described for the synthesis of intermediates 1.2 and 1.3 except that the hydroiodide precipitates spontaneously during the reaction, it is therefore isolated pure during a simple filtration.
Yellow solid. MH+=408.2.

Example 78

N-{[1-(4-{[amino(2-thienyl)methylidene]-amino}phenyl)-cyclobutyl]methyl}-6-hydroxy-2,5,7,8-tetramethyl-2-chromanecarboxamide hydrochloride 78.1) 2-[4-(2,5-dimethyl-1H-pyrrol-1-yl)phenyl]acetonitrile:

20 g (0.15 mol) of p-aminobenzyl cyanide, 19 ml (0.17 mol) of 2,5-dicetohexane and 2.88 g (0.015 mol) of hydrated p-toluene sulphonic acid are dissolved in a 500 ml flask. This mixture is heated to reflux, the water formed is trapped using a Dean Stark apparatus. At the end of the reaction, the solvent is evaporated off under vacuum and the residue is taken up in 300 ml of AcOEt. The organic solution is washed successively with twice 200 ml of water, 200 ml of a saturated solution of $Na_2CO_3$, 200 ml of water, 200 ml of a saturated solution of $KHSO_4$ and finally 200 ml of water and 200 ml of brine. After drying over sodium sulphate, filtration and concentration under vacuum, the residue is purified rapidly on a silica column. A light beige solid is obtained with a yield of 34%. Melting point: 112-113° C.

78.2) 1-[4-(2,5-dimethyl-1H-pyrrol-1-yl)phenyl]cyclopentanecarbonitrile:

0.88 g (22 mmole) of 60% NaH is introduced into a 100 ml three-necked flask containing 20 ml of anhydrous DMSO, under an argon atmosphere. A solution of 2.1 g (10 mmole) of intermediate 78.2 and 2.23 ml (11 mmole) of 1,3-dibromopropane in 10 ml of anhydrous DMSO is added as rapidly as possible to this suspension, under agitation. The addition speed is adjusted according to the temperature of the reaction medium which must remain in the region of 25-35° C. At the end of the reaction (1 hour 30 minutes), the contents of the flask are poured into 100 ml of a water+ice mixture. The product is extracted with 50 ml of AcOEt and the organic solution is washed successively with 5 times 20 ml of water, 20 ml of brine, dried over sodium sulphate, filtered and concentrated under vacuum. The residue is purified on a silica column (eluent: Heptane/AcOEt: 9/1). A white solid is obtained with a yield of 55%. Melting point: 117-120° C.

78.3) {1-[4-(2,5-dimethyl-1H-pyrrol-1-yl)phenyl]cyclopentyl}methanamine:

A solution of 2.03 g (8.1 mmole) of intermediate 78.2 in 20 ml of anhydrous THF is introduced dropwise at 0° C. into a 100 ml three-necked flask, under an argon atmosphere, containing 20 ml (20 mmole) of a 1M solution of $LiAlH_4$ in anhydrous THF. At the end of the addition, the reaction mixture is agitated for 3 hours at 23° C. The reaction mixture is then cooled down using an ice bath and the excess $LiAlH_4$ is destroyed by slowly adding 20 ml of AcOEt followed by 10 ml of a 1M aqueous solution of NaOH. After vigorous agitation for 30 minutes at 23° C., the contents of the three-necked flask are filtered through celite. The filtrate is diluted with 40 ml of AcOEt and 20 ml of water. After decantation, the organic solution is washed with 20 ml of a 1M solution of NaOH, 20 ml of brine, dried over sodium sulphate, filtered and concentrated under vacuum. The residue is purified on a silica column (eluent: $CH_2Cl_2$/EtOH: 9/1 to 8/2). A yellow oil is obtained with a yield of 64%.

78.4) N-({1-[4-(2,5-dimethyl-1H-pyrrol-1-yl)phenyl]cyclopentyl}methyl)-6-hydroxy-2,5,7,8-tetramethyl-2-chromanecarboxamide The experimental protocol used is the same as that described for intermediate 26.1, with intermediate 78.3 replacing 1-benzyl piperazine. A white solid is obtained with a yield of 79%. Melting point: 90-94° C.

78.5) N-{[1-(4-aminophenyl)cyclopentyl]methyl}-6-hydroxy-2,5,7,8-tetramethyl-2-chromanecarboxamide A solution of 0.49 g (1 mmole) of intermediate 78.4 and 1.05 g (15 mmole) of hydroxylamine hydrochloride in a mixture of 13 ml of isopropanol and 1 ml of water is heated at 100° C. for 72 hours. After cooling down, the solvent is evaporated off under vacuum and the residue is taken up in 20 ml of AcOEt and 20 ml of water. The organic phase is decanted and washed with 20 ml of water followed by 20 ml of brine, dried over sodium sulphate, filtered and concentrated under vacuum. The evaporation residue is purified on a silica column (eluent: Heptane/AcOEt: 6/4). The expected product is obtained in the form of a yellow oil with a yield of 50%.

78.6) N-{[1-(4-{[amino(2-thienyl)methylidene]amino}phenyl)-cyclobutyl]methyl}-6-hydroxy-2,5,7,8-tetramethyl-2-chromanecarboxamide hydrochloride The experimental protocol used is the same as that described for intermediate 1.3, with intermediate 78.5 replacing intermediate 1.2. Beige solid. Melting point: 185-187° C.

Example 79

N'-{4-[4-(5-methoxy-1H-indol-3-yl)-1-piperidinyl]-phenyl}-2-thiophenecarboximidamide hydrochloride 79.1) 5-methoxy-3-(1,2,3,6-tetrahydro-4-pyridinyl)-1H-indole:

The experimental protocol used is described in the literature (*Eur. J. Med. Chem.* (1987) 22, 33-43), starting from 5-methoxy-1H-indole and 4,4-piperidinediol.

79.2) 5-methoxy-3-[1-(4-nitrophenyl)-1,2,3,6-tetrahydro-4-pyridinyl]-1H-indole

The experimental protocol used is the same as the one described for intermediate 26.4, starting from intermediate 79.1.

79.3) 4-[4-(5-methoxy-1H-indol-3-yl)-1-piperidinyl]phenylamine:

9.2 g of zinc is added, by small portions, to a solution, cooled by an ice bath, of 0.7 g (2 mmole) of the intermediate 79.2 in 35 ml of acetic acid. This mixture is agitated for 18 hours at 20° C. before being filtered. The filtrate is concentrated under vacuum and the traces of acetic acid are eliminated by coevaporation in the presence of toluene. The evaporation residue is finally dissolved in 100 ml of $CH_2Cl_2$. The organic solution obtained is then washed successively with 50 ml of water and 50 ml of brine. After drying over $MgSO_4$, filtration and evaporation of the solvent under vacuum, the residue is used as is in the following stage.

79.4) N'-{4-[4-(5-methoxy-1H-indol-3-yl)-1-piperidinyl]-phenyl}-2-thiophenecarboximidamide hydrochloride The experimental protocol used is the same as that described for intermediate 1.3, the intermediate 79.3 replacing intermediate 1.2. Orange solid. Melting point: 209-213° C.

Example 80

N'-(4-{2-[[5-(dimethylamino)-2-hydroxy-3-methoxybenzyl]-(methyl)amino]ethyl}phenyl)-2-thiophenecarboximidamide The experimental protocol used is the same as the one described for Example 57, starting from 5-(dimethylamino)-2-hydroxy-3-methoxybenzaldehyde (prepared according to *Bull. Chem. Soc. Jpn.* (1978) 51 (8), 2433-2434) and N-methyl-2-(4-nitrophenyl)ethylamine hydrochloride. Dark yellow foam. MS: MH+: 439.2.

Example 81

4-(4-{[amino(2-thienyl)methylidene]amino}phenyl)-N-{1-[3-(dimethylamino)propyl]-2,3-dihydro-1H-indol-5-yl}butanamide 81.1) N,N-dimethyl-3-(5-nitro-2,3-dihydro-1H-indol-1-yl)-1-propanamine 4.92 g (30 mmole) of 5-nitroindoline is introduced by portions into a 250 ml double-necked flask, under argon atmosphere, containing a suspension of 2.4 g (60 mmole) of NaH (60%) in 60 ml DMF. The vigorous hydrogen evolution is accompanied by the formation of a red suspension. Agitation is maintained for 30 minutes at 23° C. before the addition, by portions, of 4.74 g (30 mmole) of 3-dimethylaminopropyl chloride hydrochloride. The reaction mixture is agitated and heated at 60° C. during 18 hours. The whole is finally poured into 200 ml of a water/ice mixture. The product is then extracted twice with 100 ml of AcOEt. The organic solution is washed successively with 100 ml of water and 100 ml of brine. After drying over MgSO$_4$ and concentration under vacuum, the evaporation residue is purified by flash chromatography an a silica column (eluent: AcOEt/MeOH: 100/0 to 0/100). A dark yellow oil is obtained with a yield of 48%.

81.2) 1-[3-(dimethylamino)propyl]-5-indolinamine

The experimental protocol used is the same as that described for intermediate 54.2, intermediate 81.1 replacing intermediate 54.1. Violet oil.

81.3) 4-(4-{[amino(2-thienyl)methylidene]amino}phenyl)-N-{1-[3-(dimethylamino)propyl]-2,3-dihydro-1H-indol-5-yl}butanamide The experimental protocol used is the same as that described for Example 1, starting from intermediate 81.2 and 4-nitrophenylbutanoic acid.

Example 82

3-[(5-{[amino(2-thienyl)methylidene]amino}-2-methoxybenzyl)amino]-N-[1-(1-naphthylmethyl)-2,3-dihydro-1H-indol-5-yl]propanamide The experimental protocol used is the same as that described for Example 56, 2-methoxy-5-nitrobenzaldehyde (*J. Org. Chem.* (1993) 58, 1385-1392) replacing 3-nitrobenzaldehyde.

Pharmacological Study of the Products of the Invention

Study of the Effects on Neuronal Constitutive NO Synthase of a Rat's Cerebellum

The inhibitory activity of the products of the invention is determined by measuring their effects on the conversion by NO synthase of [$^3$H]L-arginine into [$^3$H]L-citrulline according to the modified method of Bredt and Snyder (*Proc. Natl. Acad. Sci. USA,* (1990) 87: 682-685). The cerebellums of Sprague-Dawley rats (300 g—Charles River) are rapidly removed, dissected at 4° C. and homogenized in a volume of extraction buffer (HEPES 50 mM, EDTA 1 mM, pH 7.4, pepstatin A 10 mg/ml, leupeptin 10 mg/ml). The homogenates are then centrifuged at 21000 g for 15 min at 4° C. Dosage is carried out in glass test tubes in which 100 µl of incubation buffer containing 100 mM of HEPES (pH 7.4), 2 mM of EDTA, 2.5 mM of CaCl$_2$, 2 mM of dithiotreitol, 2 mM of reduced NADPH and 10 µg/ml of calmodulin are distributed. 25 µl of a solution containing 100 nM of [$^3$H]L-arginine (Specific activity: 56.4 Ci/mmole, Amersham) and 40 µM of non-radioactive L-arginine is added. The reaction is initiated by adding 50 µl of homogenate, the final volume being 200 µl (the missing 25 µl are either water or the tested product). After 15 min, the reaction is stopped with 2 ml of stopping buffer (20 mM of HEPES, pH 5.5, 2 mM of EDTA). After passing the samples through a 1 ml column of DOWEX resin, the radioactivity is quantified by a liquid scintillation spectrometer. The compounds of examples 1 to 7, 10 to 12, 19, 21, 22, 26 to 28, 31, 32, 38 to 42, 48, 50 to 62, 65, 66, 68, 71 and 73 described above show an IC$_{50}$ lower than 3.5 µM.

Study of the Effects on Lipidic Peroxidation of the Cerebral Cortex of a Rat

The inhibitory activity of the products of the invention is determined by measuring their effects on the degree of lipidic peroxidation, determined by the concentration of malondialdehyde (MDA). The MDA produced by peroxidation of unsaturated fatty acids is a good indication of lipidic peroxidation (H Esterbauer and K H Cheeseman, *Meth. Enzymol.* (1990) 186: 407-421). Male Sprague Dawley rats weighing 200 to 250 g (Charles River) were sacrificed by decapitation. The cerebral cortex is removed, then homogenized using a Thomas potter in a 20 mM Tris-HCl buffer, pH=7.4. The homogenate was centrifuged twice at 50000 g for 10 minutes at 4° C. The pellet is stored at −80° C. On the day of the experiment, the pellet is replaced in suspension at a concentration of 1 g/15 ml and centrifuged at 515 g for 10 minutes at 4° C. The supernatant is used immediately to determine the lipidic peroxidation. The homogenate of rat's cerebral cortex (500 µl) is incubated at 37° C. for 15 minutes in the presence of the compounds to be tested or of solvent (10 µl). The lipidic peroxidation reaction is initiated by adding 50 µl of FeCl$_2$ at 1 mM, EDTA at 1 mM and ascorbic acid at 4 mM. After incubation for 30 minutes at 37° C., the reaction is stopped by adding 50 µl of a solution of hydroxylated di tertio butyl toluene (BHT, 0.2%). The MDA is quantified using a colorimetric test, by reacting a chromogenic reagent (R), N-methyl-2-phenylindol (650 µl) with 200 µl of the homogenate for 1 hour at 45° C. The condensation of an MDA molecule with two molecules of reagent R produce a stable chromophore the maximum absorbence wavelength of which is equal to 586 nm. (Caldwell et al. *European J. Pharmacol.* (1995) 285, 203-206). The compounds of Examples 1, 3, 14 to 16, 25, 29, 32 to 34, 37 to 39, 41, 42, 44 to 48, 50, 51, 54 to 57, 61, 62, 70, 71, 74 and 76 to 78 described above-all show an IC$_{50}$ lower than 30 µM.

What is claimed is:

1. A compound of the formula (I')

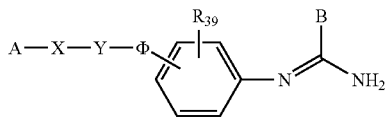

wherein

A is

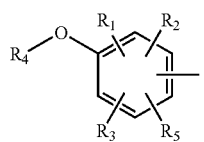

$R_{18}$, $R_{19}$ and $R_{20}$ are independently selected from the group consisting of hydrogen, —OH, alkyl or alkoxy of 1 to 6 carbon atoms, $R_{21}$ and $R_{22}$ are independently selected from the group consisting of hydrogen and alkyl of 1 to 6 carbon atoms, or $R_{21}$ and $R_{22}$ form together with the nitrogen atom an optionally substituted heterocycle having 4 to 7 members and 1 to 3 heteroatoms including the already present nitrogen atom, the additional heteroatoms being independently selected from the group consisting of O, N or furthermore $R_{21}$ is selected from the group consisting of alkylsulfonyl, alkylsulfoxide and alkylcarbonyl and then $R_{22}$ is hydrogen, B is thiophenyl, X is selected from the group consisting of a bond or —CO—$NR_{36}$—, Y is selected from the group consisting of a bond, —$(CH_2)_n$—, —$(CH_2)_r$-Q-$(CH_2)_s$— and thiazolidine, Q is selected from the group consisting of pinerazine, homopiperazine, 2-methylpiperazine, 2,5-dimethylpiperazine, piperidine, 1,2,3,6-tetrahydropyridine, pyrrolidine, azetidine, thiazolidine and a saturated carbon ring having 3 to 7 members, Φ is —$(CH_2)_p$—$NR_{37}$—$(CH_2)_q$—, $R_{36}$ and $R_{37}$ are independently selected from the group consisting of hydrogen, alkyl of 1 to 6 carbon atoms and —CO—$R_{38}$, $R_{38}$ is alkyl or alkoxy of 1 to 6 carbon atoms, $R_{39}$ is hydrogen, m, n, p, q, r and s are independently integers from 0 to 6, and its pharmaceutically acceptable salts.

2. A compound of claim 1 selected from the group consisting of 2-amino-N-(4-{[amino(2-thienyl)methylidene]amino}phenethyl)-5-methoxybenzamide;

5-amino-N-(4-{[amino(2-thienyl)methylidene]amino}phenethyl)-2-hydroxybenzamide;

4-(4-{[amino(2-thienyl)methylidene]amino}phenyl)-N-[4-[(methylsulphonyl)amino]phenyl]butanamide;

4-(4-{[amino(2-thienyl)methylidene]amino}phenyl)-N-[4-(dimethylamino)phenyl]butanamide;

5-(4-{[amino(2-thienyl)methylidene]amino}phenyl)-N-[4-(dimethylamino)phenyl]pentanamide;

(AR)-2-(3-{[amino(2-thienyl)methylidene]amino}phenyl)-N-[4-(dimethylamino)phenyl]-1,3-thiazolidine-4-carboxamide;

tert-butyl 3-{[amino(2-thienyl)methylidene]amino}benzyl(3-[4-(dimethylamino)anilino]-3-oxopropyl}carbamate;

3-[(3-{[amino(2-thienyl)methylidene]amino}-benzyl)amino]-N-[4-(4-methyl-1-piperazinyl)phenyl]propanamide;

3-[(3-{[amino(2-thienyl)methylidene]amino}-benzyl)amino]-N-[4-(4-morpholinyl)phenyl]propanamide;

N'-[4-(2-{[5-(dimethylamino)-2-hydroxybenzyl]amino}ethyl)phenyl]-2-thiophenecarboximidamide;

N-(4-{[(4-{[amino(2-thienyl)methylidone]amino)phenethyl)amino]methyl}phenyl)acetamide;

N'-[4-(2-{[5-(dimethylamino)-2-hydroxy-3-methoxybenzyl]amino}-ethyl)phenyl]-2-thiophenecarboximidamide;

N'-[4-(2-{([4-(dimethylamino)anilino]carbonyl}amino)-ethyl]phenyl}-2-thiophenecarboximidamide;

N'-[4-(2-{[5-(dimethylamino)-2-hydroxy-3-methoxybenzyl]-(methyl)amino]ethyl}phenyl)-2-thiophenecarboximidamide;

and the pharmaceutically acceptable salts of the latter.

* * * * *